(12) United States Patent
Oehrlein

(10) Patent No.: US 6,169,077 B1
(45) Date of Patent: Jan. 2, 2001

(54) SIALYL-LEWIS$^A$ AND SIALYL-LEWIS$^X$ EPITOPE ANALOGUES

(75) Inventor: Reinhold Oehrlein, Rheinfelden (DE)

(73) Assignee: GlycoTech Corp., Rockville, MD (US)

( * ) Notice: Under 35 U.S.C. 154(b), the term of this patent shall be extended for 0 days.

(21) Appl. No.: 09/117,482

(22) PCT Filed: Jan. 17, 1997

(86) PCT No.: PCT/EP97/00222

§ 371 Date: Feb. 11, 1999

§ 102(e) Date: Feb. 11, 1999

(87) PCT Pub. No.: WO97/28173

PCT Pub. Date: Aug. 7, 1997

(30) Foreign Application Priority Data

Jan. 30, 1996 (CH) .................................. 230/96

(51) Int. Cl.$^7$ .................. A61K 31/70; C07H 15/00; C07H 17/00

(52) U.S. Cl. ................ 514/25; 514/54; 514/61; 514/62; 514/536; 536/17.2; 536/18.7; 536/53; 536/55.2

(58) Field of Search ................. 514/25, 54, 61, 514/62; 536/17.2, 18.7, 53, 55.2

(56) References Cited

U.S. PATENT DOCUMENTS 4,925,796 * 5/1990 Bergh et al. ........................... 435/97

FOREIGN PATENT DOCUMENTS 94 26760 * 11/1994 (WO) .
94 29477 * 12/1994 (WO) .

OTHER PUBLICATIONS

Siuzdak et al. Chem. Sbstr. vol. 122, No. 17, Apr. 24, 1995, abstract No. 208092.

Bioorg. Med. Chem. Lett. 1994, 4(24), 2863–2866, No Month Available.

Hasegawa et al. Carbohydrate Research 1994, 257, 67–80, No Month Available.

Hasegawa et al. Carbohydrate Research 1995, 274, 165–181, No Month Available.

* cited by examiner

Primary Examiner—Kathleen K. Fonda
(74) Attorney, Agent, or Firm—Seed Intellectual Property Law Group PLLC

(57) ABSTRACT

Sialyl-Lewis$^x$ and sialyl-Lewis$^a$ epitope analogues in which the naturally occurring N-acetyl group of the N-acetylglucosamine monomer is replaced by various aliphatic or aromatic substituents and the L-fucose naturally present is replaced by various naturally occurring or non-naturally occurring sugars.

53 Claims, No Drawings

SIALYL-LEWIS$^a$ AND SIALYL-LEWIS$^x$ EPITOPE ANALOGUES

This application is the U.S. national stage entry under 35 U.S.C. §371 of PCT/EP97/00222, filed Jan. 17, 1997.

The invention relates to sialyl-Lewis$^a$ and sialyl-Lewis$^x$ epitope analogues, their preparation and use, and compositions comprising these compounds.

Carbohydrate domains and cell surfaces play a role in the treatment of many diseases, for example viral and bacterial infections, inflammatory diseases, rheumatic arthritis, allergies, post-infarction syndromes, septic shock, apoplexy, acute and chronic organ rejections, sepsis and cancer (formation of metastases) [Witczak, Z. J., Current Med. Commun. 1:392–405 (1995)]. Carbohydrate epitopes on eukaryotic cells are used by viruses, bacteria and toxins as specific adhesion points [Edwards, M., Curr. Op. in Therapeutic Patents 1617–1630 (1991)]. Carbohydrate domains also function as receptors of roaming malignant cells [Muramatsu, T., Glycobiology 3:294–296 (1993)]. However, they are also specific binding epitopes for certain transmembrane proteins, for example E-, P- and L-selectins. Selectins are found in the surface of both endothelial cells and circulating cells of the haemato-lymphoid system. They undergo specific interactions with carbohydrates [Lasky, L. A., Ann. Rev. Biochem. 64:113–139 (1995); Nelson, R. M., Dolich, S., Aruffo, A., Cecconi, O., Bevilacqua, M. P., J. Clin. Invest. 91:1157–1166 (1993)].

Sialylated and/or fucosylated carbohydrate epitopes are chiefly held responsible for such adhesion phenomena [Varki, A., Glycobiology 3:97–130 (1993)]. The two tetrasaccharide epitopes sialyl-Lewis$^a$ [αsia(2→3)βgal(1→3)[αfuc(1→4)]-βglcNAc-OR] and sialyl-Lewis$^x$ [αsia(2→3)βgal(1→4)[αfuc(1→3)]-βglcNAc-OR] (in which R must be an algycon having at least one carbon atom) are attributed particular importance in pathogenic inflammatory processes [Fukuda, M., Bioorg. Med. Chem. 3:207–215 (1995)].

Several routes have already been taken to isolate derivatives of these carbohydrate epitopes with better binding affinities than the naturally occurring ligand and an increased physiological stability. On the one hand, the natural epitope has been modified only slightly. Thus, N-acetylglucosamine has been replaced by sugars, such as glucosamine or glucose (WO 93/10,796), or by straight-chain or cyclic aliphatic radicals (EP 671,408). On the other hand, as many of the sugar monomers of the epitope as possible have been replaced by other functional units [Allanson, N. M., Davidson, A. H., Floyd, C. D., Martin, F. M., Tetra-hedron Assym. 5:2061–2076 (1994)]. However, none of these various approaches has so far led to epitope analogues having a significantly higher binding affinity. WO 94/26,760 discloses that compounds having higher binding affinities for selectins can be obtained if the N-acetyl group of N-acetylglucosamine, which is regarded as a group which is not relevant to binding (EP 671,408), is replaced by aromatic amides.

Surprisingly, the present invention provides sialyl-Lewis$^x$ and sialyl-Lewis$^a$ epitope analogues having an improved binding affinity for the corresponding selecting, in which the naturally occurring N-acetyl group of the N-acetylglucosamine monomer is replaced by various aliphatic and aromatic substituents and the L-fucose naturally present is replaced by various naturally occurring and non-naturally occurring sugars.

The present invention relates to compounds of the formula I or II

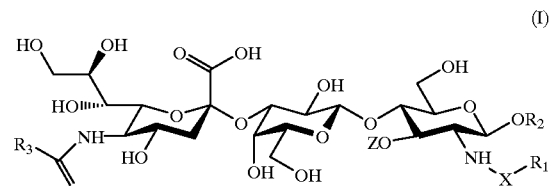

(I)

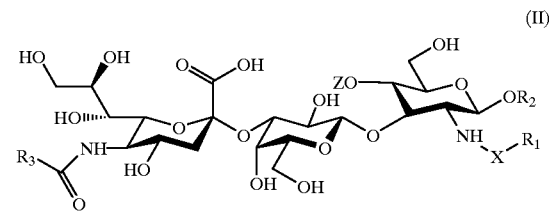

(II)

in which Z is an α-bonded pyranose of the formula III

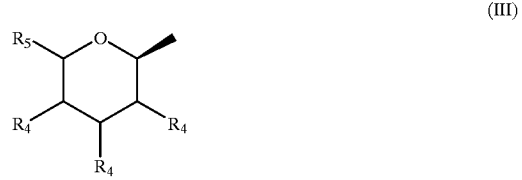

(III)

with the proviso that Z is not L-fucose, $R_1$ is hydrogen, $C_1$–$C_{20}$alkyl, $C_1$–$C_{20}$alkenyl, $C_3$–$C_{15}$cycloalkyl or a mono- or bicyclic $C_6$–$C_{10}$aryl or $C_2$–$C_9$heteroaryl, where alkyl, alkenyl, cycloalkyl, aryl and heteroaryl are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide;

$R_2$ is $C_1$–$C_{18}$alkyl, mono- or polysubstituted $C_1$–$C_{18}$alkyl, $C_3$–$C_8$cycloalkyl or mono- or polysubstituted $C_3$–$C_8$cycloalkyl, where one or more $CH_2$ groups in the alkyl and in the cycloalkyl, where appropriate, independently of one another are replaced by oxygen, sulfur or an imino group and the substituents are chosen from the group consisting of OH, SH, $NH_2$, carboxamide, C(O)O and $C_1$–$C_{18}$alkoxycarbonyl;

$R_3$ is a methyl or hydroxymethyl group;

the individual $R_4$ independently of one another are hydrogen, OH, $C_1$–$C_8$alkyl, O-$C_1$–$C_8$alkyl, halogen, $NH_2$, SH or NHC(O)-$C_1$–$C_8$alkyl;

$R_5$ is hydrogen, $C_1$–$C_8$alkyl or $(CH_2)_m R_4$, in which m is a number from 1 to 5; and X is —C(O)—, —C(S)—, —S(O)$_2$—, —C(O)Y— or —C(S)Y—, in which Y is NH, O, S, S-$C_1$–$C_6$alkylene, NH-$C_1$–$C_6$alkylene or O-$C_1$–$C_6$alkylene.

In the context of the present invention, the pyranose is advantageously D-fucose, D,L-arabinose, D,L-ribose, D,L- xylose, D,L-lyxose, L-rhamnose, D,L-galactose, D,L-glucose, D,L-mannose, D,L-gulose, D,L-allose, D,L-altrose, D,L-idose or D,L-talose, in particular D-fucose, D-arabinose, L-galactose or L-glucose. Preferred compounds are those in which the pyranose is an α-bonded D-fucose, D-arabinose, L-galactose or L-glucose, in which one or more $R_4$ independently of one another are hydrogen, halogen, sulfhydryl, a thioalkyl group, an amino group, an aminoalkyl group, a dialkylamino group or an aminoacyl group; and where the alkyl, where appropriate independently of one another, is a linear or branched $C_1$–$C_{18}$alkyl.

In the context of the present invention, the aryl or heteroaryl is a five- or six-membered ring or a bicyclic radical of two fused six- or five-membered rings or one six-membered and one five-membered ring, one or more heteroatoms chosen from the group consisting of the oxygen, nitrogen and sulfur atom being present in the heteroaryl. Examples are derived from benzene, pentalene, naphthalene, indene, furan, pyrrole, pyrazole, imidazole, isoxazole, oxazole, furazan, thiadiazole, thiophene, thiazole, oxadiazole, triazole, indole, indazole, purine, benzimidazole, benzoxazole, benzothiazole, pyran, pyridine, pyridazine, triazine, pyrimidine, pyrazine, isoquinoline, cinnoline, phthalazine, quinoline, quinazoline, pteridine, benzotriazine or quinoxaline.

Halogen is preferably F, Cl or Br.

The abovementioned alkyl and alkylene can be linear or branched. Some examples of alkyl, alkoxy, thioalkyl and alkylamino, which preferably contain 1 to 12 C atoms, are methyl, ethyl and the isomers of propyl, butyl, pentyl, hexyl, heptyl, octyl, nonyl, decyl, undecyl and dodecyl, and corresponding alkoxy, thioalkyl and alkylamino radicals. Preferred alkyl, alkoxy, thioalkyl and alkylamino radicals are methyl, ethyl, n- and i-propyl, n-, i- and t-butyl, methoxy, ethoxy, isopropyloxy, methylthio, isopropylthio and ethylthio, aminomethyl, aminoisopropyl and aminoethyl.

Examples of alkenyl are allyl, but-1-en-3- or -4-yl, pent-3- or -4-en-1-, -2- or -3-yl, hex-3-, -4- or -5-en-1- or -2-yl and ($C_1$–$C_4$alkyl)CH=CH—$CH_2$—. Examples of cycloalkyl are cyclopropyl, cyclobutyl, cyclopentyl, cyclohexyl and cycloheptyl.

In the context of the present invention, preferred compounds of the formula I or II are those in which $R_1$ is hydrogen, $C_1$–$C_{20}$alkyl or $C_1$–$C_{20}$alkenyl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkyl-amino, benzylamino, sulfhydryl, thio-$C_1$–$C_{18}$alkyl and $C_1$–$C_{18}$alkylcarboxamide. Particularly preferred compounds are those in which $R_1$ is $C_1$–$C_{10}$alkyl or $C_1$–$C_{10}$alkenyl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide. Particularly preferred compounds are those in which $R_1$ is $C_1$–$C_5$alkyl or $C_1$–$C_5$alkenyl, which are unsubstituted or substituted by OH or halogen, —$CH_3$, —$CF_3$, —$CH_2$—CH=$CH_2$, —$CH_2$OH and —$CH_2$SH being especially preferred.

Compounds of the formula I or II which are furthermore preferred are those in which $R_1$ is a mono- or bicyclic $C_6$–$C_{10}$aryl or $C_2$–$C_9$heteroaryl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide. Particularly preferred compounds of the formula I or II are those in which $R_1$ is a mono- or bicyclic $C_6$–$C_{10}$aryl or $C_2$–$C_9$heteroaryl, which are substituted by at least one OH and are not further substituted or are further mono- or polysubstituted by a substituent chosen from the group consisting of halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide. Especially preferred compounds of the formula I or II are those in which $R_1$ is phenyl or a mono- or bicyclic $C_4$–$C_9$heteroaryl, which are substituted by at least one OH and are not further substituted or are further substituted by a substituent chosen from the group consisting of halogen, nitro, $C_1$–$C_{18}$alkyl and $C_1$–$C_{18}$alkoxy. Very particularly preferred compounds are those in which $R_1$ is phenyl, which is substituted by one OH and F, $NO_2$, $CH_3$ or $OCH_3$ or by two OH; or in which $R_1$ is a $C_4$heteroaryl which is substituted by two OH, or a $C_9$heteroaryl which is substituted by one OH.

In the context of the present invention, preferred compounds of the formula I or II are furthermore those in which $R_2$ is $C_1$–$C_{18}$alkyl, mono- or polysubstituted $C_1$–$C_{18}$alkyl, $C_3$–$C_8$cycloalkyl or mono- or polysubstituted $C_3$–$C_8$cycloalkyl, where the substituents are chosen from the group consisting of OH, SH, $NH_2$, carboxamide, C(O)O and $C_1$–$C_{18}$alkoxycarbonyl. $R_2$ is particularly preferably $C_1$–$C_{18}$alkyl or $C_1$–$C_{18}$alkyl which is mono- or polysubstituted independently of one another by OH, SH, $NH_2$, carboxamide, C(O)O or $C_1$–$C_{18}$alkoxycarbonyl, $R_2$ is especially preferably $C_1$–$C_{18}$alkyl or $C_1$–$C_{18}$alkyl monosubstituted by C(O)O, and $R_2$ is most preferably —($CH_2$)$_8$$COOCH_3$.

In the context of the present invention, compounds of the formula I or II which are preferred are furthermore those in which $R_3$ is methyl.

Moreover, compounds of the formula I or II which are preferred are those in which the individual $R_4$ independently of one another are hydrogen, OH, $C_1$–$C_4$alkyl, O-$C_1$–$C_4$alkyl, halogen, $NH_2$ or NHC(O)-$C_1$–$C_8$alkyl. Particularly preferred compounds are those in which the individual $R_4$ independently of one another are OH, halogen or $NH_2$, especially those in which all the $R_4$ are OH or two $R_4$ are OH and one $R_4$ is halogen, in particular F, or $NH_2$.

Preferred compounds of the formula I or II are those in which $R_5$ is hydrogen, $C_1$–$C_8$alkyl or ($CH_2$)$_m$OH, in which m is an integer from 1 to 5, particularly preferably H, $C_1$–$C_4$alkyl or ($CH_2$)$_m$OH, in which m is 1 or 2, especially preferably hydrogen, $CH_3$ or $CH_2$OH.

In preferred compounds of the formula I or II, X is —C(O)—, —S(O)$_2$— or —C(O)Y—, in which Y is —NH—, —S-$C_1$–$C_6$-alkylene or —O-$C_1$–$C_6$alkylene, and X is, in particular, —C(O)—, —S(O)$_2$—, —C(O)S$CH_2$ or —C(O)O$CH_2$.

Preferred compounds of the formula I or II are, in particular, those in which $R_1$ is hydrogen, $C_1$–$C_{20}$alkyl or $C_1$–$C_{20}$alkenyl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide;

$R_2$ is $C_1$–$C_{18}$alkyl, mono- or polysubstituted $C_1$–$C_{18}$alkyl, $C_3$–$C_8$cycloalkyl or mono- or polysubstituted $C_3$–$C_8$cycloalkyl, where the substituents are chosen from the group consisting of OH, SH, $NH_2$, carboxamide, C(O)O and $C_1$–$C_{18}$alkoxycarbonyl;

$R_3$ is methyl;

the individual $R_4$ independently of one another are hydrogen, OH, $C_1$–$C_4$alkyl, O-$C_1$–$C_4$alkyl, halogen, $NH_2$ or NHC(O)-$C_1$–$C_8$alkyl;

$R_5$ is hydrogen, $C_1$–$C_8$alkyl or $(CH_2)_m$OH, in which m is a number from 1 to 5; and X is —C(O)—, —S(O)$_2$— or —C(O)Y—, in which Y is —NH—, —S-$C_1$–$C_6$alkylene or —O-$C_1$–$C_6$alkylene.

Very particularly preferred compounds of the formula I or II are those in which $R_1$ is $C_1$–$C_{10}$alkyl or $C_1$–$C_{10}$alkenyl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide;

$R_2$ is $C_1$–$C_{18}$alkyl or $C_1$–$C_{18}$alkyl which is mono- or polysubstituted independently of one another by OH, SH, $NH_2$, carboxamide, C(O)O or $C_1$–$C_{18}$alkoxycarbonyl;

$R_3$ is methyl;

the individual $R_4$ independently of one another are OH, halogen or $NH_2$;

$R_5$ is H, $C_1$–$C_4$alkyl or $(CH_2)_m$OH, in which m is 1 or 2; and

X is —C(O)—, —S(O)$_2$—, —C(O)SCH$_2$ or —C(O)OCH$_2$.

Of these compounds, especially preferred compounds are those in which $R_1$ is $C_1$–$C_5$alkyl or $C_1$–$C_5$alkenyl, which are unsubstituted or substituted by OH or halogen;

$R_2$ is $C_1$–$C_{18}$alkyl or $C_1$–$C_{18}$alkyl which is monosubstituted by C(O)O;

all the $R_4$ are OH or two $R_4$ are OH and one $R_4$ is halogen or $NH_2$; and $R_5$ is hydrogen, $CH_3$ or $CH_2OH$.

Especially preferred compounds within this group are those in which $R_1$ is —$CH_3$, —$CH_2$—CH=$CH_2$, —$CF_3$ or —$CH_2OH$; $R_2$ is —$(CH_2)_8COOCH_3$; all the $R_4$ are OH or two $R_4$ are OH and one $R_4$ is F or $NH_2$; and $R_5$ is hydrogen, $CH_3$ or $CH_2OH$.

Preferred compounds of the formula I or II are furthermore, in particular, those in which $R_1$ is a mono- or bicyclic $C_6$–$C_{10}$aryl or $C_2$–$C_9$heteroaryl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide;

$R_2$ is $C_1$–$C_{18}$alkyl, mono- or polysubstituted $C_1$–$C_{18}$alkyl, $C_3$–$C_8$cycloalkyl or mono- or polysubstituted $C_3$–$C_8$cycloalkyl, where the substituents are chosen from the group consisting of OH, SH, $NH_2$, carboxamide, C(O)O and $C_1$–$C_{18}$alkoxycarbonyl;

$R_3$ is methyl;

the individual $R_4$ independently of one another are hydrogen, OH, $C_1$–$C_4$alkyl, O-$C_1$–$C_4$alkyl, halogen, $NH_2$ or NHC(O)-$C_1$–$C_8$alkyl;

$R_5$ is hydrogen, $C_1$–$C_8$alkyl or $(CH_2)_m$OH, in which m is a number from 1 to 5; and X is —C(O)—, —S(O)$_2$— or —C(O)Y—, in which Y is —NH—, —S-$C_1$–$C_6$alkylene or —O-$C_1$–$C_6$alkylene.

Very particularly preferred compounds of the formula I or II are those in which $R_1$ is a mono- or bicyclic $C_6$–$C_{10}$aryl or $C_2$–$C_9$heteroaryl, which are substituted by at least one OH and are not further substituted or are further mono- or polysubstituted by a substituent chosen from the group consisting of halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide;

$R_2$ is $C_1$–$C_{18}$alkyl or $C_1$–$C_{18}$alkyl which is mono- or polysubstituted independently of one another by OH, SH, $NH_2$, carboxamide, C(O)O or $C_1$–$C_{18}$alkoxycarbonyl;

$R_3$ is methyl;

the individual $R_4$ independently of one another are OH, halogen or $NH_2$;

$R_5$ is H, $C_1$–$C_4$alkyl or $(CH_2)_m$OH, in which m is 1 or 2; and

X is —C(O)—, —S(O)$_2$—, —C(O)SCH$_2$ or —C(O)OCH$_2$.

Of these compounds, especially preferred compounds are those in which $R_1$ is phenyl or a mono- or bicyclic $C_4$–$C_9$heteroaryl, which are substituted by at least one OH and are not further substituted or are further substituted by a substituent chosen from the group consisting of halogen, nitro, $C_1$–$C_{18}$alkyl and $C_1$–$C_{18}$alkoxy;

$R_2$ is $C_1$–$C_{18}$alkyl or $C_1$–$C_{18}$alkyl which is monosubstituted by C(O)O;

all the $R_4$ are OH or two $R_4$ are OH and one $R_4$ is halogen or $NH_2$; and $R_5$ is hydrogen, $CH_3$ or $CH_2OH$.

Within this group, especially preferred compounds are those in which $R_1$ is phenyl, which is substituted by one OH and F, $NO_2$, $CH_3$ or $OCH_3$ or by two OH; or in which $R_1$ is a $C_4$heteroaryl which is substituted by two OH, or a $C_9$heteroaryl which is substituted by one OH; $R_2$ is —$(CH_2)_8$COOCH$_3$; all the $R_4$ are OH or two $R_4$ are OH and one $R_4$ is F or NH$_2$; and $R_5$ is hydrogen, CH$_3$ or CH$_2$OH.

The most preferred compounds of the formula I are those in which $R_2$ is —$(CH_2)_8$COOCH$_3$; $R_3$ is methyl; and (a) $R_1$ is hydrogen; Z is an α-bonded L-galactose; and X is —C(O)—;

(b) $R_1$ is —CH$_2$—CH═CH$_2$; Z is an α-bonded L-galactose; and X is —C(O)OCH$_2$—;

(c) $R_1$ is —CH$_2$—CH═CH$_2$; Z is an α-bonded D-arabinose; and X is —C(O)OCH$_2$—;

(d) $R_1$ is 4-hydroxy-3-methoxy-phenyl; Z is an α-bonded D-arabinose; and X is —C(O)—;

(e) $R_1$ is 4-hydroxy-3-methoxy-phenyl; Z is an α-bonded L-galactose; and X is —C(O)—;

(f) $R_1$ is 2-hydroxy-5-methyl-phenyl; Z is an α-bonded D-arabinose; and X is —C(O)—;

(g) $R_1$ is 2-hydroxy-5-methyl-phenyl; Z is an α-bonded L-galactose; and X is —C(O)—;

(h) $R_1$ is 2-hydroxy-3-nitro-phenyl; Z is an α-bonded L-galactose; and X is —C(O)—;

(i) $R_1$ is 2-hydroxy-5-fluoro-phenyl; Z is an α-bonded D-arabinose; and X is —C(O)—;

(j) $R_1$ is 3,5-dihydroxy-phenyl; Z is an α-bonded D-arabinose; and X is —C(O)—;

(k) $R_1$ is 3,5-dihydroxy-phenyl; Z is an α-bonded L-galactose; and X is —C(O)—;

(l) $R_1$ is 3,5-dihydroxy-pyrimidinyl; Z is an α-bonded D-arabinose; and X is —C(O)—;

(m) $R_1$ is 3,5-dihydroxy-pyrimidinyl; Z is an α-bonded L-galactose; and X is —C(O)—; or (n) $R_1$ is 2-(8-hydroxy)quinolinyl; Z is an α-bonded L-galactose; and X is —C(O)—.

Within this group, particularly preferred compounds of the formula I are those in which $R_2$ is —$(CH_2)_8$COOCH$_3$; $R_3$ is methyl; Z is an α-bonded L-galactose; X is —C(O)— and $R_1$ is hydrogen; 4-hydroxy-3-methoxy-phenyl; 2-hydroxy-5-methyl-phenyl; 2-hydroxy-3-nitrophenyl; 3,5-dihydroxy-phenyl; 3,5-dihydroxy-pyrimidinyl or 2-(8-hydroxy)quinolinyl. That compound in which $R_2$ is —$(CH_2)_8$ COOCH$_3$; $R_3$ is methyl; Z is an α-bonded L-galactose; X is —C(O)— and $R_1$ is 4-hydroxy-3-methoxy-phenyl is especially preferred.

The most preferred compounds of the formula II are those in which $R_2$ is —$(CH_2)_8$COOCH$_3$; $R_3$ is methyl; and (a) $R_1$ is hydrogen; Z is an α-bonded D-arabinose; and X is —C(O)—;

(b) $R_1$ is hydrogen; Z is an α-bonded L-2-fluoro-fucose; and X is —C(O)—;

(c) $R_1$ is CH$_3$; Z is an α-bonded D-arabinose; and X is —C(O)—;

(d) $R_1$ is CH$_3$; Z is an α-bonded L-2-fluoro-fucose; and X is —C(O)—;

(e) $R_1$ is CH$_3$; Z is an α-bonded L-2-aminoiucose; and X is —C(O)—;

(f) $R_1$ is CH$_3$; Z is an α-bonded L-galactose; and X is —C(O)—;

(g) $R_1$ is CH$_3$; Z is an α-bonded L-glucose; and X is —C(O)—;

(h) $R_1$ is CH$_3$; Z is an α-bonded L-galactose; and X is —C(O)OCH$_2$—;

(i) $R_1$ is CH$_3$; Z is an α-bonded L-glucose; and X is —C(O)OCH$_2$—;

(j) $R_1$ is CH$_3$; Z is an α-bonded D-arabinose; and X is S(O)$_2$;

(k) $R_1$ is CH$_3$; Z is an α-bonded D-arabinose; and X is —C(O)SCH$_2$—;

(l) $R_1$ is CF$_3$; Z is an α-bonded D-arabinose; and X is —C(O)—;

(m) $R_1$ is CH$_2$OH; Z is an α-bonded D-arabinose; and X is —C(O)—;

(n) $R_1$ is —CH$_2$—CH═CH$_2$; Z is an α-bonded D-arabinose; and X is —C(O)OCH$_2$—;

(o) $R_1$ is —CH$_2$—CH═CH$_2$; Z is an α-bonded L-galactose; and X is —C(O)OCH$_2$—;

(p) $R_1$ is phenyl; Z is an α-bonded L-galactose; and X is —C(O)OCH$_2$—;

(q) $R_1$ is 2-hydroxy-5-methyl-phenyl; Z is an α-bonded D-arabinose; and X is —C(O)—;

(r) $R_1$ is 2-hydroxy-5-methyl-phenyl; Z is an α-bonded L-galactose; and X is —C(O)—;

(s) $R_1$ is 2-hydroxy-5-mluoro-phenyl; Z is an α-bonded D-arabinose; and X is —C(O)—;

(t) $R_1$ is 4-hydroxy-3-methoxy-phenyl; Z is an α-bonded D-arabinose; and X is —C(O)—;

(u) $R_1$ is 3,5-dihydroxy-phenyl; Z is an α-bonded L-galactose; and X is —C(O)—;

(v) $R_1$ is 3,5-dihydroxy-phenyl; Z is an α-bonded L-2-amino-fucose; and X is —C(O)—;

(w) $R_1$ is 3,5-dihydroxy-phenyl; Z is an α-bonded D-arabinose; and X is —C(O)OCH$_2$— or (x) $R_1$ is 3,5-dihydroxy-pyrimidinyl; Z is an α-bonded D-arabinose; and X is —C(O)—.

Within this group, particularly preferred compounds of the formula II are those in which $R_1$ is CH$_3$; $R_2$ is —$(CH_2)_8$ COOCH$_3$; $R_3$ is methyl; Z is an α-bonded L-galactose and X is —C(O)— or —C(O)OCH$_2$—.

The present invention furthermore relates to a process for the preparation of compounds of the formula I, which comprises (a) reacting a compound of the formula V

$$R_7—X'—R_1 \qquad (V),$$

in which (a') $R_7$ is halogen, X' is as defined above for X and $R_1$ is as defined above, or (a") $R_7$ is C(O) or C(S), X' is —N═ and $R_1$ is as defined above, or (a'") $R_7$ is OH, X' is as defined above for X and $R_1$ is as defined above, directly after in situ activation analogously to methods such as are customary in peptide chemistry [Bodansky, M., Principles of Peptide Chemistry, 2nd Edition 16–61, Springer Berlin (1993)], with a compound of the formula IV

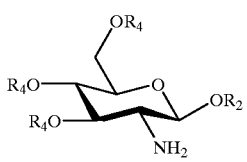

(IV)

in which $R_2$ is as defined above and the individual $R_4$ independently of one another are hydrogen, acetyl, propionyl, butyryl or benzoyl, any acetyl, propionyl, butyryl or benzoyl groups present being split off with a basic alcohol solution, to give a compound of the formula VI

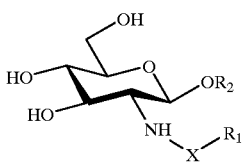

(VI)

in which $R_2$, $R_1$ and X are as defined above;

(b) reacting the compound of the formula VI with uridine di-phosphate-galactose in the presence of β(1→4) galactose transferase and then with cytidine mono-phosphate-sialic acid in the presence of α(2→3)sialic acid transferase to give a compound of the formula VII

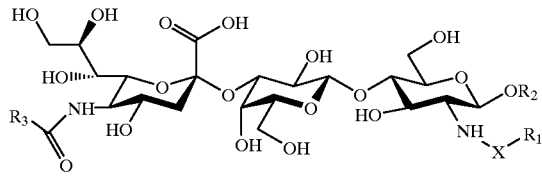

(VII)

in which $R_1$, $R_2$, $R_3$ and X are as defined above, and (c) reacting the resulting product with a guanosine di-phosphate-activated donor of the formula XI The present invention furthermore relates to a process for the preparation of compounds of the formula II, which comprises (a) reacting a compound of the formula VI with uridine di-phosphate-galactose in the presence of β(1→4) galactose transferase and then with cytidine mono-phosphate-sialic acid in the presence of α(2→3)sialic acid transferase to give a compound of the formula VII and (b) reacting the resulting product with a compound of the formula XI in the presence of fucose transferase to give a compound of the formula I.

The present invention furthermore relates to a process for the preparation of compounds of the formula II which comprises (a) reacting a compound of the formula IV with a compound of the formula V as described for the preparation of the compounds of the formula I, (b) reacting the compound of the formula VI with uridine di-phosphate-galactose in the presence of β(1→3) galactose transferase and then cytidine mono-phosphate-sialic acid in the presence of α(2→3)sialic acid transferase to give a compound of the formula VIII

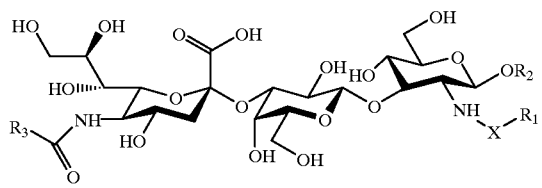

(VIII)

in which $R_1$, $R_2$, $R_3$ and X are as defined above, and (c) reacting the resulting product with a compound of the formula XI in the presence of fucose transferase to give a compound of the formula II.

The present invention furthermore relates to a process for the preparation of compounds of the formula II, which comprises (a) reacting a compound of the formula VI with uridine di-phosphate-galactose in the presence of β(1→3) galactose transferase and then with cytidine mono-

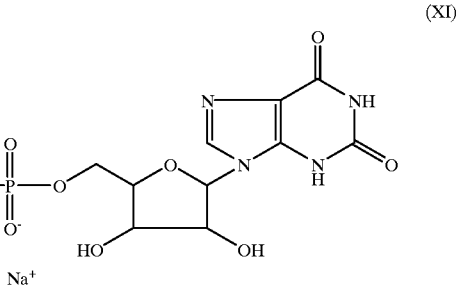

(XI)

in which $R_4$ and $R_5$ are as defined above, in the presence of fucose transferase VI to give a compound of the formula I.

phosphate-sialic acid in the presence of α(2→3)sialic acid transferase to give a compound of the formula VIII and (b) reacting the resulting product with a compound of the formula XI in the presence of fucose transferase to give a compound of the formula II.

The present invention furthermore relates to a process for the preparation of compounds of the formula II, which comprises (a) reacting a compound of the formula V

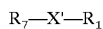  (V), in which to give a compound of the formula X

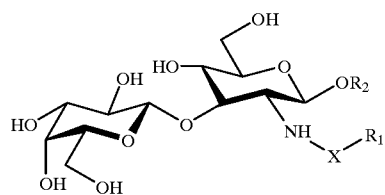

in which $R_2$, $R_1$ and X are as defined above;

(b) reacting the compound of the formula X with cytidine mono-phosphate-sialic acid in the presence of α(2→3) sialic acid transferase to give a compound of the formula VIII

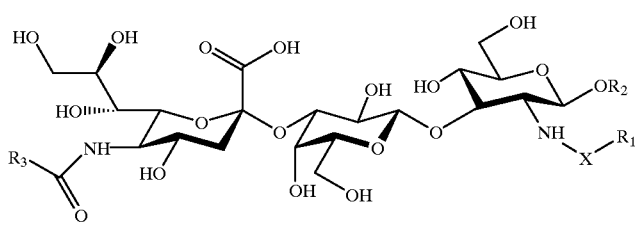

(a') $R_7$ is halogen, X' is as defined above for X and $R_1$ is as defined above, or (a'') $R_7$ is C(O) or C(S), X' is —N= and $R_1$ is as defined above, or (a''') $R_7$ is OH, X' is as defined above for X and $R_1$ is as defined above, directly after in situ activation analogously to methods such as are customary in peptide chemistry [Bodansky, M., Principles of Peptide Chemistry, 2nd Edition, 16–61, Springer Berlin (1993)], with a compound of the formula IX

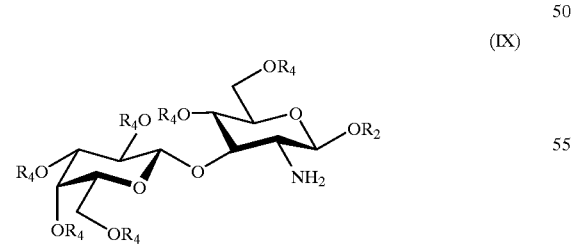

in which $R_2$ is as defined above and the individual $R_4$ independently of one another are hydrogen, acetyl, propionyl, butyryl or benzoyl, any acetyl, propionyl, butyryl or benzoyl groups present being split off with a basic alcohol solution, in which $R_1$, $R_2$, $R_3$ and X are as defined above, and (c) reacting the resulting product with a compound of the formula XI in the presence of fucose transferase to give a compound of the formula II.

The present invention furthermore relates to a process for the preparation of compounds of the formula II, which comprises (a) reacting a compound of the formula X with cytidine mono-phosphate-sialic acid in the presence of α(2→3) sialic acid transferase to give a compound of the formula VIII and (b) reacting the resulting product with a compound of the formula XI in the presence of fucose transferase to give a compound of the formula II.

With the enzymatic process according to the invention, it is possible for oligosaccharide structures to be prepared more efficiently compared with the chemical syntheses to date, and for highly modified, non-naturally occurring substrates to be glycosylated enzymatically in a highly regio- and stereoselective manner, it being possible for the compounds according to the invention to be prepared without the use of highly toxic heavy metal promoters (for example $Hg^{2+}$ salts), such as are usually employed in chemical glycosylations.

The compounds of the formulae IV, V and IX are known or can be prepared by known processes. The compounds of the formula IX can be synthesized by a process of Lemieux et al. and Boullanger et al. [Lemieux, R. U., Bundle, D. R., Baker, D. A., J. Am. Chem. Soc. 97:4076–4083 (1975); Boullanger, P., Banoub, J., Descotes, G., Can. J. Chem. 65:1343–1348 (1987)].

The amidation of compounds of the formulae IV and IX can be carried out in various way, depending on the definition of $R_1$, $R_7$ and X [Bodansky, M., Principles of Peptide Chemistry, 2nd Edition, 9–62, Springer Berlin (1993)].

For example, in case (a), $R_7$ is OH and X and $R_1$ are as defined above, the amidation can be carried out directly after the compounds of the formula V have first been activated with a diimidazole, for example carbonyldiimidazole (CDI), in a polar non-protic solvent, such as dimethylformamide (DMF) or acetonitrile.

(b) The amidation in the case of these compounds of the formulae IV and IX can also first be carried out after the aromatic OH groups have initially been protected, for example acetylated or benzoylated [McCorkindale, N. J., Roy, T. P., Hutchinson, S. A., Tetrahedron 2:1107–1111 (1972)]. The acid function can then be converted into the acid chloride with an inorganic acid chloride, for example thionyl chloride. These products are then coupled with the amine of the formula IV or IX in the presence of a base, for example triethylamine, in a solvent, such as methylene chloride, and the products are converted into the glucosamide derivatives of the formula VI or X by addition of a basic alcohol solution, for example methanol solution.

(c) Chlorides of the formula V which can undergo coupling, where $R_7$ is Cl, X is $C(O)$-$C_1$–$C_6$alkylene and $R_1$ is as defined above, are obtained by acetylating the aromatic OH groups of the corresponding carboxylic acid and initially reducing the free acid function to the benzylic OH groups by means of diborane [McCorkindale, N. J., Roy, T. P., Hutchinson, S. A., Tetrahedron 2:1107–1111 (1972)]. This product is reacted with phosgene to give the corresponding alkoxycarbonyl chloride of the formula V [Petersen, S. in: Müller, E. (Editor) Methoden der Organischen Chemie [Methods of Organic Chemistry] (Houben-Weyl) 8:102 (1952)].

After removal of the solvent, the amide derivatives of the formulae VI and X can be purified by chromatography, for example over silica gel (eluent: for example methylene chloride/methanol mixtures) and then lyophilized.

The enzymes used for the preparation of compounds of the formulae I and II are commercially obtainable or can be obtained by known processes. The galactose transferase used in the present case for the enzymatic p(1→4) galactosylation can be obtained, for example, from Boehringer. Exclusively β-specific galactosylation of the 4-OH function of the glucosamine takes place [Paicic, M. M., Methods Enzymol. 230:300–316 (1994)]. The galactose transferase used for the β(1→43)galactosylation can be produced, for example, by genetic engineering (JPN 06181759 A2, Application JP 92-336436921216). Exclusively galactosylation on the 3-OH function of the N-acylglucosamide takes place.

The α(2→3)sialic acid transferase is preferably a microbially produced sialyl transferase (WO 91/06635), the original site of occurrence is the rat liver. A strictly α-specific sialylation of the 3-OH group of the terminal galactose takes place.

The microbially produced fucose transferase VI (fuc-t VI) transfers the pyranose α-specifically to the 3-OH group of the N-acylglucosamine unit. The fucose transferase III (fuc-t III) also produced microbially transfers the pyranose α-specifically to the 4-OH group of the N-acylglucosamine unit (WO 91/12340).

The enzymatic reactions are advantageously carried out in the presence of 0.1 U to 5 U of the enzyme in question. It has proved favourable to employ the glycosyl donor in excess. Good results are achieved if, for example, 1.2 to 2 equivalents of uridine di-phosphategalactose, 1.2 to 2.3 equivalents of cytidine mono-phosphate-sialic acid or 1.2 to 2.5 equivalents of guanosine di-phosphate-fucose are employed.

The UDP-galactose can be obtained commercially or synthesized chemo-enzymatically. For this, hydroxyl-protective groups of the formula —C(O)—R of the sugar residue, in which R is linear or branched alkyl, preferably $C_1$–$C_8$alkyl, particularly preferably $C_1$–$C_4$alkyl, unsubstituted phenyl or phenyl which is substituted by $C_1$–$C_4$alkyl or $C_1$–$C_4$alkoxy, are split off enzymatically from a protected UDP-galactose. Examples of hydroxyl-protective groups are protective groups of the formula —C(O)—R, in which R is methyl, ethyl, n- or i-propyl, n-, i-, s- or t-butyl or pentyl, hexyl, heptyl or octyl with all the possible isomers, or is unsubstituted phenyl, or is phenyl which is mono- to trisubstituted in an identical or different manner with a substituent chosen from the group consisting of methyl, ethyl, n- and i-propyl, n-, i-, s- and t-butyl, methoxy, ethoxy, n- and i-propoxy and n-, i-, s- and t-butoxy. Examples of substituted phenyl are derived from toluene, o-, m- and p-xylene, pseudocumene, mesitylene, trimethylbenzene, ethylbenzene, dimethylpropylbenzene and cumene. This process can be carried out with soluble or immobilized enzymes. The choice of enzyme depends on the nature of the protective groups and the stereochemistry on the sugar. It has proved advantageous here to use a functionally homogeneous enzyme or an enzyme mixture. If the protective group is a radical —C(O)—$CH_3$, it is split off with an acetyl-esterase. If it is a radical —C(O)—$CH_2CH_3$, the protective group is split off with an acetyl-esterase, a lipase or a mixture of these two enzymes. Lipases are preferably employed for splitting off the radicals —C(O)-$C_3$–$C_8$alkyl and unsubstituted or substituted —C(O)-phenyl. The enzymes can originate from naturally occurring sources, such as animals, microorganisms or plants, or also produced by genetic engineering. Commercially obtainable enzymes, for example plant enzymes, such as the acetyl-esterase from orange peel (EC 3.1.1.6), are of particular advantage. The reaction can be carried out both in the presence and in the absence of buffers. If buffers are present, these are advantageously electrolytic buffers, such as NaCl, $MgHPO_4$, 2-morpholinoethanesulfonic acid monohydrate-NaOH, N-(2-acetamino)-2-aminoethanesulfonic acid NaOH-NaCl, 3-morpholinopropanesulfonic acid NaOH-NaCl, N-tris(hydroxymethyl)methyl-2-aminoethanesulfonic acid NaOH-NaCl, 4-(2-hydroxyethyl)piperazine-1-ethanesulfonic acid NaOH-NaCl and imidazole HCl-NaCl. The reaction is preferably carried out in a temperature range between room temperature and 40° C., preferably at 37° C. The pH is advantageously in a range between pH 6.5 and pH 7.5, and is preferably pH 7, and is advantageously kept constant automatically, for example with the aid of pH probes and automatic metering equipment. The choice of buffer, temperature and pH otherwise depend on the particular enzyme used and the substrate to be reacted and in individual cases it is entirely possible for it to lie outside the ranges stated. The process can also be carried out by activating either the sugar 1-phosphate or the corresponding nucleoside with a carbonyl-bis-azole before the coupling and, after the coupling, splitting off the protective groups enzymatically. Examples of carbonyl-bis-azoles are carbonyldiimidazole, carbonylditriazole, thiocarbonyldiimidazole and carbonyidioxydibenzotriazole. For example, protected monophosphoric acid sugar-esters are reacted with an excess of carbonyl-bis-azole in the presence of a polar solvent. The excess carbonyldiazole is then advantageously destroyed with a precisely metered amount of absolute methanol. After this activation, the activated sugar-phosphates are reacted in situ or after isolation with trialkylammonium salts of the nucleotide units to give the protected nucleoside di- or triphosphate-sugars. The imidazole salt primarily formed is then filtered over an ion exchanger, to be replaced by any ion Q. Further purification can then be carried out on reversed phase silica gels or by precipitation with suitable precipitants, such as ethanol or ethanol/isopropanol or ethanol/acetone mixtures. The reaction is advantageously carried out in the absence of water in a dry, polar, non-hydroxylic solvent in a temperature range between room temperature and 80° C., preferably in a range between 40° C. and 50° C., in particular at 40° C. It has proved advantageous to carry out the reaction in an ultrasonic bath. Examples of polar, non-hydroxylic solvents are dimethylformamide, dimethyl sulfoxide, acetone, dioxane, pyridine and acetonitrile and mixtures thereof.

The CMP-sialic acid donor where $R_3$ is methyl is commercially obtainable, but like the corresponding donor where $R_3$ is hydroxymethyl, can advantageously also be prepared enzymatically [Heidlas, J. E., Williams, K. W., Whitesides, G. M., Acc. Chem. Res. 25:307–314 (1992)].

The GDP-activated donor of the formula XI for the last preparation step can advantageously be prepared chemoenzymatically as described above for UDP-galactose.

The enzymatic transfer of galactose and sialic acid can be carried out both in a single step and in two successive steps.

The amidations can be carried out, depending on the definition of $R_1$, $R_2$, $R_4$, $R_7$ and X, in accordance with one of the customary specifications [for example Bodansky, M., Principles of Peptide Chemistry, 2nd Edition, 16–61, Springer Berlin (1993)]. For enzymatic syntheses with galactose transferase, sialic acid transferase and fucose transferase, it is advantageous to carry out the synthesis in the presence of buffers, such as sodium cacodylate, tris (hydroxymethyl)aminomethane or 4-(2-hydroxyethyl)-piperazine-1-ethanesulfonic acid, in each case in the optimum pH and temperature range, for example in the range from pH 6 to pH 8 and in the range from 25° C. to 37° C. It has proved particularly advantageous if the incubation mixture comprises salts, for example 5 to 40 mM manganese (II) chloride, and auxiliary enzymes, such as alkaline phosphatase from the bovine intestine (16 to 50 U).

The compounds according to the invention have an improved binding affinity for the corresponding selectins. The compounds according to the invention can be employed as antiadhesion therapeutics. In the case of pathogenic inflammations, they can prevent the selectin receptors from binding to activated endothelial cells on sialyl-Lewis$^a$ and/or sialyl-Lewis$^x$ structures on the surface of leucocytes. In the case of tissue rejections, they can block corresponding receptors of the haematolymphoid cell system. The adhesion of metastasing cells, bacteria, viruses or other pathogens and toxins can likewise be suppressed by blocking the corresponding receptors on the cell surface.

The invention also additionally relates to the compounds according to the invention for use in a therapeutic method for the treatment of diseases in warm-blooded animals, including man. The dosage on administration to warm-blooded animals of about 70 kg body weight can be, for example, 0.01 to 1000 mg per day. The compounds are preferably administered parenterally, for example intravenously or intraperitoneally, in the form of pharmaceutical preparations.

The invention furthermore relates to a pharmaceutical preparation comprising an active amount of compound according to the invention, by itself or together with other active ingredients, a pharmaceutical carrier, preferably in a significant amount, and, if appropriate, adjuncts.

The pharmacologically active compounds according to the invention can be used in any form of preparations for parenteral administration or infusion solutions. Such solutions are preferably isotonic aqueous solutions or suspensions, it being possible for these to be prepared before use, for example in the case of lyophilized preparations which comprise the active substance by itself or together with a carrier, for example mannitol. The pharmaceutical preparations can be sterilized and/or comprise adjuncts, for example preservatives, stabilizers, wetting agents and/or emulsifiers, solubilizing agents, salts for regulating the osmotic pressure and/or buffers. The pharmaceutical preparations, which can comprise further pharmacologically active substances, for example antibiotics, if desired, are prepared in a manner known per se, for example by means of conventional dissolving or lyophilizing processes, and comprise about 0.1% to 90%, in particular from about 0.5% to about 30%, for example 1% to 5%, of active substance(s).

The following Examples illustrate the invention in more detail.

Abbreviations: Ac: acetyl; CMP-sia: cytidine monophosphate-sialic acid; DMF: dimethylformamide; DMSO: dimethyl sulfoxide; DPPB: 1,4-bis (diphenylphosphino)butane; GDP-ara: guanosine diphosphate-α-D-arabinose; GDP-L-gal: guanosine diphosphate-L-galactose; HBPyU: O-(benzotriazol-1-yl)-N,N,N',N'-bis(tetramethylene)uronium hexafluorophosphate; Ph: phenyl; BSA: bovine serum albumin (Boehringer); RT: room temperature; TBTU: O-(benzotriazol-1-yl)-N,N,N',N'-tetramethyluronium tetrafluoroborate; THF: tetrahydrofuran; UDP-gal: uridine diphosphate-D-galactose All enzymatic steps are performed in plastic vessels.

A PREPARATION OF THE STARTING COMPOUNDS

EXAMPLE A1

Preparation of Compound No. (54)

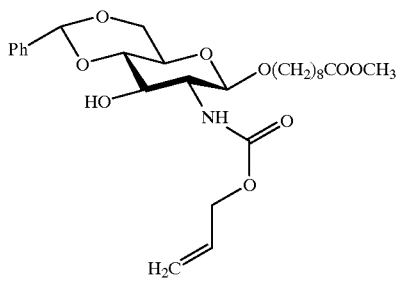

(54)

(a) 8.63 g (20.0 mmol) of α,β-1,3,4,6-tetra-O-acetyl-2-deoxy-2-N-allyloxycarbonyl-glucose [Boullanger, P., Jouineau, M., Bouammali, B., Lafont, D., Descotes, G., Carbohydr. Res. 202:151–164 (1990)] are reacted by known processes [Lafont, D., Manaudier, S., Boullanger, P., Descotes, G., Bull. Soc. Chim. Fr. 127:576–583 (1990)] with 5.65 g (30.0 mmol) of methyl 9-hydroxy-nonanecarboxylate [Lemieux, R. U., Bundle, D. R., Baker, D. A., J. Am. Chem. Soc. 97:4076–4083 (1975)] in the presence of 10.3 ml (56.0 mmol) of methyl trifluoromethanesulfonate at −30° C. in 150 ml of methylene chloride. After chromatography of the reaction mixture on silica gel (eluent: petroleum ether/ethyl acetate—2/1), 11.14 g (quantitative) of compound No. (17) are obtained.

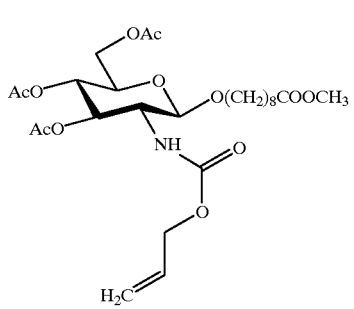

(17)

(b) 5.15 g (9.2 mmol) of monosaccharide No. (17) are added to 30 ml of dry methanol, in which 15.0 mg (0.65 mmol) of sodium has been dissolved beforehand, at RT under an argon atmosphere. After about 1 h, the sugar is deacetylated completely. The reaction mixture is then poured onto a strongly acid ion exchanger (DOWEX 8×50 strongly acidic, Fluka), the mixture is shaken for 15 minutes, the ion exchanger is filtered off and washed again with about 100 ml of methanol and the combined organic phases are evaporated. The resulting white powder is dried under a high vacuum. 3.95 g (99%) of deprotected sugar No. (11) are obtained [(Öhrlein, R., Ernst, B., Berger, E. G., Carbohydr. Res. 236:335–338 (1992)].

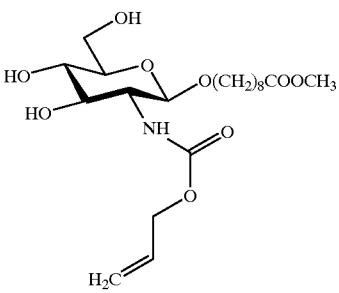

(11)

$^1$H-NMR (CD$_3$OD, 250.13 MHz) δ=1.22 (m, 8 H); 1.47 (m, 4 H); 2.22 (t, 7.6 Hz, 2 H); 3.19–3.43 (m, 5 H); 3.55 (s, 3 H); 3.60 (dd, 5.5 Hz, 10.3 Hz, 1 H); 3.78 (m, 2 H); 4.25 (d, 7.3 Hz, 1 H); 4.42 (m, 2 H); 5.10 (broad d, 17.2 Hz, 1 H); 5.23 (broad d, 17.2 Hz, 1 H); 5.86 (m, 1 H). $^{13}$C-NMR (CD$_3$OD, 62.90 MHz) δ=26.00; 27.01; 30.11; 30.31; 30.34; 30.62; 34.77; 51.98; 59.00; 62.79; 66.36; 70.66; 72.13; 75.93; 77.81; 103.11; 117.30; 134.49; 158.88; 175.97.

(c) 9.7 g (22.4 mmol) of monosaccharide No. (11) are dissolved in 100 ml of dry THF. 6 ml (40.0 mmol) of benzaldehyde dimethylacetal and 250 mg of racemic camphor-10-sulfonic acid are added to this solution in succession and the mixture is heated to 50° C. It is stirred overnight until all the starting material has been consumed and is then cooled to RT and, before the solvent is evaporated off, a further 0.5 ml of triethylamine is added. The residue is chromatographed over silica gel (eluent: methylene chloride/methanol—20/1). 11.0 g (95%) of 4,6-protected sugar No. (54) are obtained. $^1$H-NMR (CDCl$_3$, 400.13 MHz) δ=1.20 (m, 8 H); 1.51 (m, 4 H); 2.23 (t, 7.6 Hz, 2 H); 3.25–3.50 (m, 5 H); 3.60 (s, 3 H); 3.70 (t, 9.7 Hz, 1 H); 3.78 (dt, 4.8 Hz, 9.7 Hz, 1 H); 4.25 (dd, 4.8 Hz, 10.9 Hz, 1 H); 4.50 (m, 2 H); 5.12 (m, 2 H); 5.23 (dq, 1.2 Hz, 16.3 Hz, 1 H); 5.45 (s, 1 H); 5.84 (m, 1 H); 7.30 (m, 3 H); 7.42 (m, 2 H). $^{13}$C-NMR (CDCl$_3$, 100.61 MHz) δ=24.77; 25.63; 28.91; 29.00; 29.35; 34.16; 51.46; 58.60; 65.73; 66.04; 68.59; 70.21; 70.69; 72.27; 81.49; 101.75; 117.60; 126.21 (2×C); 128.23 (2×C); 129.17; 132.46; 159.16; 174.53.

EXAMPLE A2

Preparation of Compound No. (3)

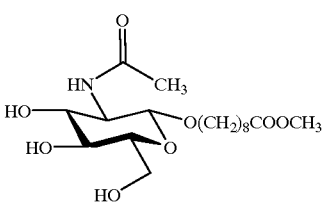

(3)

(a) 13.1 g (82%) of amine No. (2) are obtained as a white powder from 20.0 g (46 mmol) of monosaccharide No. (11) in the presence of 0.9 g of tetrakis-triphenylpalladium, 0.9 g of DPPB and 11.9 g (82.9 mmol) of sodium thiophenolate in dioxane/methanol/THF (200 ml–40 ml–100 ml) analogously to known processes [Boullanger, P., Banoub, J., Descotes, G., Can. J. Chem. 65:1343–1348 (1987) or Genêt, J. P., Blart, E., Savignac, M., Lemeune, S., Lemaire-Audoire, S., Bernard, J. M., Synlett 680–682 (1993)] after chromatography of the reaction mixture over silica gel (eluent: methylene chloride/methanol—7/1).

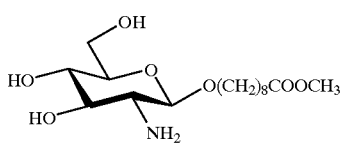

(2)

$^1$H-NMR (CD$_3$OD, 62.90 MHz) δ=1.25 (m, 8 H); 1.51 (m, 4 H); 2.23 (t, 8.4 Hz 2 H); 2.50 (bd, 8.3 Hz, 1 H); 3.19 (m, 3 H); 3.41 (dt, 4.2 Hz, 8.4 Hz, 1 H); 3.57 (s, 3 H); 3.59 (bdd, 4.8 Hz, 12.4 Hz, 1 H); 3.71 (m, 2 H); 4.13 (d, 7.6 Hz, 1 H).

(b) 3.35 g (9.6 mmol) of compound No. (2) are dissolved in 90 ml of methanol at RT, 1.09 ml of acetic anhydride and 1.60 ml of triethylamine are added in succession and the mixture is stirred overnight at RT. The reaction mixture is evaporated and the residue is chromatographed over silica gel (eluent: methylene chloride/methanol—7/1). 3.75 g of compound No. (3) are obtained as a white powder. $^1$H-NMR (CD$_3$OD, 250.13 MHz) δ=1.22 (m, 8 H); 1.49 (m, 4 H); 1.89 (s, 3 H); 2.22 (t, 7.6 Hz, 2 H); 3.18–3.86 (m, 10 H); 4.31 (d, 7.6 Hz, 1 H). $^{13}$C-NMR (CD$_3$OD, 62.98 MHz) δ=23.75; 26.70; 27.72; 30.82; 30.99 (2×C); 31.08; 31.30; 35.47; 52.69; 58.05; 63.47; 71.28; 72.81; 77.78; 78.57; 103.37; 174.13.

EXAMPLE A3

Preparation of Compound No. (16)

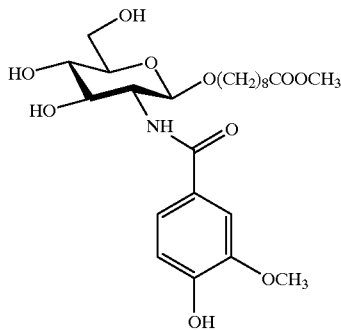

(16)

(a) 36 mg (214 μmol) of vanillic acid are introduced into 3 ml of dry DMF, and 30 μl (216 μmol) of triethylamine and 91 mg (211 μmol) of TBTU are added at RT [Dourtoglou, V., Gross, B., Lambropoulou, V., Zioudrou, C., Synthesis 572–574 (1984)]. 100 g (286 μmol) of amine No. (2) are added to the resulting clear solution and the mixture is stirred overnight. After the solvent has been evaporated off and the residue has been chromatographed over RP-18 gel (eluent: methanol/water—1/1), 41 mg (41%) of compound No. (16) are obtained as a white powder after lyophilization from dioxane. $^1$H-NMR (CD$_3$OD-CDCl$_3$, 250.13 MHz) δ=1.10 (m, 8 H); 1.46 (m, 4 H); 2.22 (t, 7.5 Hz, 2 H); 3.40–3.92 (m, 14 H); 4.59 (d, 8.2 Hz, 1 H); 6.82 (d, 8.3 Hz, 1 H); 7.36 (dd, 2.1 Hz, 8.3 Hz, 1H); 7.44 (d, 2.1 Hz, 1 H); $^{13}$C-NMR (CD$_3$OD-CDCl$_3$, 62.90 MHz) δ=25.78; 26.90; 29.90; 30.13 (2×C); 30.45; 34.76; 52.14; 56.46; 57.70; 62.90; 70.67; 72.11; 76.06; 77.32; 102.12; 111.96; 115.59; 121.88; 127.24; 150.14; 151.49; 167.68; 170.74.

(b1) 3.9 g (76%) of free amine No. (18) are obtained in accordance with the instructions by Boullanger et al. [Boullanger, P., Banoub, J., Descotes, G., Can. J. Chem. 65:1343–1348 (1987)] or Genêt et al. [Genêt, J. P., Blart, E., Savignac, M., Lemeune, S., Lemaire-Audoire, S., Bernard, J. M., Synlett 680–682 (1993)] from 6.0 g (10.7 mmol) of compound No. (17).

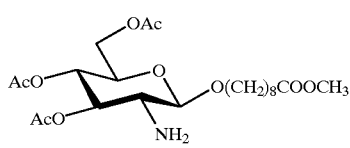

(18)

$^1$H-NMR (CD$_3$OD, 250.13 MHz) δ=1.34 (m, 8 H); 1.64 (m, 4 H); 2.06 (s, 3 H); 2.11 (s, 6 H); 2.33 (t, 7.6 Hz, 2 H); 2.95 (dd, 2.1 Hz, 8.3 Hz, 1 H); 3.52 (dt, 7.6 Hz, 8.3 Hz, 1 H); 3.71 (m, 4 H); 3.93 (dt, 7.6 Hz, 8.3 Hz, 1 H); 4.15 (dd, 2.1 Hz, 11.0 Hz, 1 H); 4.28 (d, 7.3 Hz, 1 H); 4.72 (dd, 5.5 Hz, 11.0 Hz, 1 H); 5.02 (m, 2 H). $^{13}$C-NMR (CDCl$_3$, 62.90 MHz) δ=20.17; 20.25; 20.31; 24.37; 25.37; 28.51; 28.63 (2×C); 28.99; 33.48; 50.90; 55.48; 61.82; 68.47; 69.74; 71.26; 74.90; 103.57; 169.22; 170.06; 173.59.

(b2) 100 mg (210 mmol) of amine No. (18), 47 mg (280 mmol) of vanillic acid and 121 mg (280 mmol) of HBPyU are dissolved in 3 ml of absolute acetonitrile at room temperature, 31 μl of triethylamine are then added and the mixture is stirred for three days. After the solvent has been evaporated off and the residue has been chromatographed over silica gel (eluent: petroleum ether/ethyl acetate—1/3), 84 mg (64%) of peracetylated amide are obtained; the product is dissolved in 2 ml of dry methanol at RT, and 308 μmol of freshly prepared sodium methanolate are added. After about 4 hours, the mixture is neutralized with DOWEX 50×8 H$^+$ form, the resin is filtered off and the mixture is evaporated. The residue is chromatographed over silica gel and the desired product is lyophilized from dioxane/water. 37 mg (65%) of amide No. (16) are obtained as a white powder.

EXAMPLE A4

Preparation of Compound No. (23)

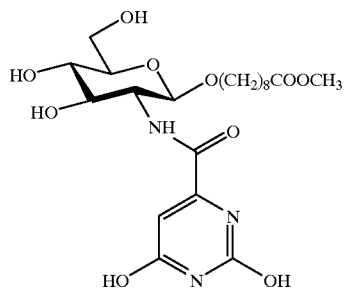
(23)

82 mg (526 μmol) of orotic acid are suspended in 5 ml of dry DMF. 74 μl of triethylamine, 227 mg (527 μmol) of TBTU and 250 mg (716 mmol) of amine No. (2) are added in succession under argon, with vigorous stirring. After purification by chromatography twice, first over silica gel (eluent: methylene chloride/methanol—10/2) and then over reversed phase gel (eluent: methanol/water—1/1), 123 mg (48%) of amide No. (23) are obtained as a white powder after lyophilization from dioxane/water. $^1$H-NMR (D$_6$-DMSO, 250.13 MHz) δ=1.28 (m, 8 H); 1.45 (m, 4 H); 2.26 (t, 7.5 Hz, 2 H); 3.14 (m, 2 H); 3.43 (m, 4 H); 3.59 (s, 3 H); 3.70 (m, 2 H); 4.39 (d, 8.2 Hz, 2 H); 6.11 (s, 1 H); 8.68 (broad d, 9.6 Hz, 1 H). $^{13}$C-NMR (D$_6$-DMSO, 62.89 MHz) δ=25.12; 26.21; 29.15; 29.41; 29.48; 29.70; 33.96; 51.87; 56.79; 61.56; 69.20; 71.07; 74.31; 77.71; 99.97; 101.33; 147.17; 153.16; 160.98; 165.20; 174.11.

EXAMPLE A5

Preparation of Compound No. (49)

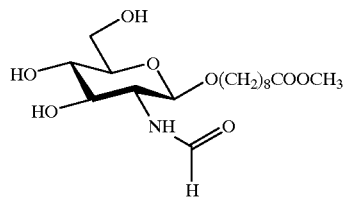
(49)

335 μl of methyl formate are added to 40 mg (114 μmol) of amine No. (2) in 1 ml of methanol and a catalytic amount of triethylamine, and the mixture is heated at 50° C. for 2 days. After the mixture has been concentrated, the residue is chromatographed over silica gel (eluent: methylene chloride/methanol—10/2). 39 mg (91%) of formamide No. (49) are obtained as an isomer mixture (about 60/40). $^1$H-NMR (CD$_3$OD, 250.13 MHz) δ=1.21 (m, 8 H); 1.49 (m, 4 H); 2.22 (t, 7.6 Hz, 2 H); 2.92–3.45 (m, 5 H); 3.52–3.64 (m, 4 H); 3.74–3.89 (m, 2 H); 4.22 (d, 8.5 Hz, 0.4 H); 4.35 (d, 8.5 Hz, 0.6 H); 7.85 (s, 0.4 H); 8.05 (s, 0.6 H). M: main isomer; S: secondary isomer; $^{13}$C-NMR (CD$_3$OD, 62.90 MHz) δ=25.99; 26.99; 30.09; 30.26; 30.33; 30.58; 34.76; 51.98; 56.31 M; 60.71 S; 62.59 S; 62.71 M; 70.59 M; 70.83 S; 71.89 S; 72.02 M; 75.38 S; 75.80 M; 77.76 S; 77.91 M; 102.30 S; 102.42 M; 164.12 M; 168.14 S; 176.02.

EXAMPLE A6

Preparation of Compound No. (78)

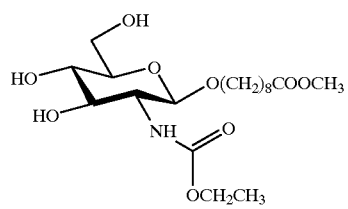
(78)

1.25 g (36 mmol) of amine No. (2) are dissolved in 45 ml of absolute methylene chloride at RT, and 310 μl (33 mmol) of ethyl chloroformate and 45 μl of triethylamine are added in succession. After about 5 hours, the reaction mixture is evaporated and the residue is chromatographed over silica gel (eluent: methylene chloride/methanol—15/2). 950 mg (69%) of monosaccharide No. (78) are obtained. $^1$H-NMR (CD$_3$OD, 250.13 MHz) δ=1.18 (t, 7.5 Hz, 3 H); 1.25 (m, 8 H); 1.49 (m, 4 H); 2.23(t, 7.6 Hz, 2 H); 3.10–3.46 (m, 5 H); 3.57 (s, 3 H); 3.60 (dd, 5.5 Hz, 10.0 Hz, 1 H); 3.74–3.88 (m, 2 H); 4.00 (q, 7.5 Hz, 2 H); 4.26 (broad d, 8.6 Hz, 1 H). $^{13}$C-NMR (CD$_3$OD, 62.9 Mhz) DEPT δ=14.37; 25.33; 26.31; 29.43; 29.62; 29.67; 29.93; 34.10; 51.35; 58.21; 61.06; 62.08; 70.02; 71.42; 75.25; 77.11; 102.48.

EXAMPLE A7

Preparation of Compound No. (95)

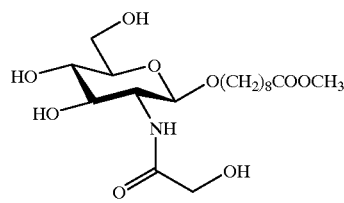
(95)

(a) 1.3 g (3.7 mmol) of amine No. (2) are dissolved in 20 ml of methanol at RT, and 1.0 ml (6.1 mmol) of triethylamine and 0.8 ml (5.2 mmol) of benzyloxyacetyl chloride are added in succession and the mixture is stirred overnight. The solvent is now evaporated off and the residue is chromatographed over silica gel (eluent: methylene chloride/methanol—9/1). 1.6 g (85%) of amide No. (94) are obtained.

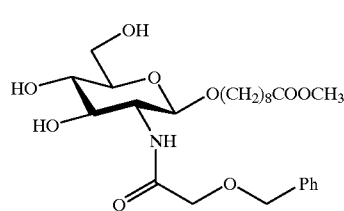
(94)

$^1$H-NMR (CD$_3$OD, 250.13 MHz) δ=1.21 (m, 8 H); 1.48 (m, 4 H); 2.21 (t, 7.5 Hz, 2 H); 3.23 (m, 2 H); 3.39 (dt, 6.9 Hz, 9.0 Hz, 1 H); 3.47–3.70 (m, 6 H); 3.81 (m, 2 H); 3.91

(m, 2 H); 4.44 (d, 8.6 Hz, 1 H); 4.56 (s, 2 H); 7.30 (m, 5 H). $^{13}$C-NMR (CD$_3$OD, 62.9 MHz) δ=25.97; 27.02; 30.09; 30.28; 30.31; 30.62; 34.75; 51.97; 57.11; 62.79; 70.23; 70.52; 72.22; 74.22; 75.61; 77.87; 102.36; 129.09; 129.15; 129.53; 136.64; 172.81; 175.89.

(b) 1.6 g (3.2 mmol) of compound No. (94) are dissolved in 50 ml of methanol at RT to give a clear solution, and 200 mg of 10% palladium-on-charcoal are added under an argon atmosphere. Hydrogen is passed through this mixture, with vigorous stirring, until no further deduct is detectable. The charcoal is now filtered off over Celite, the solvent is evaporated and the residue which remains is dried under a high vacuum. 1.2 g (91%) of monosaccharide No. (95) are obtained as a colourless solid. $^1$H-NMR (CD$_3$OD, 250.13 MHz) δ=1.25 (m, 8 H); 1.49 (m, 4 H); 2.22 (t, 7.5 Hz, 2 H); 3.16–3.45 (m, 9 H); 3.71–3.81 (m, 2 H); 3.92 (m, 2 H); 4.40 (d, 8.6 Hz, 1 H). $^{13}$C-NMR (CD$_3$OD, 62.9 MHz) δ=26.00; 26.97; 30.10; 30.29 (2×C); 30.61; 34.78; 51.96; 57.10; 62.73; 62.81; 70.56; 72.22; 75.78; 77.87; 102.45; 175.55; 176.05.

EXAMPLE A8

Preparation of Compound No. (28)

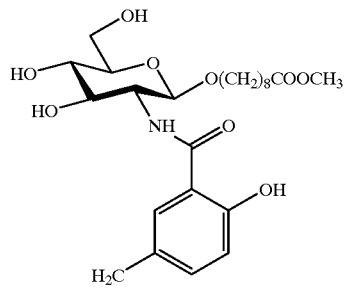

(28)

65 mg (64%) of monosaccharide No. (28) are obtained from 31 mg (204 μmol) of 2-hydroxy-5-methylbenzoic acid and 100 mg (210 μmol) of amine No. (18) in the presence of 95 mg (220 μmol) of HBPyU in 3 ml of dry acetonitrile. $^1$H-NMR (CD$_3$OD, 250.13 MHz) δ=1.03 m, 8 H); 1.39 (m, 4 H); 2.15 (t, 7.6 Hz, 2 H); 2.21 (s, 3 H); 3.23–3.44 (m, 3 H); 3.57 (s, 3 H); 3.62 (m, 2 H); 3.81 (m, 3 H); 4.50 (d, 7.6 Hz, 1 H); 6.71 (d, 7.6 Hz, 1 H); 7.10 (dd, 1.4 Hz, 7.6 Hz, 1 H); 7.53 (d, 1.4 Hz, 1 H). $^{13}$C-NMR (CD$_3$OD, 62.90 MHz) δ=20.62; 25.79; 26.90; 29.86; 30.03; 30.09; 30.38; 34.68; 51.94; 57.15; 62.64; 70.60; 72.07; 75.42; 77.60; 102.54; 116.22; 118.21; 128.34; 128.91; 135.41; 159.18; 171.62; 175.91.

EXAMPLE A9

Preparation of Compound No. (33)

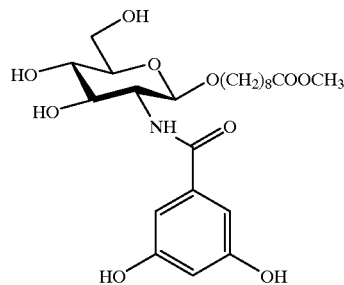

(33)

86 mg (84%) of compound No. (33) are obtained according to Example A8 from 37 mg (240 μmol) of 3,5-dihydroxybenzoic acid and 100 mg (210 μmol) of compound No. (18) in the presence of 104 mg (240 μmol) of HBPyU. $^1$H-NMR (CD$_3$OD, 250.13 MHz) δ=1.17 (m, 8 H); 1.49 (m, 4 H); 2.16 (t, 7.5 Hz, 2 H); 3.34–3.55 (m, 3 H); 3.59–3.96 (m, 8 H); 4.55 (d, 8.6 Hz, 1 H); 6.43 (t, about 2.0 Hz, 1 H); 6.76 (d, about 2.0 Hz, 2 H). $^{13}$C-NMR (CD$_3$OD, 62.90 MHz) δ=25.97; 27.15; 30.07; 30.26; 30.30; 30.54; 34.78; 51.94; 57.92; 62.54; 70.70; 72.31; 75.70; 77.92; 102.78; 106.64; 107.19 (2×C); 138.15; 159.72 (2×C); 169.66; 176.22.

EXAMPLE A10

Preparation of Compound No. (37a)

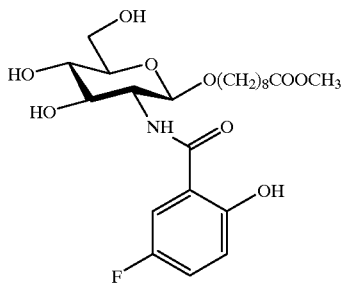

(37a)

47 mg (47%) of monosaccharide No. (37a) are obtained according to Example A8 from 34 mg (220 μmol) of 3-fluoro-6-hydroxybenzoic acid and 100 mg (210 μmol) of amine No. (18). $^1$H-NMR (CD$_3$OD-CDCl$_3$, 250.13 MHz) δ=1.09 (m, 8 H); 1.45 (m, 4 H); 2.21 (t, 7.6 Hz, 2 H); 3.33–3.89 (m, 11 H); 4.54 (d, 7.6 Hz, 1 H); 6.84 (dd, 5.5 Hz, 10.3 Hz, 1 H); 7.02 (ddd, 3.4 Hz, 7.6 Hz, 8.3 Hz, 1 H); 7.42 (dd, 5.5 Hz, 10.3 Hz, 1 H). $^{13}$C-NMR (CD$_3$OD-CDCl$_3$, 62.90 MHz) δ=24.61; 25.57; 28.72; 28.82; 28.85; 29.15; 33.84; 51.37; 55.84; 61.26; 70.07; 70.58; 74.03; 75.27; 100.94; 112.97 (d, 24.2 Hz); 115.24 (d, 6.5 Hz); 118.69; 120.90 (d, 23.4 Hz); 155.11 (d, 174.2 Hz); 169.40; 174.80. $^{19}$F-NMR (CD$_3$OD-CDCl$_3$, 235.36 MHz) δ=−73.36.

EXAMPLE A11

Preparation of Compound No. (41)

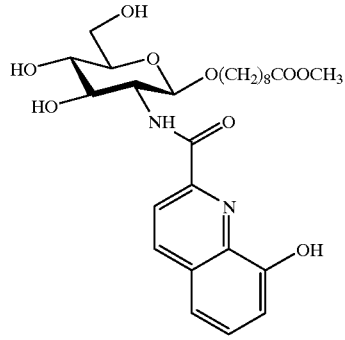

(41)

47 mg (47%) of monosaccharide No. (41) are obtained according to Example A8 from 42 mg (220 μmol) of 8-hydroxy-quinoline-2-carboxylic acid and 100 mg (210 μmol) of amine No. (18) after deacetylation with 1.05 equivalents of sodium methanolate. $^1$H-NMR (CD$_3$OD, 250.13 MHz) δ=0.38–1.40 (m, 12 H); 1.92 (t, 7.6 Hz, 2 H); 3.28–3.92 (m, 11 H); 4.48 (d, 7.6 Hz, 1 H); 7.09 (dd, 0.9 Hz, 7.6 Hz, 1 H); 7.34 (dd, 0.9 Hz, 7.6 Hz, 1 H); 7.47 (t, 7.6 Hz, 1 H); 8.12 (d, 8.3 Hz, 1 H); 8.31 (d, 8.3 Hz, 1 H). $^{13}$C-NMR (CD$_3$OD, 62.90 MHz) δ=26.52; 27.09; 29.89; 30.17; 30.22; 30.50; 34.64; 51.92; 57.81; 62.82; 70.61; 72.23; 75.94; 78.05; 102.88; 112.78; 118.99; 120.15; 130.57; 131.46; 138.34; 138.82; 148.89; 155.02; 167.04; 175.87.

EXAMPLE A12

Preparation of Compound No. (45)

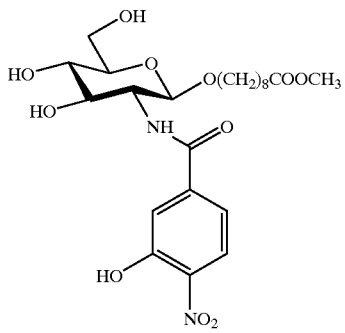

(45)

97 mg (82%) of monosaccharide No. (45) are obtained according to Example A8 from 44 mg (240 μmol) of 3-hydroxy-4-nitrobenzoic acid and 110 mg (231 μmol) of amine No. (18) in the presence of 100 mg of HBPyU and 31 μl of triethylamine. $^1$H-NMR (CD$_3$OD-CDCl$_3$, 250.13 MHz) δ=1.22 (m, 8 H); 1.59 (m, 4 H); 2.35 (t, 7.6 Hz, 2 H); 3.39–3.65 (m, 3 H); 3.71–4.07 (m, 8 H); 4.70 (d, 7.6 Hz, 1 H); 7.53 (dd, 2.1 Hz, 8.3 Hz, 1 H); 7.70 (d, 2.1 Hz, 1 H); 8.23 (d, 8.3 Hz, 1 H). $^{13}$C-NMR (CD$_3$OD-CDCl$_3$, 62.90 MHz) δ=25.55; 29.67; 29.86 (2×C); 30.12; 34.69; 52.30; 57.41; 61.90; 70.84; 71.19; 74.59; 76.93; 102.02; 119.48; 119.77; 126.29; 136.53; 143.03; 154.68; 167.82; 176.04.

PREPERATION OF THE MIMETICS

EXAMPLE B1.1

Preparation of Compound No. (10)

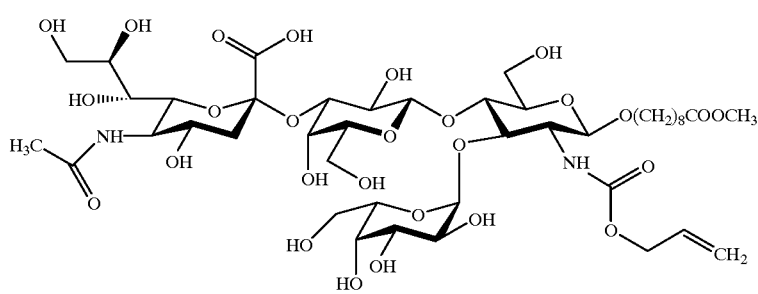

(10)

(a1) Galactosylation with β(1→4)galactose transferase 512.0 mg (24.7 μmol) of compound No. (11), 31.5 μmol of UDP-gal, 1.4 mg of BSA and 16.9 mg (85 μmol) of manganese(II) chloride hexahydrate are brought together in 1.0 ml of sodium cacodylate buffer (0.1 M, pH=7.43) and the mixture is briefly treated with ultrasound in an ultrasonic bath. 0.2 U of galactose transferase (Sigma; 0.2 ml) and 34 U (2 μl) of alkaline phosphatase from the bovine intestine (Boehringer) are added to the resulting homogeneous, milky suspension. The mixture is mixed and incubated at 37° C., while stirring. The reaction precipitates are centrifuged off, the clear supernatant is lyophilized from water/dioxane and the residue is purified by chromatography over silica gel (eluent: methylene chloride/methanol/water mixtures). The solvent is removed, the residue is taken up in dioxane/water and renewed lyophilization gives 17.5 mg of compound No. (12) (100%) as a white powder.

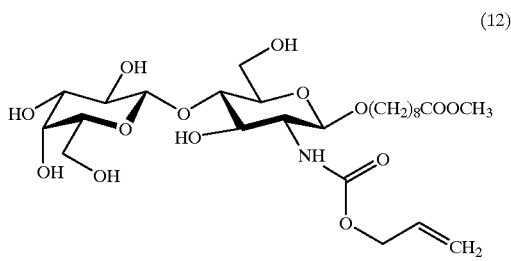

(12)

(a2) Galactosylation with β(1→4)galactose transferase and UDP-galactose epimerase 1.18 mmol of compound No. (11), 1.40 mmol of uridine diphosphate-glucose (UDP-glc) (Sigma), 8.9 mg of BSA and 64.0 mg (323 μmol) of manganese(II) chloride hexahydrate (Fluka) are brought together in 8 ml of sodium cacodylate buffer (0.1 M, pH=7.52) and the mixture is briefly treated with ultrasound in an ultrasonic bath. 24 U of galactosyl transferase (6 ml), 800 μl of UDP-galactose epimerase (Sigma, 100 U/2 ml) and 129 U (8 μl) of alkaline phosphatase from the bovine intestine (Boehringer) are added to the resulting homogeneous, milky suspension. The mixture is mixed and incubated at 37° C., while stirring. At the end of the reaction, the reaction precipitates are centrifuged off, the clear supernatant is lyophilized from water/dioxane and the residue is purified by chromatography over silica gel (eluent: methylene chloride/methanol/water mixtures). The solvent is removed, the residue is taken up in dioxane/water and renewed lyophilization gives 621 mg (88%) of compound No. (12) as a white powder. $^1$H-NMR (CD$_3$OD-CDCl$_3$, 250.13 MHz) δ=1.22 (m, 8 H); 1.48 (m, 4 H); 2.21 (t, 7.5 Hz, 2 H); 3.24–3.85 (m, 17 H); 4.29 (broad d, 8.6 Hz, 2 H); 4.44 (m, 2H); 5.08 (dd, 10.3 Hz, 1.4 Hz, 1 H); 5.23 (broad d, 15.1 Hz, 1 H); 5.82 (m, 1 H). $^{13}$C-NMR (CD$_3$OD-CDCl$_3$, 62.89 MHz) δ=25.85; 26.83; 29.97; 30.15; 30.19; 30.45; 34.69; 51.96; 58.22; 61.84; 62.38; 66.25; 70.11; 70.65; 72.41; 73.99; 74.58; 76.17; 76.89; 80.91; 102.91; 104.85; 117.28; 134.26; 158.52; 175.86.

(b) Sialidation with α(2→3) sialic acid transferase 202 mg (339 μmol) of compound No. (12) are added to a mixture of 3 ml of a manganeses(II) chloride solution (0.06 M), 3 ml of sodium cacodylate buffer (0.05 M, pH=6.5) and 2.0 ml of doubly distilled water in a plastic test tube. The mixture is briefly treated with ultrasound in an ultrasonic bath. 329 mg (499 μmol) of CMP-sia (content about 90%), 3.5 mg of BSA, 300 μl (2.1 U) of sialyl-transferase and 4 μl (64 U) of alkaline phosphatase from the bovine intestine (Boehringer) are then added, the components are mixed and the mixture is incubated at 37° C., while stirring. At the end of the reaction, the reaction precipitates are centrifuged off. The clear supernatant is filtered over a reversed phase C-18 column (eluent: methanol) and then purified over a silica gel column (eluent: methylene chloride/methanol/water mixtures). The solvent is removed, the residue is taken up in dioxane/water and the product is lyophilized. 186 mg of compound No. (13) (72%) are obtained as a white powder.

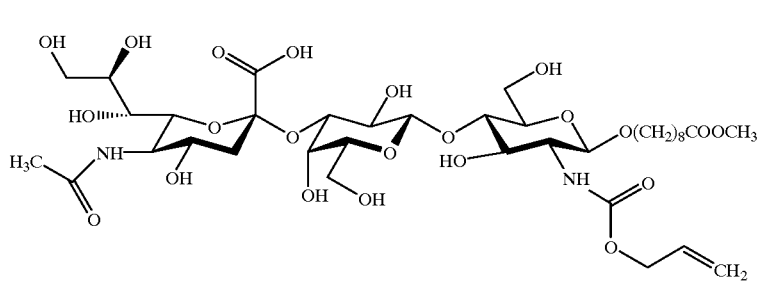

(13)

$^1$H-NMR (CD$_3$OD, 250.13 MHz) δ=1.20 (m, 8 H); 1.44 (m, 4 H); 1.68 (broad t, 11. 6 Hz, 1 H); 1.92 (s, 3 H); 2.19 (t, 7.6 Hz, 2 H); 2.70 (dd, 11.6 Hz, 2.8 Hz, 1 H); 3.21–3.88 (m, 23 H); 3.93 (dd, 10.3 Hz, 2.1 Hz, 1 H); 4.25 (broad d, 8.3 Hz, 1 H); 4.35 (broad d, 8.4 Hz, 1 H); 4.42 (m, 2 H); 5.06 (m, 1 H); 5.20 (m, 1 H); 5.81 (m, 1 H). $^{13}$C-NMR (CD$_3$OD, 62.98 MHz) δ=22.66; 26.01; 26.99; 30.12; 30.29; 30.33; 30.62; 34.79; 41.95; 51.96; 53.97; 58.44; 62.04; 62.73; 64.42; 66.37; 69.11; 69.28; 70.03; 70.78; 70.85; 72.96; 74.27; 74.92; 76.42; 77.02; 77.61; 81.30; 101.13; 103.18; 104.99; 117.27; 134.51; 158.83; 175.05; 175.49; 176.53.

(c) Fucosylation with fucose transferase VI 23.3 mg (26.2 μmol) of compound No. (13), 25.0 mg (38.5 μmol) of GDP-gal and 1.3 mg of BSA are added to a mixture of 150 μl of manganese(II) chloride solution (0.25 M), 450 μl of sodium cacodylate buffer (0.25 M, pH=6.48) and 600 μl of double-distilled water. 2 μl (32 U) of alkaline phosphatase from the bovine intestine (Boehringer) and 250 μl (500 mU) of a fucose transferase VI solution are added, the components are mixed and the mixture is incubated at 37° C., while stirring. At the end of the reaction, the reaction precipitates are centrifuged off and the clear supernatant is passed over a reversed phase C-18 column (eluent: methanol). The product-containing fractions are lyophilized from water/dioxane, filtered over an Na$^+$ column (Dowex) and lyophilized again. Finally, the residue is purified over a silica gel column (eluent: methylene chloride/methanol/water mixtures) and lyophilized again from water/dioxane. 18 mg of compound No. (10) (66%) are obtained as a white powder. $^1$H-NMR (CD$_3$OD, 250.13 MHz) δ=1.24 (m, 8 H); 1.49 (m, 4 H); 1.66 (broad t, 12.4 Hz, 1 H); 1.96 (s, 3 H); 2.24 (t, 8.4 Hz, 2 H); 2.78 (dd, 12.4 Hz, 3.4 Hz, 1 H); 3.27–3.93 (m, 29 H); 4.00 (dd, 10.3 Hz, 2.1 Hz, 1 H); 4.31 (d, 8.3 Hz, 1 H); 4.48 (m, 3 H); 4.71 (t, 6.2 Hz, 1 H); 5.11 (m, 1 H); 5.23 (m, 1 H); 5.88 (m, 1 H). $^{13}$C-NMR (CD$_3$OD, 100.62 MHz) δ=22.6; 26.0; 27.0; 30.1; 30.3; 30.4; 30.6; 34.8; 42.2; 52.0; 54.0; 59.3; 61.1; 62.3; 62.6; 64.6; 66.6; 69.0; 69.3; 70.1; 70.3; 70.8 (3×C); 70.9; 71.2; 73.1; 75.0; 75.7; 76.7; 77.1; 77.2; 77.7; 100.4; 100.9; 102.8; 104.0; 117.4; 134.6; 158.8; 174.9; 175.5; 176.1.

μmol) of guanosine diphosphate-D-arabinose analogously to Example 6(c). $^1$H-NMR (CD$_3$OD, 250.13 MHz) δ=1.29 (m, 8 H); 1.56 (m, 4 H); 1.69 (broad t, 12.4 Hz, 1 H); 1.96 (s, 3 H); 2.30 (t, 8.4 Hz, 2 H); 2.75 (dd, 12.4 Hz, 3.4 Hz, 1 H); 3.46–34.05 (m, 29 H); 4.19 (dd, 8.2 Hz, 3.4 Hz, 1 H); 4.46–4.72 (m, 4 H); 5.27 (dd, 8.9 Hz, 1.4 Hz, 1 H); 5.35 (dd, 17.0 Hz, 1.5 Hz, 1 H); 5.96 (m, 1 H). $^{13}$C-NMR (CD$_3$OD, 62.98 MHz) δ=24.15; 26.50; 27.19; 30.34 (2×C); 30.48; 31.37; 35.92; 42.07; 54.12; 54.34; 60.06; 63.42; 65.00; 65.06; 65.83; 69.47; 70.08; 70.53 (2×C); 71.20; 72.94; 72.99; 73.67; 75.60 (2×C); 76.24; 76.69; 76.81 (2×C); 77.14; 77.82; 100.84; 101.92; 103.64; 103.87; 119.89; 134.62; 159.89; 176.19; 175.5; 176.1.

EXAMPLE B1.2

Preparation of Compound No. (14)

EXAMPLE B2.1

Preparation of Compound No. (1)

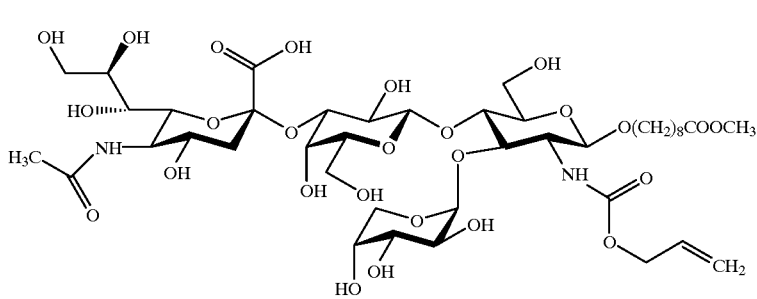

(14)

8.0 mg (66%) of compound No. (14) are obtained from 10.7 mg (12 μmol) of compound No. (13) and 10.5 mg (17

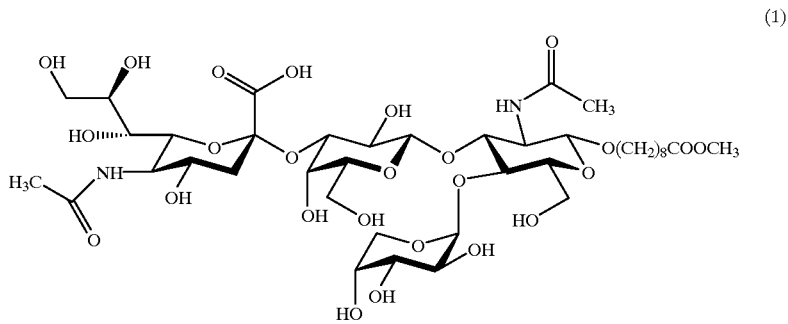

(1)

(a) Galactosylation with β(1→3)galactose transferase 6.8 mg (17.4 μmol) of compound No. (3), dissolved in 35 μl of DMSO, 13.8 mg (12.7 μmol) of UDP-gal, 0.9 mg of BSA and 28 μl of a 0.5 M manganese(II) chloride solution are added to 25 μl of sodium cacodylate buffer (0.05 M, pH=6.45). 600 μl (0.4 U/0.5 ml) of galactose transferase (JP 92-336436 921216) and 33 U (2 μl) of alkaline phosphatase from the bovine intestine (Boehringer) are added to the resulting homogeneous, milky suspension. The mixture is mixed briefly and incubated at 37° C., while stirring. At the end of the reaction, the reaction precipitates are centrifuged off, the clear supernatant is lyophilized from water/dioxane and the residue is purified by chromatography over silica gel (eluent: methylene chloride/methanol/water mixtures). The solvent is removed, the residue is taken up in dioxane/water and renewed lyophilization gives 9.3 mg (97%) of compound No. (4).

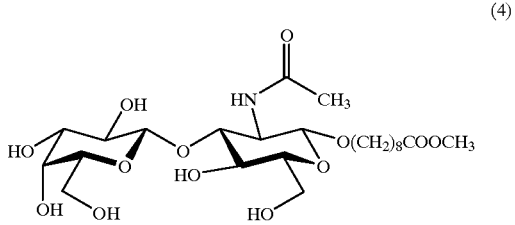

(4)

$^1$H-NMR (CD$_3$OD, 250.13 MHz) δ=1.28 (m, 8 H); 1.49 (m, 4 H); 1.91 (s, 3 H); 2.27 (t, 7.6 Hz, 2 H); 3.30–3.88 (m, 17 H); 4.21 (d, 7.6 Hz, 1 H); 4.42 (d, 8.6 Hz, 1 H). $^{13}$C-NMR (CD$_3$OD, 62.98 MHz) δ=23.17; 26.02; 27.03; 30.13; 30.28; 30.38; 30.59; 34.78; 52.55; 56.35; 62.50; 62.72; 70.21; 70.59 (2×C); 72.37; 74.65; 77.13; 77.57; 84.98; 102.38; 105.59; 174.11; 176.01.

(b) Sialidation with α(2→3)sialic acid transferase 81.2 mg (70%) of compound No. (5) are obtained as a white powder according to Example B1.1(b) from 76 mg (13.7 μmol) of compound No. (4).

(c) Fucosylation with fucose transferase III 10.7 mg (12.7 μmol) of compound No. (5), 13.7 mg (22.1 μmol) of GDP-ara and 1.7 mg of BSA are added to a mixture of 150 μl of manganese(II) chloride solution (0.25 M), 450 μl of sodium cacodylate buffer (0.25 M, pH=6.48) and 600 μl of doubly distilled water. 2 μl (32 U) of alkaline phosphatase from the bovine intestine (Boehringer) and 166 μl (100 mU) of a fucose transferase III solution are added, the components are mixed and the mixture is incubated at 37° C., while stirring. At the end of the reaction, the reaction precipitates are centrifuged off and the clear supernatant is passed over a reversed phase C-18 column (eluent: methanol). The product-containing fractions are lyophilized from water/dioxane, filtered over an Na$^+$ column (Dowex) and lyophilized again. Finally, the residue is purified over a silica gel column (eluent: methylene chloride/methanol/water mixtures) and the product is lyophilized again from water/dioxane. Compound No. (1) is obtained as a white powder (9.2 mg) (75%). $^1$H-NMR (CD$_3$OD, 250.13 MHz) δ=1.27 (m, 8 H); 1.51 (m, 4 H); 1.63 (broad t, 11.0 Hz, 1 H); 1.91 (s, 3 H); 1.93 (s, 3 H); 2.25 (t, 7.6 Hz, 2 H); 2.80 (dd, 11.0 Hz, 4.5 Hz, 1 H); 3.26–4.03 (m, 28 H); 4.38 (d, 8.6 Hz, 1 H); 4.41 (d, 8.6 Hz, 1 H); 4.75 (broad d, 11.6 Hz, 1 H); 5.01 (d, 3.4 Hz, 1 H). $^{13}$C-NMR (CD$_3$OD, 62.98 MHz) δ=22.99; 23.50; 26.01; 27.03; 30.12; 30.27; 30.36; 30.60; 34.79; 42.50; 51.98; 53.91; 57.38; 61.41; 62.77; 64.43; 65.35; 68.39; 69.37; 69.97; 70.32 (2×C); 70.64 (2×C); 71.07; 72.81; 74.19; 74.86; 76.76; 77.38; 77.81 (2×C); 100.29; 100.93; 102.31; 104.27; 174.00; 174.73; 175.44; 176.05.

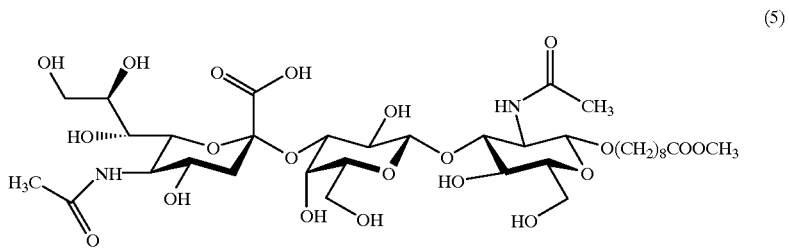

(5)

$^1$H-NMR (CD$_3$OD, 250.13 MHz) δ=1.23 (m, 8 H); 1.49 (m, 4 H); 1.68 (broad t, 11.0 Hz, 1 H); 1.89 (s, 3 H); 1.93 (s, 3 H); 2.12 (t, 7.6 Hz, 2 H); 2.73 (dd, 11.0 Hz, 4.5 Hz, 1 H); 3.28–3.90 (m, 24 H); 3.96 (dd, 8.3 Hz, 3.4 Hz, 1 H); 4.27 (d, 7.6 Hz, 1 H); 4.39 (d, 7.6 Hz, 1 H). $^{13}$C-NMR (CD$_3$OD, 62.98 MHz) δ=22.74; 23.44; 26.00; 27.01; 30.12; 30.28; 30.38; 30.57; 34.77; 41.79; 51.99; 53.98; 56.08; 62.69 (2×C); 64.24; 69.20; 69.88; 70.50 (2×C); 72.92; 74.88; 76.75; 77.52 (3×C); 85.09; 101.17; 102.40; 105.49; 174.18; 175.50; 175.99 (2×C).

EXAMPLE B2.2

Preparation of Compound No. (6)

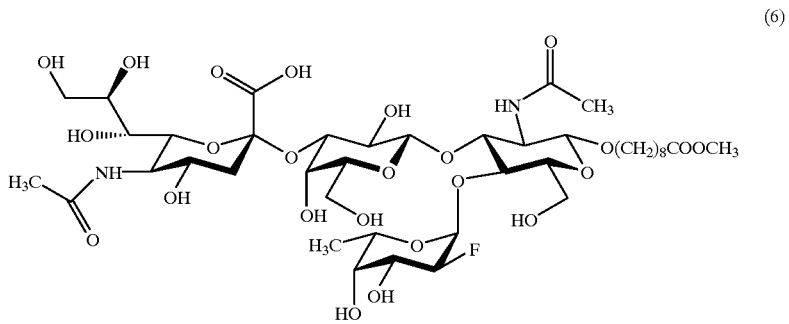

(6)

12.0 mg (88%) of compound No. (6) are obtained from 11.4 mg (14 μmol) of compound No. (5) and 14.8 mg (23 μmol) of GDP-2-fluoro-fucose analogously to Example B2.1. $^1$H-NMR (CD$_3$OD, 250.13 MHz) δ=1.11 (d, 7.5 Hz, 3 H); 1.26 (m, 8 H); 1.48 (m, 4 H); 1.64 (broad t, 11.0 Hz, 1 H); 1.93 (s, 3 H); 1.95 (s, 3 H); 2.22 (t, 7.6 Hz, 2 H); 2.80 (dd, 11.0 Hz, 4.5 Hz, 1 H); 3.25–4.08 (m, 26 H); 4.39 (d, 8.6 Hz, 1 H); 4.41 (d, 8.6 Hz, 1 H); 4.51 (m, 1 H); 4.85 (broad q, 7.5 Hz, 1 H); 5.19 (d, 3.4 Hz, 1 H). $^{13}$C-NMR (CD$_3$OD, 62.98 MHz) δ=16.37; 22.61; 23.56; 26.02; 27.02; 30.13; 30.27; 30.37; 30.60; 34.79; 41.83; 51.97; 53.88; 57.51; 60.97; 63.12; 64.45; 67.85; 68.30; 69.30 (d); 69.48; 70.00; 70.65; 70.86; 72.85; 74.08; 74.30 (d); 74.81; 76.60; 77.45; 77.89; 77.95; 90.57 (d); 97.44 (d); 101.42; 102.42; 104.74; 173.98; 174.92; 175.26; 176.96.

EXAMPLE B2.3

Preparation of Compound No. (7)

7.6 mg (48%) of compound No. (7) are obtained from 13.4 mg (16 μmol) of compound No. (5) and 13.1 mg (21 μmol) of GDP-2-amino-fucose analogously to Example B2.1. $^1$H-NMR (CD$_3$OD, 250.13 MHz) δ=1.12 (d, 7.5 Hz, 3 H); 1.21 (m, 8 H); 1.49 (m, 4 H); 1.63 (broad t, 11.0 Hz, 1 H); 1.91 (s, 3 H); 1.93 (s, 3 H); 2.23 (t, 7.6 Hz, 2 H); 2.78 (dd, 11.0 Hz, 1 H); 3.14 (dd, 10.3 Hz, 5.5 Hz, 1 H); 3.29–3.86 (m, 23 H); 3.91 (m, 2 H); 4.13 (t, 8.3 Hz, 1 H); 4.40 (d, 8.6 Hz, 1 H); 4.50 (d, 8.6 Hz, 1 H); 4.61 (broad q, 7.5 Hz, 1 H); 5.16 (d, 3.4 Hz, 1 H). $^{13}$C-NMR (CD$_3$OD, 62.98 MHz) δ=16.58; 22.59; 23.56; 26.02; 27.03; 30.14; 30.28; 30.38; 30.61; 34.79; 42.32; 51.97; 52.52; 53.92; 58.19; 63.05; 64.58; 68.42; 68.66; 69.15; 69.43; 70.09; 70.59; 70.80; 71.98; 72.56; 72.88; 73.83; 74.86; 76.60; 76.68; 76.89; 77.88; 100.94 (2×C); 101.82; 104.38; 173.99; 174.96; 175.41; 176.01.

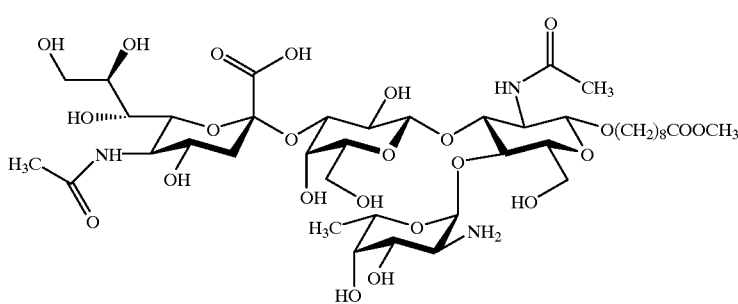

(7)

55

EXAMPLE B2.4

Preparation of Compound No. (8)

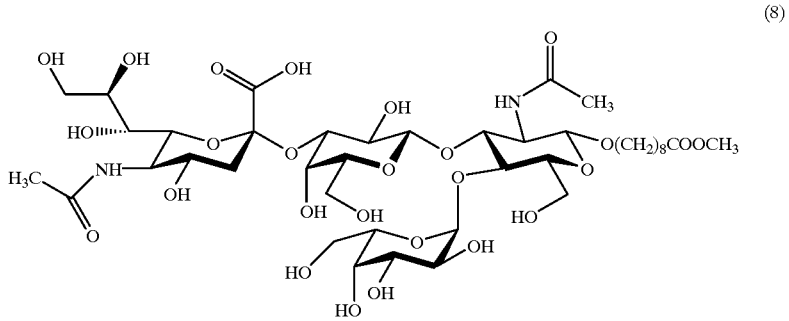

(8)

9.9 mg (83%) of compound No. (8) are obtained from 10.1 mg (12 μmol) of compound No. (5) and 14.0 mg (22 μmol) of GDP-L-galactose analogously to Example B2.1. $^1$H-NMR (CD$_3$OD, 250.13 MHz) δ=1.27 (m, 8 H); 1.52 (m, 4 H); 1.65 (broad t, 11.0 Hz, 1 H); 1.95 (s, 3 H); 1.97 (s, 3 H); 2.26 (t, 7.6 Hz, 2 H); 2.81 (dd, 11.0 Hz, 4.5 Hz, 1 H); 3.29–3.99 (m, 29 H); 4.39 (d, 7.6 Hz, 1 H); 4.42 (d, 7.6 Hz, 1 H); 4.72 (t, 7.5 Hz, 1 H); 5.03 (d, 3.4 Hz, 1 H). $^{13}$C-NMR (CD$_3$OD, 62.98 MHz) δ=22.61; 23.62; 26.01; 27.03; 30.12; 30.28; 30.36; 30.61; 34.79; 42.51; 51.97; 53.91; 57.46; 61.38; 62.40; 62.81; 64.48; 68.51; 69.42; 70.02; 70.33 (2×C); 70.63 (2×C); 70.95; 71.14; 72.76; 74.28; 74.85; 76.70; 77.39; 77.71; 78.65; 99.93; 101.02; 102.21; 104.81; 174.10; 174.75; 175.43; 176.04.

EXAMPLE B2.5

Preparation of Compound No. (9)

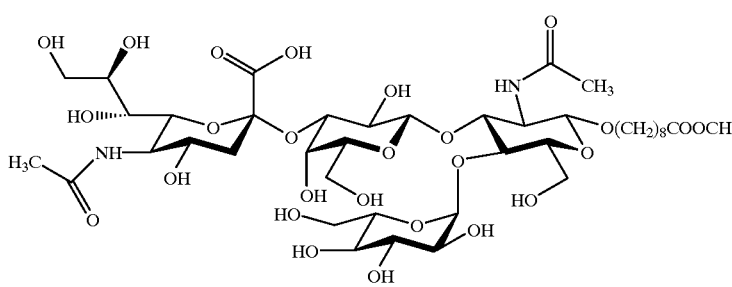

(9)

7.1 mg (52%) of compound No. (9) are obtained from 11.5 mg (14 μmol) of compound No. (5) and 11.2 mg (17 lrmol) of GDP-L-glucose analogously to Example B2.1. $^1$H-NMR (CD$_3$OD, 250.13 MHz) δ=1.29 (m, 8 H); 1.53 (m, 4 H); 1.66 (broad t, 11.0 Hz, 1 H); 1.97 (s, 3 H); 1.99 (s, 3 H); 2.29 (t, 7.6 Hz, 2 H); 2.72 (dd, 11.0 Hz, 4.5 Hz, 1 H); 3.16–3.98 (m, 30 H); 4.40 (d, 7.6 Hz, 1 H); 4.46 (d, 7.6 Hz, 1 H); 5.06 (d, 3.4 Hz, 1 H). $^{13}$C-NMR (CD$_3$OD, 62.98 MHz) δ=22.60; 23.52; 26.02; 27.03; 30.13; 30.27; 30.37; 30.60; 34.79; 42.33; 51.97; 53.89; 57.34; 61.32; 62.16; 62.84; 64.44; 68.84; 69.46; 69.99; 70.64; 70.79; 72.17; 72.73 (2×C); 72.94; 73.73; 74.55; 74.82; 76.97; 77.43; 77.72; 78.45; 98.92; 101.09; 102.46; 105.14; 174.02; 174.86; 175.38; 176.55.

EXAMPLE B3.1

Preparation of Compound No. (15)

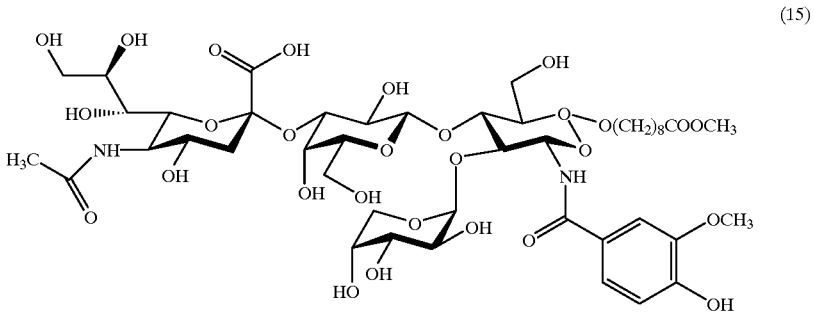

(a) 27 mg (100%) of disaccharide No. (19) are obtained according to Example B1.1(a1) from 21 mg (33 μmol) of compound No. (16) and 32 mg (52 μmol) of UDP-gal (in this case the incubation mixture comprises 12% of DMSO (vol/vol)).

(b) 32 mg (86%) of compound No. (20) are obtained according to Example B1.1(b) (in this case the buffer solution comprises 9% of DMSO (vol/vol)) from 26 mg (39 μmol) of compound No. (19) and 39 mg (59 μmol) of CMP-sia.

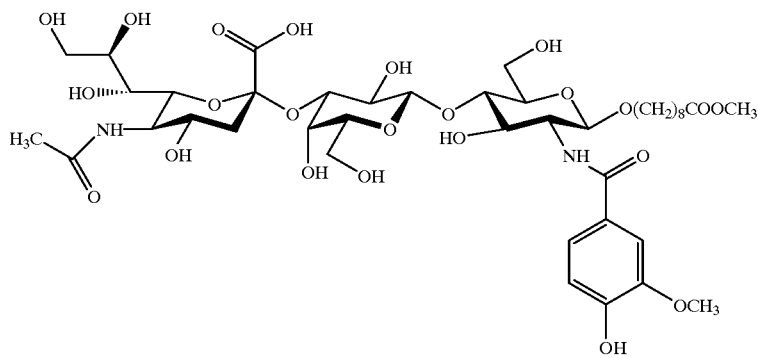

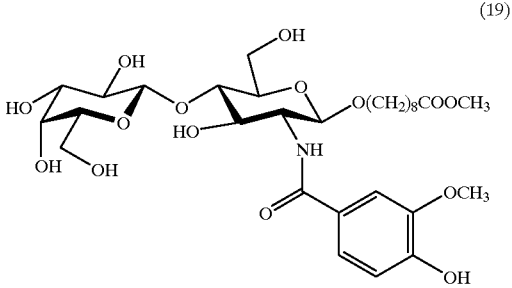

$^1$H-NMR (CD$_3$OD-CDCl$_3$, 250.13 MHz) δ=1.05 (m, 8 H); 1.40 (m, 4 H); 2.17 (t, 7.5 Hz, 2 H); 3.35–3.92 (m, 20 H); 4.35 (d, 8.3 Hz, 1 H); 4.57 (d, 8.2 Hz, 1 H); 6.79 (d, 8.3 Hz, 1 H); 7.31 (dd, 2.1 Hz, 8.3 Hz, 1 H); 7.39 (d, 2.1 Hz, 1 H); $^{13}$C-NMR (CD$_3$OD-CDCl$_3$, 100.61 MHz) δ=25.60; 26.63; 29.71; 29.89; 29.95; 34.72; 52.32; 56.46; 56.81; 61.23; 61.82; 69.55; 70.68; 71.95; 73.00; 73.83; 75.71; 76.38; 80.05; 102.70; 104.13; 111.48; 114.93; 121.38; 126.40; 146.93; 150.11; 168.85; 175.98.

$^1$H-NMR (CD$_3$OD, 250.13 MHz) δ=1.02 (m, 8 H); 1.48 (m, 4 H); 1.68 (broad t, 11.6 Hz, 1 H); 1.94 (s, 3 H); 2.14 (t, 7.6 Hz, 2 H); 2.76 (dd, 11.6 Hz, 2.8 Hz, 1 H); 3.32–4.01 (m, 27 H); 4.38 (d, 8.6 Hz, 1 H); 4.48 (d, 8.6 Hz, 1 H); 6.73 (d, 8.3 Hz, 1 H); 7.30 (dd, 2.1 Hz, 8.3 Hz, 1H); 7.39 (d, 2.1 Hz, 1 H); $^{13}$C-NMR (CD$_3$OD-CDCl$_3$, 62.90 MHz) δ=22.70; 25.91; 27.07; 30.01; 30.27 (2×C); 30.58; 34.72; 42.06; 51.90; 53.89; 56.44; 57.03; 62.03; 62.66; 64.05; 69.15; 69.92; 72.91; 74.03; 74.84; 76.42; 76.89; 77.50; 78.67; 79.20; 79.72; 81.77; 101.05; 102.90; 104.97; 112.11; 115.72; 122.10; 127.03; 148.66; 151.18; 170.12; 175.04; 175.45; 176.05.

(c) 10 mg (81%) of compound No. (15) are obtained according to Example B1.1(c) from 11 mg (11 μmol) of compound No. (20) and 11 mg (18 μmol) of GDP-arabinose. $^1$H-NMR (CD$_3$OD, 400.13 MHz) δ=0.96–1.58 (very broad m, 12 H); 1.68 (broad t, 11.0 Hz, 1 (s, 3 H); 2.20 (t, 7.6 Hz, 2 H); 2.84 (dd, 11.6 Hz, 2.8 Hz, 1 H); 3.36 (dd, 3.0 Hz, 10.8 Hz, 1 H); 3.39–4.11 (m, 27 H); 4.51 (d, 8.6 Hz, 1 H); 4.60 (broad d, 8.6 Hz, 1 H); 5.10 (d, 3.6 Hz, 1 H); 6.78 (d, 8.3 Hz, 1 H); 7.33 (dd, 2.1 Hz, 8.3 Hz,1H); 7.42 (d, 2.1 Hz, 1 H); $^{13}$C-NMR (CD$_3$OD, 100.60 MHz) δ=22.57; 25.97; 27.17;

30.07; 30.31; 30.33; 30.66; 34.76; 42.37; 51.95; 53.97; 56.47; 57.96; 61.40; 62.96; 64.67; 65.15; 68.84; 69.31; 70.14; 70.21 (2×C); 70.72; 70.91; 70.99; 73.03; 75.01; 75.44; 75.90; 76.80; 77.31; 77.88; 99.89; 100.86; 102.62; 103.81; 112.28; 115.91; 122.20; 126.75; 148.91; 151.72; 170.29; 174.82; 175.50; 176.09.

EXAMPLE B3.2

Preparation of Compound No. (21)

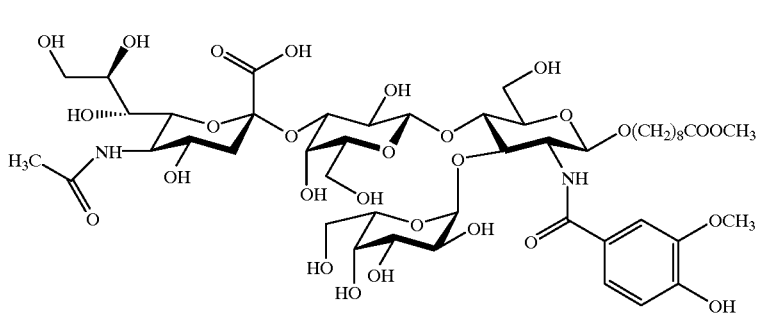

(21)

8 mg (68%) of compound No. (21) are obtained according to Example B3.1(c) from 10 mg (10 μmol) of compound No. (20) and 12 mg (17 μmol) of GDP-L-galactose. $^1$H-NMR (CD$_3$OD, 250.13 MHz) δ=0.96 (m, 8 H); 1.39 (m, 4 H); 1.42 (broad t, 11.0 Hz, 1 H); 1.92 (s, 3 H); 2.16 (t, 7.6 Hz, 2 H); 2.80 (dd, 11.6 Hz, 2.8 Hz, 1 H); 3.31–4.10 (m, 32 H); 4.49 (d, 8.6 Hz, 1 H); 4.53 (broad d, 8.6 Hz, 1 H); 4.65 (broad t, 6.9 Hz, 1 H); 5.04 (d, 5.5 Hz, 1 H); 6.74 (d, 8.3 Hz, 1 H); 7.29 (dd, 2.1 Hz, 8.3 Hz, 1 H); 7.39 (d, 2.1 Hz, 1 H); $^{13}$C-NMR (CD$_3$OD, 62.90 MHz) δ=22.57; 25.98; 27.18; 30.09; 30.34 (2×C); 30.65; 34.76; 42.32; 51.96; 53.96; 56.46; 58.36; 61.24; 62.42; 62.69; 64.66; 69.02; 69.28; 70.20 (2×C); 70.66; 70.72 (2×C); 70.92; 71.05; 73.05; 75.02; 75.86; 76.45; 76.78; 77.34; 77.68; 99.89; 100.91; 102.55; 104.05; 112.25; 115.87; 122.22; 126.88; 148.86; 151.60; 170.37; 174.79; 175.52 (2×C).

EXAMPLE B4.1

Preparation of Compound No. (22)

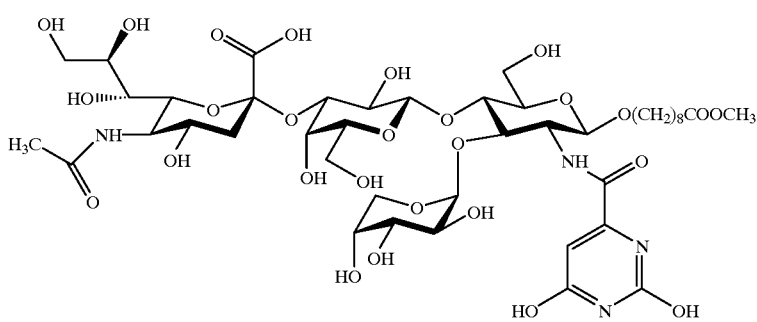

(22)

(a) 35 mg (52%) of disaccharide No. (24) are obtained according to Example B1.1(a) from 49 mg (100 μmol) of compound No. (23) and 78 mg (127 μmol) of UDP-gal (in this case the incubation mixture comprises 12% of DMSO (vol/vol)).

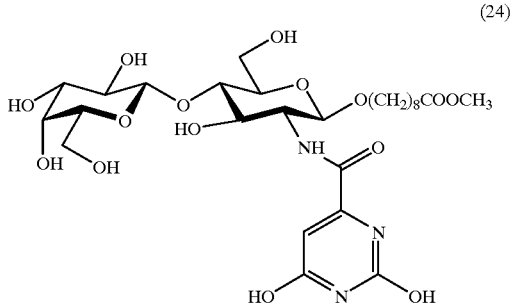

(24)

$^1$H-NMR (D$_6$-DMSO-CD$_3$OD-D$_2$O, 400.13 MHz) δ=1.18 (m, 8 H); 1.46 (m, 4 H); 2.22 (t, 7.5 Hz, 2 H); 3.32–3.86 (m, 14 H); 3.58 (s, 3 H); 4.44 (d, 8.6 Hz, 1 H); 6.12 (s, 1 H); remaining signals masked by the solvent. $^{13}$C-NMR (D$_6$-DMSO-CD$_3$OD-D$_2$O, 62.89 MHz) δ=25.93; 26.98; 30.07; 30.24; 30.29; 30.49; 35.00; 52.45; 57.55; 62.05; 62.73; 70.49; 71.80; 72.46; 73.53; 74.99; 76.79; 76.91; 80.71; 100.81; 102.61; 105.20; 176.45; no resolution of the remaining signals.

(b) 41 mg (86%) of compound No. (25) are obtained according to Example B 1.1(b) (in this case the buffer solution comprises 9% of DMSO (vol/vol)) from 33 mg (51 µmol) of compound No. (24) and 53 mg (80 µmol) of CMP-sia.

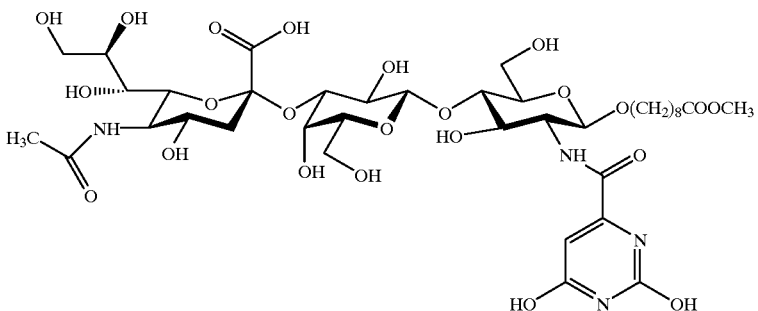

(25)

$^1$H-NMR (CD$_3$OD-D$_2$O, 250.13 MHz) δ=1.17 (m, 8 H); 1.45 (m, 4 H); 1.68 (broad t, 11.0 Hz, 1 H); 1.94 (s, 3 H); 2.20 (t, 7.6 Hz, 2 H); 2.74 (broad d, 11.0 Hz, 1 H); 3.29–4.02 (m, 24 H); 4.38 (d, 8.6 Hz, 1 H); 4.42 (d, 8.6 Hz, 1 H); 6.05 (s, 1 H). $^{13}$C-NMR (CD$_3$OD-D$_2$O, 62.89 MHz) δ=22.35; 25.72; 26.93; 29.84; 30.06; 30.19; 30.29; 34.48; 41.62; 51.70; 53.67; 57.00; 61.68; 62.44; 64.13; 68.87; 68.96; 69.02; 69.73; 70.58; 72.70; 73.46; 74.65; 76.31; 76.74; 77.36; 80.93; 100.43; 100.90; 102.16; 104.74; 166.82; 174.86; 175.26; 175.85; no resolution of the remaining signals.

(c) 8 mg (62%) of compound No. (22) are obtained according to Example B1.1(c) from 11 mg (12 µmol) of compound No. (25) and 10 mg (60 µmol) of GDP-D-arabinose. $^1$H-NMR (CD$_3$OD, 500.00 MHz) δ=1.18 (m, 8 H); 1.48 (m, 4 H); 1.66 (broad t, 11.0 Hz, 1 H); 1.95 (s, 3 H); 2.20 (t, 7.6 Hz, 2 H); 2.72 (dd, 11.6 Hz, 2.8 Hz, 1 H); 3.36–4.03 (m, 28 H); 4.49 (d, 8.6 Hz, 2 H); 4.58 (d, 8.6 Hz, 1 H); 5.02 (d, 3.6 Hz, 1 H); 6.09 (s, 1 H); $^{13}$C-NMR (CD$_3$OD, 126.00 MHz) δ=22.10; 25.55; 26.73; 29.67; 29.88; 29.96; 30.15; 34.33; 41.53; 51.49; 53.48; 57.19; 60.82; 61.67; 62.50; 64.68; 68.42; 68.85; 69.65; 69.67; 69.72; 70.34; 70.44; 70.47; 72.56; 74.53; 74.78; 75.56; 76.28; 76.84; 77.40; 99.72; 100.42; 101.83; 103.29; 112.28; 174.37; 175.01; 175.64; no resolution of the remaining signals.

EXAMPLE B4.2

Preparation of Compound No. (26)

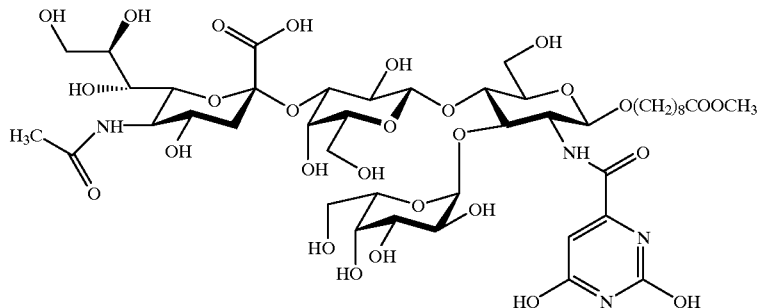

(26)

7 mg (53%) of compound No. (26) are obtained according to Example B4.1(c) from 11 mg (12 µmol) of compound No. (25) and 11 mg (17 µmol) of GDP-L-galactose. $^1$H-NMR (CD$_3$OD, 500.00 MHz) δ=1.22 (m, 8 H); 1.48 (m, 4 H); 1.67 (broad t, 11.0 Hz, 1 H); 1.97 (s, 3 H); 2.24 (t, 7.6 Hz, 2 H); 2.84 (dd, 11.6 Hz, 2.8 Hz, 1 H); 3.38–4.08 (m, 29 H); 4.53

(broad d, 8.6 Hz, 2 H); 4.69 (broad t, 5.5 Hz, 1 H); 5.03 (d, 3.6 Hz, 1 H); 6.13 (s, 1 H); $^{13}$C-NMR (CD$_3$OD, 125.80 MHz) δ=22.58; 26.01; 27.23; 30.12; 30.33; 30.40; 34.79; 42.28; 51.96; 53.99; 57.85; 61.16; 62.20; 62.67; 64.69; 69.08; 69.29; 70.13; 70.26; 70.81 (2×C); 70.91; 71.15; 71.39; 73.02; 75.04; 75.79; 76.72; 76.99; 77.41; 77.72; 100.47; 100.96; 101.11; 104.09; 112.21; 174.78; 175.51; 175.12; no resolution of the remaining signals.

EXAMPLE B5.1

Preparation of Compound No. (48)

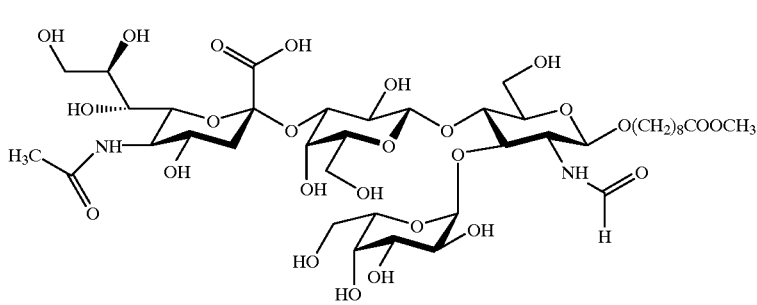

(48)

(a) 28 mg (83%) of compound No. (50) are obtained according to Example B1.1(a) (in this case the buffer solution comprises about 5% of DMSO (vol/vol)) from 24 mg (64 μmol) of No. (49) and 50 mg (80 μmol) of UDP-gal.

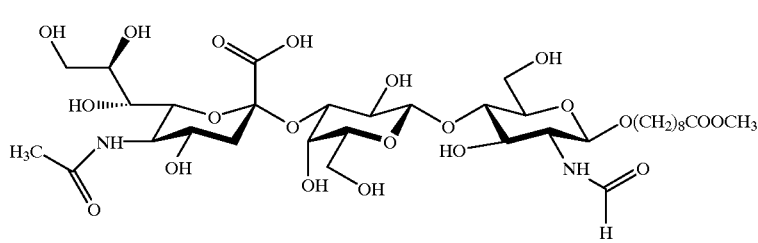

(51)

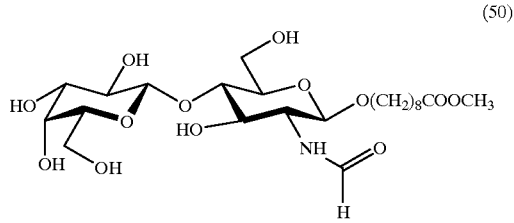

(50)

$^1$H-NMR (CD$_3$OD-CDCl$_3$-D$_2$O, 250.13 MHz) δ=1.29 (m, 8 H); 1.58 (m, 4 H); 2.30 (t, 7.6 Hz, 2 H); 8.13 (broad t, 8.5 Hz, 0.4 H); 3.36–3.98 (m, 16.6 H); 4.40 (m, 2 H); 7.96 (s, 0.4 H); 8.15 (s, 0.6 H). M: main isomer; S: secondary isomer; $^{13}$C-NMR (CD$_3$OD-CDCl$_3$-D$_2$O, 62.90 MHz, DEPT) δ=25.54; 26.42 M; 26.48 S; 29.60; 29.74; 29.79; 30.03; 34.53; 52.11; 55.10 M; 59.69 S; 61.22; 62.03; 69.72; 70.67 M; 70.93 S; 72.11; 73.11 S; 73.40 M; 74.05; 75.77 S; 75.93 M; 76.53; 79.96; 101.71 S; 101.90 M; 104.30; 164.02 M; 167.98 S.

(b) 31 mg (77%) of compound No. (51) are obtained according to Example B1.1(b) from 26 mg (48 μmol) of compound No. (50) and 54 mg (64 μmol) of CMP-sia.

$^1$H-NMR (CD$_3$OD, 250.13 MHz) δ=1.18 (m, 8 H); 1.56 (m, 4 H); 1.68 (t, 11.6 Hz, 1 H); 2.00 (s, 3 H); 2.36 (t, 7.6 Hz, 2 H); 2.66 (dd, 11.6 Hz, 2.8 Hz, 1 H); 3.49–4.02 (m, 23 H); 4.10 (dd, 11.08 Hz, 2.8 Hz, 1 H); 4.52 (m, 2 H); 7.95 (s, 0.3 H); 8.16 (s, 0.7 H). $^{13}$C-NMR (CD$_3$OD, 62.90 MHz) δ=24.20; 26.44; 27.05; 30.21; 30.27; 30.41; 30.62; 35.87; 41.79; 53.84; 54.21; 56.07 M; 60.92 S; 62.19; 63.19; 64.73; 69.62; 70.24; 70.52; 71.55; 72.70 M; 73.09 S; 73.93; 74.39; 75.04; 76.93; 77.33; 77.63; 80.37; 101.96; 102.61 S; 102.94 M; 104.73; 166.79 M; 170.26 S; 176.06; 177.16; 180.09.

(c) 13 mg (29%) of compound No. (48) are obtained according to Example B1.1(c) from 37 mg (45 μmol) of compound No. (51) and 40 mg (61 μmol) of GDP-L-galactose. $^1$H-NMR (CD$_3$OD, 400.13 MHz) δ=1.25 (m, 8 H); 1.52 (m, 4 H); 1.65 (broad t, 11.0 Hz, 1 H); 1.96 (s, 3 H); 2.25 (t, 7.6 Hz, 2 H); 2.82 (dd, 11.6 Hz, 2.8 Hz, 1 H); 3.31–4.06 (m, 29 H); 4.26 (d, 8.6 Hz, 0.4 H); 4.44 (d, 8.6 Hz, 0.6 H); 4.50 (m, 2 H); 5.08 (d, 4.3 Hz, 1 H); 7.95 (s, 0.4 H); 8.15 (s, 0.6 H). $^{13}$C-NMR (CD$_3$OD, 100.60 MHz) δ=22.64; 25.99; 26.99; 30.09; 30.24; 30.51; 34.78; 42.23; 51.98;

53.95; 56.11 M; 60.86; 61.22; 62.01; 62.32; 62.64; 62.60; 64.57; 68.72; 68.98; 69.22; 70.07; 70.14; 70.50; 70.53; 70.69; 70.87 (2×C); 70.96; 71.19; 73.05; 74.97; 75.39 S; 75.65 M; 76.52 S; 76.65; 77.00; 77.28; 77.61; 100.12 M; 100.27 S; 100.91; 102.11 M; 102.19; 103.95; 164.50 M; 168.49 S; 174.85; 175.53; 176.05.

EXAMPLE B5.2

Preparation of Compound No. (64)

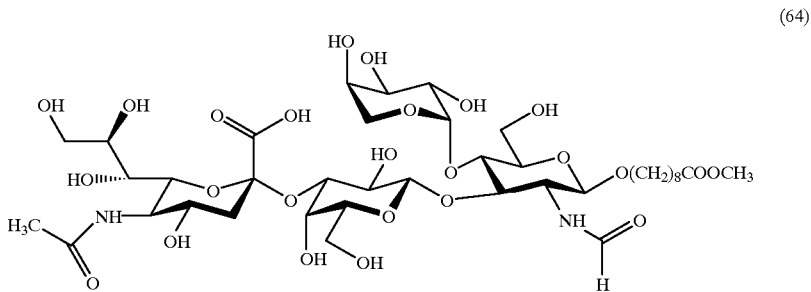

(64)

(a) 11 mg (29%) of disaccharide No. (65) are obtained as two amide isomers (about 60/40) according to Example B2.1(a) from 26 mg (69 μmol) of compound No. (49) and 52 mg (84 μmol) of UDP-gal.

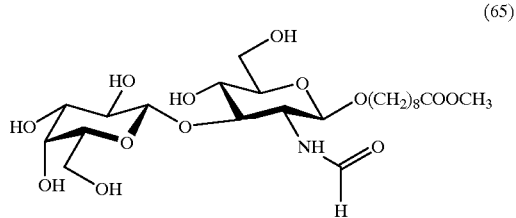

(65)

$^1$H-NMR (CD$_3$OD-CDCl$_3$, 250.13 MHz) δ=1.22 (m, 8 H); 1.50 (m, 4 H); 2.22 (t, 7.6 Hz, 2 H); 3.13–3.89 (m, 17 H); 4.22 (d, 8.6 Hz, 0.6 H); 4.24 (d, 8.6 Hz, 0.4 H); 4.30 (d, 8.6 Hz, 0.4 H); 4.43 (d, 8.6 Hz, 0.6 H); 7.84 (s, 0.4 H); 8.02 (s, 0.6 H. M: main isomer; S: secondary isomer; $^{13}$C-NMR (CD$_3$OD-CDCl$_3$, 62.90 MHz) δ=25.85; 26.81; 29.95; 30.10; 30.15; 30.41; 34.76; 52.10; 55.20 M; 59.51 S; 62.34; 62.47; 70.00 M; 70.10 S; 70.32; 70.70 M; 70.98 S; 77.07 S; 72.26 M; 74.33; 76.88; 76.98 S; 77.07 M; 82.61 S, 83.99 M; 101.88 M; 102.07 S; 104.55 S; 105.01 M; 164.51 M; 168.43 S; 176.21.

(b) 10 mg (55%) of compound No. (66) are obtained as two amide isomers according to Example B1.1(b) from 12 mg (22 μmol) of compound No. (65) and 23 mg (35 μmol) of CMP-sia.

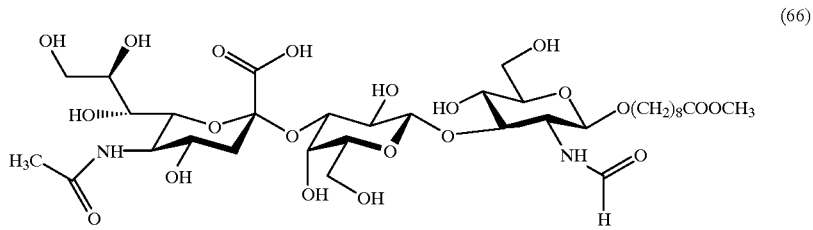

(66)

$^1$H-NMR (CD$_3$OD, 250.13 MHz) δ=1.23 (m, 8 H); 1.48 (m, 4 H); 1.64 (broad t, 11.6 Hz, 1 H); 1.91 (s, 3 H); 2.21 (t, 7.6 Hz, 2 H); 2.77 (dd, 11.6 Hz, 2.8 Hz, 1 H); 3.11–3.88 (m, 23 H); 3.93 (dd, 10.3 Hz, 3.4 Hz, 1 H); 4.24 (d, 8.6 Hz, 0.4 H); 4.30 (d, 8.6 Hz, 0.6 H); 4.38 (d, 8.6 Hz, 0.4 H); 4.44 (d, 8.6 Hz, 0.6 H); 7.83 (s, 0.4 H); 8.16 (s, 0.6 H). $^{13}$C-NMR (CD$_3$OD, 62.90 MHz) δ=22.61; 26.01; 26.99; 30.12; 30.27; 30.33; 30.59; 34.79; 42.22; 51.98; 53.90; 55.32 M; 59.94 S; 62.70 (2×C); 65.00; 69.09; 69.34; 70.29; 7.50; 70.64 M; 70.96 S; 73.00; 74.91; 77.06; 77.42; 77.57 (2×C); 83.00 S; 84.08 S; 101.17; 102.15 M; 102.63 S; 105.11 S; 105.19 M; 164.71 M; 168.49 S; 174.93; 175.49; 176.05.

(b') Alternatively, the enzyme reactions (a) and (b) can also be carried out together in one reaction step. 9 mg (37%) of trisacchande No. (66) are thus obtained from 10 mg (27 μmol) of amide No. (49), 31 mg (51 μmol) of UDP-gal and 33 mg (51 μmol) of CMP-sia.

(c) 10 mg (89%) of compound No. (64) are obtained according to Example B2.1(c) from 10 mg (12 μmol) of compound No. (66) and 10 mg (15 μmol) of GDP-D-arabinose. $^1$H-NMR (CD$_3$OD, 400.13 MHz) δ=1.22 (m, 8 H); 1.50 (m, 4 H); 1.61 (broad t, 11.0 Hz, 1 H); 1.92 (s, 3 H); 2.23 (t, 7.6 Hz, 2 H); 2.79 (dd, 11.6 Hz, 2.8 Hz, 1 H); 3.23–4.04 (m, 29 H); 4.22 (d, 8.6 Hz, 0.4 H); 4.46 (m, 1.2

H); 4.63 (d, 8.6 Hz, 0.4 H); 5.00 (d, 4.3 Hz, 1 H); 7.84 (s, 0.4 H); 8.09 (s, 0.6 H). $^{13}$C-NMR (CD$_3$OD, 62.90 MHz) δ=22.59; 26.01; 27.02; 30.12; 30.28 (2×C); 30.61; 34.79; 42.48; 51.99; 53.88; 56.30 H; 61.30; 62.95; 63.06; 64.77; 65.13; 65.32; 68.63; 69.25; 70.28 (2×C); 70.43; 70.67; 71.05; 73.05; 73.52; 74.05; 74.94; 76.65; 76.91; 77.27; 77.53; 77.0; 100.10 H; 100.19 N; 100.75; 100.89; 102.03; 102.29; 104.01; 104.34; 164.90 H; 168.31 N; 174.60; 174.83; 175.39; 175.51; 176.55.

EXAMPLE B5.3

Preparation of Compound No. (67)

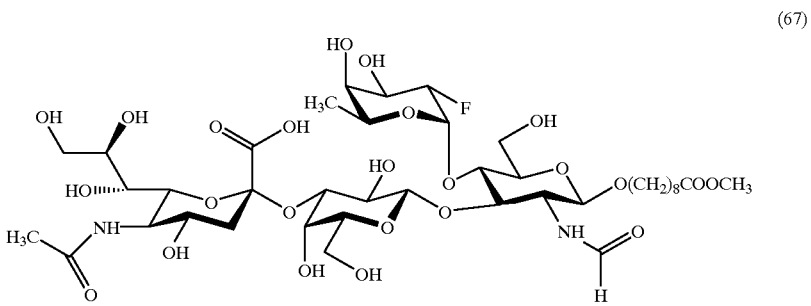
(67)

11 mg (about 73%) of compound No. (67) are obtained according to Example B5.2(c) from 13 mg (15 μmol) of compound No. (66) and 11 mg (18 μmol) of GDP-2-fluoro-fucose. The material isolated comprises about 80% of product No. (67). $^1$H-NMR (CD$_3$OD, 400.13 MHz) δ=1.09 (d, 6.8 Hz, 3 H); 1.61 (broad t, 11.0 Hz, 1 H); 1.91 (s, 3 H); 2.22 (t, 7.6 Hz, 2 H); 2.79 (dd, 11.6 Hz, 2.8 Hz, 1 H); 4.20–4.59 (several d, 3 H); 4.82 (broad q, 6.8 Hz, 0.8 H); 5.15 (d, 4.3 Hz, 0.8 H). $^{13}$C-NMR (CD$_3$OD, 62.90 MHz) δ=16.40; 34.79; 91.01 (d, 180 Hz). $^{19}$F-NMR (CD$_3$OD, 376.5 MHz) δ=−211.4; −210.95; ratio of the two signals: about 70/30.

EXAMPLE B6.1

Preparation of Compound No. (77)

(a) 9 mg (34%) of compound No. (79) are obtained according to Example B2.1(a) from 20 mg (49 μmol) of compound No. (78) and 36 mg (58 μmol) of UDP-gal (in this case the incubation mixture comprises 5% of DMSO (vol/vol)).

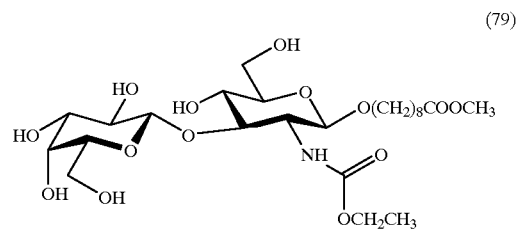
(79)

$^1$H-NMR (CD$_3$OD, 250.13 MHz) δ=1.16 (t, 7.5 Hz, 3 H); 1.22 (m, 8 H); 1.49 (m, 4 H); 2.22 (t, 7.6 Hz, 2 H); 3.15–3.88 (m, 17 H); 3.99 (q, 7.5 Hz, 2 H); 4.25 (d, 8.6 Hz, 1 H); 4.31 (d, 8.6 Hz, 1 H). $^{13}$C-NMR (CD$_3$OD, 100.61 MHz) δ=15.04;

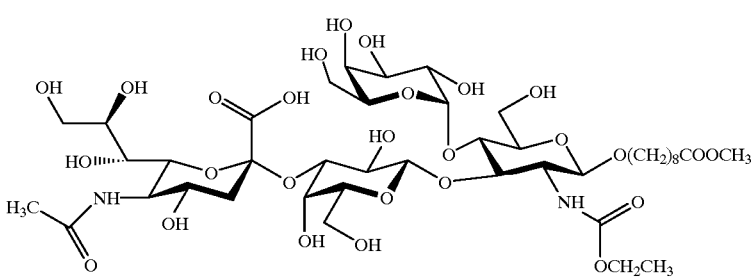
(77)

26.03; 27.02; 30.14; 30.31; 30.38; 30.60; 34.78; 51.97; 57.85; 61.99; 62.52; 62.70; 70.22; 70.55; 70.73; 72.44; 74.53; 77.11; 77.44; 84.71; 102.78; 105.27; 159.49; 176.01.

(b) 18 mg (78%) of compound No. (80) are obtained according to Example B1.1(b) from 16 mg (27 μmol) of compound No. (79) and 25 mg (37 μmol) of CMP-sia (in this case the incubation mixture comprises 8% of DMSO (vol/vol)).

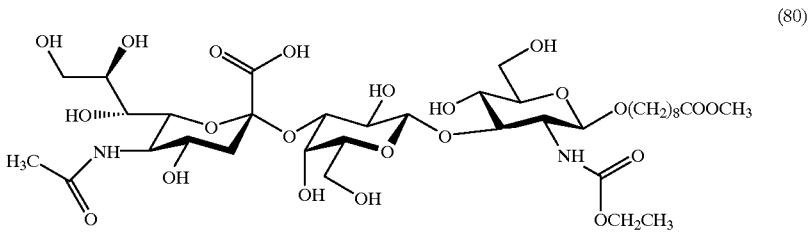

(80)

$^1$H-NMR (CD$_3$OD, 250.13 MHz) δ=1.17 (t, 7.5 Hz, 3 H); 1.20 (m, 8 H); 1.48 (m, 4 H); 1.68 ((broad t, 11.6 Hz, 1 H); 1.91 (s, 3 H); 2.21 (t, 7.6 Hz, 2 H); 2.73 (dd, 11.6 Hz, 2.8 Hz, 1 H; 3.16–4.08 (m, 25 H); 4.30 (d, 8.6 Hz, 1 H); 4.33 (broad d, 8.6 Hz, 1 H). $^{13}$C-NMR (CD$_3$OD, 62.98 MHz) δ=15.19; 22.66; 26.03; 27.00; 30.13; 30.31; 30.37; 30.61; 34.78; 42.00; 51.98; 53.94; 57.69; 62.00; 62.74 (2×C); 69.10; 69.36; 69.56; 69.87; 70.48 (2×C); 70.73; 72.87; 74.88; 76.84; 77.42 (2×C); 84.41; 101.30; 102.99; 104.55; 159.32; 175.45 (2×C); 175.54.

(b') Steps (b) and (c) can also be carried out as a one-pot reaction according to Example B5.2(b). 9 mg (38%) of compound No. (80) are obtained from 12 mg (28 μmol) of compound No. (78), 20 mg (33 μmol) of UDP-gal and 24 mg (36 μmol) of CMP-sia.

(c) 10 mg (94%) of compound No. (77) are obtained according to Example B2.1(c) from 9 mg (11 μmol) of compound No. (80) and 12 mg (19 μmol) of GDP-L-galactose. $^1$H-NMR (CD$_3$OD, 400.13 MHz) δ=1.17 (t, 7.5 Hz, 3 H); 1.21 (m, 8 H); 1.45 (m, 4 H); 1.65 (broad t, 12.4 Hz, 1 H); 1.91 (s, 3 H); 2.21 (t, 8.4 Hz, 2 H); 2.73 (dd, 12.4 Hz, 3.4 Hz, 1 H); 3.21–4.16 (m, 31 H); 4.39–4.59 (m, 2 H); 4.65 (broad t, 7.0 Hz, 1 H); 4.99 (d, 4.8 Hz, 1 H). $^{13}$C-NMR (CD$_3$OD, 126.00 MHz) δ=15.53; 22.61; 26.03; 27.02; 30.13; 30.31; 30.36; 30.65; 34.79; 41.96; 51.98; 53.93; 59.40; 61.36; 62.05; 62.74; 64.25; 68.87; 69.40; 69.79; 70.33; 70.72 (2×C); 70.89 (2×C); 71.17; 72.95; 74.38; 74.90; 76.48; 77.17 (2×C); 77.22; 77.39; 99.85; 101.30; 102.34; 104.35; 158.96; 175.08; 175.45; 176.02.

EXAMPLE B6.2

Preparation of Compound No. (81)

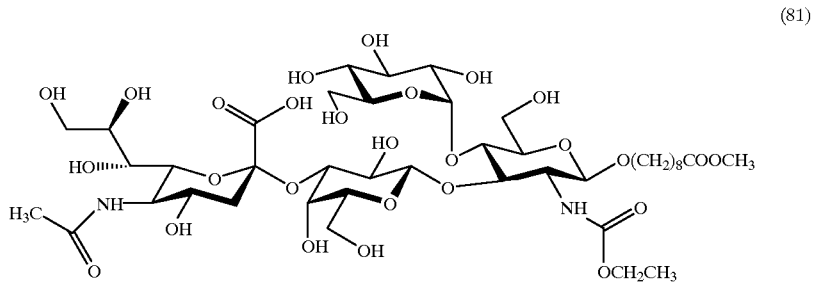

(81)

5 mg (48%) of compound No. (81) are obtained according to Example B6.1(c) from 9 mg (11 μmol) of compound No. (80) and 11 mg (17 μmol) of GDP-L-glucose. $^1$H-NMR (CD$_3$OD, 250.13 MHz) δ=1.28 (t, 7.5 Hz, 3 H); 1.32 (m, 8 H); 1.49 (m, 4 H); 1.76 (broad t, 12.4 Hz, 1 H); 2.02 (s, 3 H); 2.31 (t, 8.4 Hz, 2 H); 2.80 (dd, 12.4 Hz, 3.4 Hz, 1 H); 3.19–4.28 (m, 31 H); 4.51 (m, 3 H); 5.09 (d, 4.8 Hz, 1 H). $^{13}$C-NMR (CD$_3$OD, 126.00 MHz) δ=15.53; 22.59; 26.03; 27.02; 30.14; 30.31; 30.36; 30.64; 34.79; 41.62; 51.96; 53.89; 58.97; 61.45; 61.79; 62.88; 64.10; 69.23; 69.57; 70.75; 71.02 (2×C); 71.88; 72.70; 73.16; 73.76; 74.61; 74.63; 76.76 (2×C); 77.22 (2×C); 77.43; 101.02; 102.48; 104.36; 105.13; 175.41; no resolution of the remaining signals.

EXAMPLE B7

Preparation of Compound No. (93)

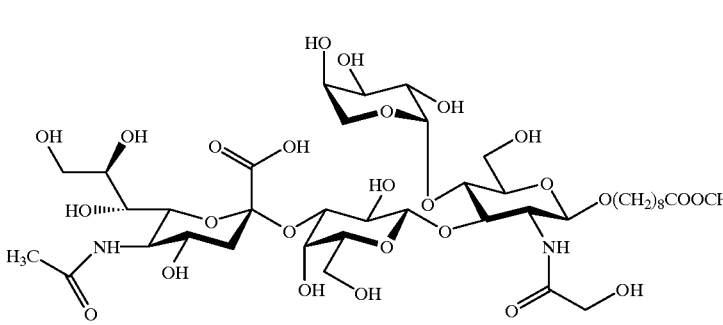
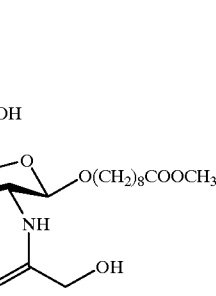

(93)

(a) 13 mg (61%) of disaccharide No. (96) are obtained according to Example B2.1(a) from 15 mg (37 μmol) (in this case the buffer solution comprises 8% of DMSO (vol/vol)) of compound No. (95) and 34 mg (56 μmol) of UDP-D-galactose.

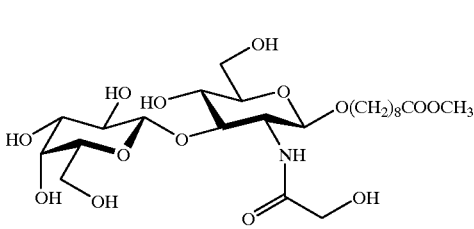

(96)

$^1$H-NMR (CD$_3$OD-D$_2$O-CDCl$_3$, 400.13 MHz) δ=1.22 (m, 8 H); 1.49 (m, 4 H); 2.26 (t, 7.5 Hz, 2 H); 3.27–3.84 (m, 17 H); 3.96 (q, 15.2 Hz, 2 H); 4.28 (d, 8.6 Hz, 1 H); 4.52 (d, 8.6 Hz, 1 H). $^{13}$C-NMR (CD$_3$OD-D$_2$O-CDCl$_3$, 100.6 MHz) DEPT δ=25.76; 26.62; 29.78; 29.93; 29.96; 30.22; 34.76; 52.49; 55.75; 62.28; 62.33; 62.45; 69.97; 70.28; 71.04; 72.15; 74.08; 76.72; 77.01; 83.54; 101.94; 104.87.

(b) 14 mg (79%) of compound No. (97) are obtained according to Example B1.1(b) from 12 mg (21 μmol) of compound No. (96) and 18 mg (29 μmol) of CMP-sia.

(t, 7.6 Hz, 2 H); 2.80 (dd, 11.6 Hz, 2.8 Hz, 1 H); 3.27 (m, 1 H); 3.33–3.85 (m, 22 H); 3.96 (dd, 3.7 Hz, 9.8 Hz, 1 H); 3.98 (q, 16.6 Hz, 2 H); 4.28 (d, 8.6 Hz, 1 H); 4.50 (d, 8.6 Hz, 1 H). $^{13}$C-NMR (CD$_3$OD, 100.6 MHz) δ=22.61; 26.01; 26.98; 30.11; 30.28; 30.32; 30.60; 34.79; 42.32; 51.64; 53.91; 55.63; 62.09; 62.68; 62.73; 62.82; 64.78; 68.80; 69.27; 70.16; 70.53; 70.62; 71.35; 73.22; 74.84; 77.03; 77.56; 84.49; 100.94; 102.22; 105.35; 174.75; 175.49; 176.02; 176.07.

(c) 14 mg (100%) of compound No. (93) are obtained according to Example B2.1(c) from 12 mg (14 μmol) of compound No. (97) and 14 mg (22 μmol) of GDP-D-arabinose. $^1$H-NMR (CD$_3$OD, 400.13 MHz) δ=1.14–1.28 (m, 8 H); 1.35–1.50 (m, 4 H); 1.56 (t, 12.4 Hz, 1 H); 1.89 (s, 3 H); 2.19 (t, 8.4 Hz, 2 H); 2.74 (dd, 12.4 Hz, 3.4 Hz, 1 H); 3.23–3.89 (m, 27 H); 3.99 (m, 2 H); 4.33 (d, 7.0 Hz, 1 H); 4.42 (d, 8.6 Hz, 1 H); 4.61 (broad d, 12.9 Hz, 2 H); 4.96 (d, 4.3 Hz, 1 H). $^{13}$C-NMR (CD$_3$OD, 100.6 MHz) δ=22.61; 26.02; 26.99; 30.11; 30.30; 30.33; 30.62; 34.79; 42.55; 51.99; 53.84; 56.81; 61.38; 62.13; 62.84; 63.03; 64.40; 64.82; 65.36; 68.29; 69.37; 70.29; 70.66; 71.03; 71.40; 73.17; 73.63; 74.22; 74.78; 77.35; 77.64; 77.80; 100.33; 100.88; 102.15; 104.29; 174.71; 175.44; 175.94; 176.09.

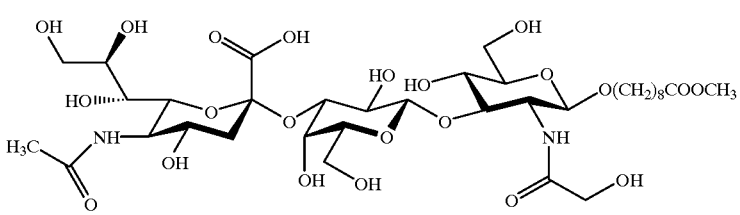

(97)

$^1$H-NMR (CD$_3$OD, 400.13 MHz) δ=1.19–1.32 (m, 8 H); 1.44–1.57 (m, 4 H); 1.63 (t, 11.6 Hz, 1 H); 1.95 (s, 3 H); 2.25

EXAMPLE B8.1

Preparation of Compound No. (52)

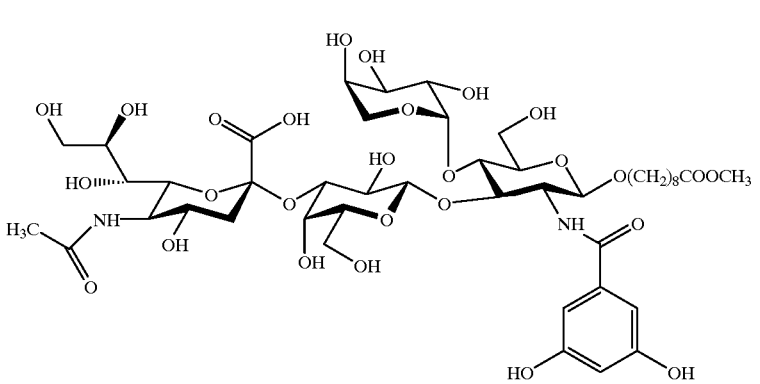
(52)

(a) 8.7 g (17.0 mmol) of benzyl-protected monosaccharide No. (54) are initially introduced into the reaction vessel together with 5.5 g (22 mmol) of mercury cyanide in 260 ml of dry toluene/nitromethane (vol/vol—1/1) and the mixture is stirred with triturated, active molecular sieve 4 Å (about 5 g) at RT for 30 minutes. 10.3 g (25.0 mmol) of per-O-acetylated α-galactosyl bromide, dissolved in 35 ml of toluene/nitromethane (see above) are then added drop-wise to this mixture and the mixture is heated at 50° C. for about 18 hours. After all the monosaccharide has reacted, the mixture is filtered carefully over Celite, the solvent is removed in a rotary evaporator and the residue which remains is chromatographed over silica gel (eluent: hexane/ethyl acetate—2/1). 9.1 g (64%) of disaccharide No. (55) are obtained.

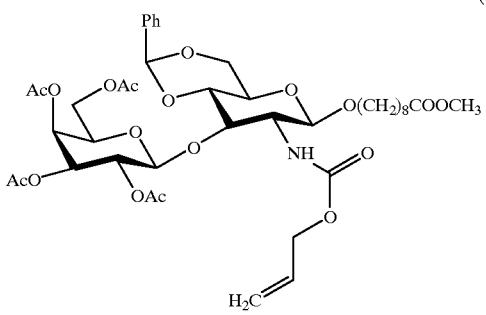
(55)

$^1$H-NMR (CDCl$_3$, 400.13 MHz) δ=1.22 (m, 8 H); 1.51 (m, 4 H); 1.88 (s, 3 H); 1.89 (s, 3 H); 1.91 (s, 3 H); 2.05 (s, 3 H); 2.23 (t, 7.6 Hz, 2 H); 3.06 (broad, 1 H); 3.41 (m, 2 H); 3.59 (m, 5 H); 3.71 (m, 2 H); 3.78 (dt, 6.1 Hz, 9.1 Hz, 1 H); 3.98 (dd, 6.6 Hz, 11.4 Hz, 1 H); 4.25 (dd, 6.1 Hz, 11.4 Hz, 1 H); 4.39 (m, 1 H); 4.50 (m, 2 H); 4.59 (d, 7.3 Hz, 1 H); 4.89 (dd, 3.6 Hz, 10.9 Hz, 1 H); 5.05 (m, 1 H); 5.13 (dd, 7.3 Hz, 10.9 Hz, 1 H); 5.19 (dq, 1.2 Hz, 11.5 Hz, 1 H); 5.22 (dd, 0.6 Hz, 3.0 Hz, 1 H); 5.27 (m, 1 H); 5.47 (s, 1 H); 5.86 (m, 1 H); 7.30 (m, 3 H); 7.40 (m, 2 H). $^{13}$C-NMR (CDCl$_3$, 62.90 MHz) δ=20.52 (2×C); 20.62 (2×C); 24.80; 25.65; 28.93; 29.0 (2×C); 29.38; 33.99; 51.44; 58.08; 60.70; 65.60; 65.87; 66.73; 68.70; 69.06; 70.27; 70.40; 70.97; 76.49; 78.63; 80.18; 101.01; 101.33; 117.88; 126.03 (2×C); 128.15 (2×C); 129.14; 132.44; 137.04; 155.43; 169.40; 170.06; 170.11; 170.24; 174.42.

(b) 9.1 g (10.7 mmol) of disaccharide No. (55) are dissolved in 100 ml of methylene chloride, and 5 ml of a 90% trifluoroacetic acid are added at room temperature. After about 6 hours, the mixture is neutralized with saturated sodium bicarbonate solution, diluted with ethyl acetate and extracted in succession with water and saturated sodium chloride solution. The organic phase is dried over sodium sulfate and evaporated. 7 ml of pyridine and 3.5 ml of acetic anhydride are added to the resulting residue and the mixture is stirred overnight at RT. The mixture is then diluted with ethyl acetate and extracted successively with 4 N hydrochloric acid, water and saturated sodium bicarbonate solution. After evaporation of the solvent, a yellow syrup remains, and is chromatographed over silica gel (eluent: petroleum ether/ethyl acetate—2/1). 6.9 g (76%) of disaccharide No. (56) are obtained.

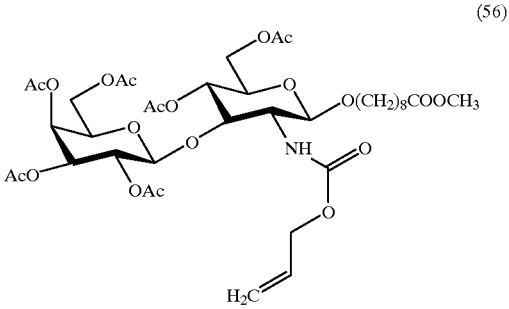
(56)

$^1$H-NMR (CDCl$_3$, 400.13 MHz) δ=1.22 (m, 8 H); 1.51 (m, 4 H); 1.93 (s, 3 H); 1.98 (s, 3 H); 2.00 (s, 3 H); 2.01 (s, 3 H); 2.09 (s, 3 H); 2.17 (s, 3 H); 2.24 (t, 7.6 Hz, 2 H); 3.10 (m, 1 H); 3.39 (dt, 6.0 Hz, 10.9 Hz, 1 H); 3.58 (m, 1 H); 3.60 (s, 3 H); 3.79 (m, 2 H); 4.04 (m, 3 H); 4.17 (dd, 6.0 Hz, 11.0 Hz, 1 H); 4.80 (m, 1 H); 4.52 (m, 3 H); 4.66 (m, 1 H); 4.88 (m, 2 H); 4.99 (m, 1 H); 5.01 (dd, 7.3 Hz, 11.5 Hz, 1 H); 5.19 (dq, 0.6 Hz, 12.1 Hz, 1 H); 5.28 (m, 2 H); 5.27 (m, 1 H); 5.90 (m, 1 H). $^{13}$C-NMR (CDCl$_3$, 62.90 MHz) δ=20.50; 20.61 (3×C); 20.67; 20.79; 24.79; 25.63; 28.91; 28.97; 29.01; 29.30; 33.99; 51.43; 58.02; 60.98; 62.44; 65.59; 66.76

(2×C); 69.00; 69.15; 70.00; 70.42; 70.95; 71.65; 100.55; 101.02; 117.91; 137.50; 155.55; 169.15; 169.27; 170.11; 170.19; 170.32; 170.75; 174.29.

(c) 4.0 g (4.7 mmol) of disaccharide No. (56) are dissolved in 60 ml of absolute THF under argon at RT and 5.6 ml of diethyl malonate and 0.4 g (0.3 mmol) of tetrakis-(triphenyl)-palladium are added in succession. After about 1 hour, the solvent is evaporated off and the residue which remains is chromatographed over silica gel. 3.1 g (89%) of amine No. (57) are obtained.

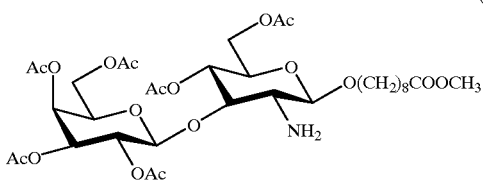
(57)

$^1$H-NMR (CDCl$_3$, 250.13 MHz) δ=1.33 (m, 8 H); 1.60 (m, 4 H); 1.99 (s, 3 H); 2.05 (m, 12); 2.13 (s, 3 H); 2.29 (t, 7.6 Hz, 2 H); 2.92 (dd, 7.5 Hz, 8.2 Hz, 1 H); 3.46 (dt, 6.9 Hz, 10.3 Hz, 1 H); 3.58 (m, 1 H); 3.67 (s, 3 H); 3.89 (m, 2 H); 4.14 (m, 6 H); 4.73 (d, 7.6 Hz, 1 H); 4.99 (m, 2 H); 5.15 (dd, 7.6 Hz, 11.7 Hz, 1 H); 5.35 (m, 1 H). $^{13}$C-NMR (CDCl$_3$, 62.90 MHz) δ=20.50; 20.60 (3×C); 20.77; 20.81; 24.82; 25.83; 28.98; 29.09 (2×C); 29.42; 33.99; 51.40; 57.05; 60.91; 62.51; 66.74; 68.70; 69.52; 70.16; 70.58; 70.97; 72.04; 83.53; 101.45; 103.12; 169.03; 169.30; 170.13; 170.29; 170.75; 174.44.

(d) 287 mg (98%) of amide are obtained according to Example A8 from 56 mg (360 µmol) of 3,5-dihydroxybenzoic acid and 250 mg (330 µmol) of amine No. (57) in the presence of 155 mg of HBPyU, after chromatography of the reaction mixture over silica gel (eluent: methylene chloride/methanol—15/0.5), and the product is immediately deacetylated with sodium methanolate. Renewed chromatography over silica gel (eluent: methylene chloride/methanol/water—6/4/1) gives 137 mg (65%) of disaccharide No. (58).

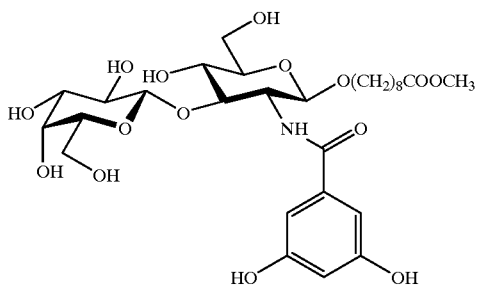
(58)

$^1$H-NMR (CD$_3$OD 400.13 MHz) δ=1.08 (m, 8 H); 1.41 (m, 4 H); 2.18 (t, 7.6 Hz, 2 H); 3.19–3.89 (m, 17 H); 4.22 (d, 8.6 Hz, 1 H); 4.56 (broad d, 9.0 Hz, 1 H); 6.30 (t, about 2.0 Hz, 1 H); 6.64 (d, about 2.0 Hz, 2 H). $^{13}$C-NMR (CD$_3$OD, 100.61 MHz) δ=26.53; 27.13; 30.04; 30.23; 30.30; 30.61; 34.76; 51.95; 56.90; 62.39; 62.71; 70.14; 70.69; 70.77; 72.32; 74.36; 76.98; 77.45; 84.24; 102.33; 105.21; 106.57; 107.03 (2×C); 138.03; 159.70 (2×C); 171.39; 176.19.

(e) 43 mg (87%) of compound No. (59) are obtained according to Example B1.1(b) from 34 mg (53 µmol) of compound No. (58) and 50 mg (75 µmol) of CMP-sia.

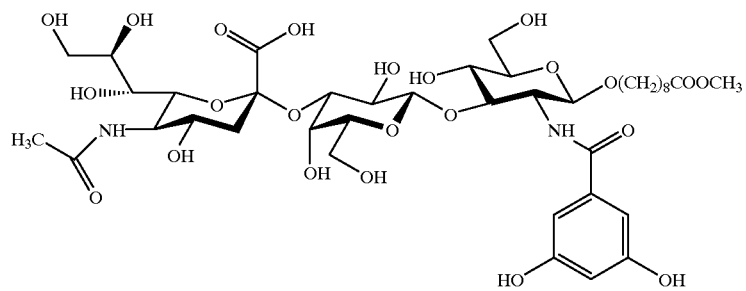
(59)

$^1$H-NMR (CD$_3$OD, 400.13 MHz) δ=1.12 (m, 8 H); 1.46 (m, 4 H); 1.72 (broad t, 11.6 Hz, 1 H); 1.98 (s, 3 H); 2.22 (t, 7.6 Hz, 2 H); 2.74 (dd, 11.6 Hz, 2.8 Hz, 1 H); 3.33 (m, 1 H); 3.42–3.75 (m, 16 H); 3.83–3.97 (m, 7 H); 4.38 (d, about 8.6 Hz, 1 H); 4.59 (broad d, about 8.6 Hz, 1 H); 6.37 (t, about 2.0 Hz, 1 H); 6.68 (d, about 2.0 Hz, 2 H). $^{13}$C-NMR (CD$_3$OD, 100.61 MHz) δ=22.74; 25.99; 27.14; 30.09; 30.30; 30.36; 30.67; 34.80; 41.40; 51.97; 53.91; 56.71; 62.61; 62.78; 63.96; 69.34; 69.71; 70.67; 70.78; 70.83; 72.89; 74.85; 76.68; 77.30; 77.45; 82.95; 101.56; 102.56; 104.07; 106.74; 107.70 (2×C); 138.23; 159.71; 171.33; 175.21; 175.48; 176.23.

(f) 10 mg (72%) of compound No. (52) are obtained according to Example B2.1(c) from 12 mg (13 µmol) of compound No. (59) and 14 mg (17 μmol) of GDP-D-arabinose. $^1$H-NMR (CD$_3$OD, 400.13 MHz) δ=1.10 (m, 8 H); 1.41 (m, 4 H); 1.65 (broad t, 11.0 Hz, 1 H); 1.92 (s, 3 H); 2.18 (t, 7.6 Hz, 2 H); 2.72 (dd, 2.8 Hz, 11.6 Hz, 1 H); 3.33–3.90 (m, 28 H); 4.37 (broad t, 6.3 Hz, 1 H); 4.48 (d, 8.6 Hz, 1 H); 4.56 (d, 8.6 Hz, 1 H); 5.01 (d, 4.3 Hz, 1 H); 6.35 (t, about 3.0 Hz, 1 H); 6.64 (d, about 3 Hz, 2 H). $^{13}$C-NMR (CD$_3$OD, 100.61 MHz) δ=22.68; 25.96; 27.14; 30.03; 30.19; 30.30; 30.62; 34.83; 41.91; 52.15; 53.81; 58.37; 61.45; 62.98; 64.10; 65.50; 68.88; 69.42; 69.66; 70.24; 70.33; 70.88; 70.94; 71.00; 72.84; 74.85 (2×C); 76.15; 76.43; 77.11; 77.76; 100.00; 100.34; 101.52; 101.95; 103.27; 106.92 (2×C); 138.15; 159.70 (2×C); 171.31; 174.84; 175.66; 176.62.

EXAMPLE B8.2

Preparation of Compound No. (60)

8 mg (32%) of compound No. (60) are obtained according to Example B8.1(f) from 23 mg (24 μmol) of compound No. (59) and 17 mg (28 μmol) of GDP-2-amino-fucose. $^1$H-NMR (CD$_3$OD, 400.13 MHz) δ=1.16 (m, 11 H); 1.46 (m, 4 H); 1.68 (broad t, 11.0 Hz, 1 H); 1.96 (s, 3 H); 2.22 (t, 7.6 Hz, 2 H); 2.77 (dd, 2.8 Hz, 11.6 Hz, 1 H); 3.23 (dd, 5.5 Hz, 12.4 Hz, 1 H); 3.34 (m, 1 H); 3.39–3.95 (m, 24 H); 4.50–4.66 (m, 3 H); 5.26 (d, 4.3 Hz, 1 H); 6.35 (t, about 3.0 Hz, 1 H); 6.66 (d, about 3 Hz, 2 H). $^{13}$C-NMR (CD$_3$OD, 100.61 MHz) δ=16.66; 22.61; 26.01; 27.21; 30.10; 30.28; 30.71; 34.81; 41.90; 51.97; 52.50; 53.88; 59.21; 62.66; 63.04; 64.51; 68.14; 68.55; 69.15; 69.44; 69.91; 70.81; 71.03; 72.55; 73.00; 73.97; 77.02 (2×C); 76.58 (2×C); 77.98; 95.46; 101.40; 101.82; 103.19; 106.84 (2×C); 106.97; 138.25; 159.89 (2×C); 171.46; 174.78; 175.53; 176.24.

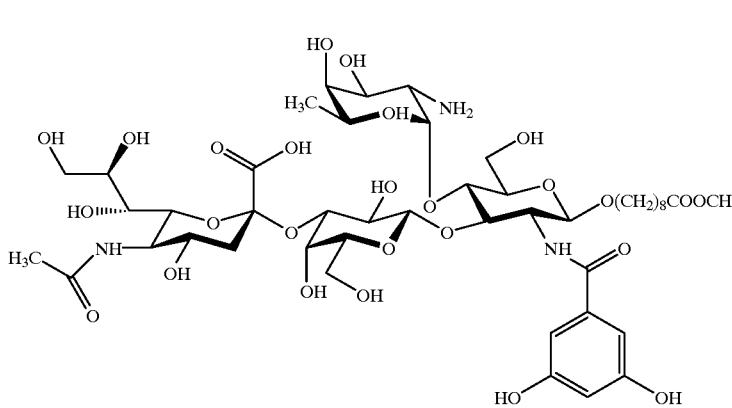

(60)

EXAMPLE B8.3

Preparation of Compound No. (68)

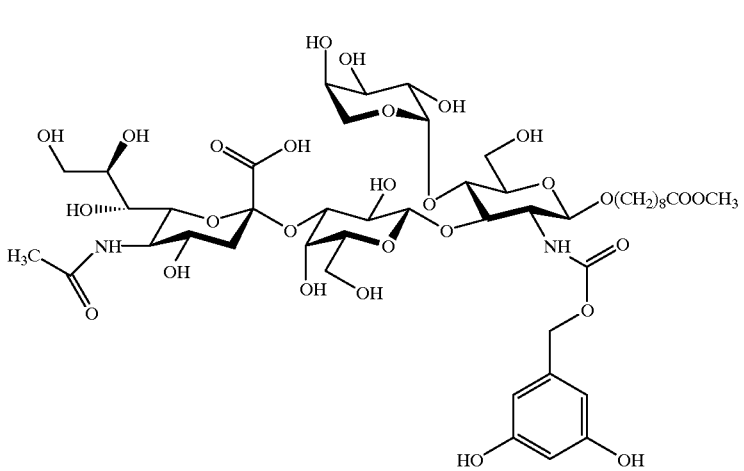

(68)

(a) 66 mg of 3,5-di-O-acetoxybenzyl alcohol are cooled to 0° C. in 3 ml of dry toluene under argon. 1.6 ml of a 20% phosgene solution (toluene) are then added to this mixture and the mixture is stirred at RT for about 2.5 hours and then evaporated to dryness. 250 mg (327 µmol) of amine No. (57), dissolved in 3 ml of dry DMF, are immediately added to this residue, 50 ml (1.2 equivalents) of triethylamine are added and the mixture is stirred overnight at RT. Thereafter, the solvent is evaporated off and the residue is chromatographed over silica gel (eluent: methylene chloride/methanol—10/0.4). 229 mg (77%) of peracetylated adduct are obtained, and are immediately dissolved in 5 ml of dry methanol, and 0.5 ml of a freshly prepared 0.1% sodium methanolate solution is added. Customary working up gives 37 mg (25%) of carbamate No. (69).

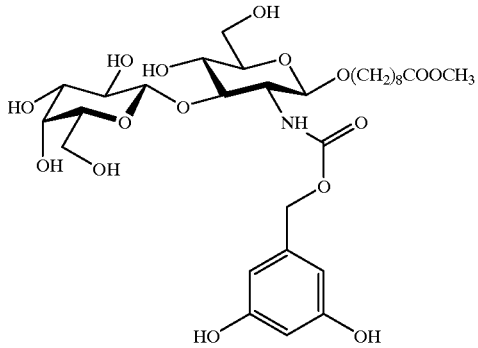

(69)

$^1$H-NMR (CD$_3$OD, 400.13 MHz) δ=1.28 (m, 8 H); 1.51 (m, 4 H); 2.24 (t, 7.5 Hz, 2 H); 3.24–3.86 (m, 17 H); 4.33 (d, 8.6 Hz, 1 H); 4.44 (broad d, 8.6 Hz, 1 H); 4.91 (m, 2 H); 6.15 (t, about 2.0 Hz, 1 H); 6.27 (d, about 2.0 Hz, 2 H). $^{13}$C-NMR (CD$_3$OD, 100.60 MHz) δ=25.99; 26.95; 30.10; 30.23; 30.30; 30.53; 34.80; 51.98; 58.13; 62.53; 62.70; 67.46; 70.29; 70.59; 70.86; 72.56; 74.44; 76.99; 77.42; 84.14; 102.64; 102.98; 105.09; 106.96 (2×C); 140.40; 159.61 (2×C); 176.17; no resolution of the remaining signals.

(b) 32 mg (61%) of compound No. (70) are obtained according to Example B1.1(b) from 37 mg (55 µmol) of compound No. (69) and 48 mg (73 µmol) of CMP-sia.

$^1$H-NMR (CD$_3$OD, 400.13 MHz) δ=1.24 (m, 8 H); 1.51 (m, 4 H); 1.76 (broad t, 11.6 Hz, 1 H); 1.98 (s, 3 H); 2.25 (t, 7.6 Hz, 2 H); 2.80 (dd, 11.6 Hz, 2.8 Hz, 1 H); 3.34–4.07 (m, 24 H); 4.43 (m, 2 H); 4.98 (m, 2 H); 6.16 (t, about 2.0 Hz, 1 H); 6.29 (d, about 2.0 Hz, 2 H); $^{13}$C-NMR (CD$_3$OD, 100.61 MHz) δ=22.71; 25.99; 26.95; 30.11; 30.24; 30.29; 30.53; 34.80; 41.79; 51.99; 53.93; 58.22; 62.74 (2×C); 64.29; 67.82; 68.11; 69.27; 69.35; 69.92; 70.50; 70.86 (2×C); 72.61; 74.87; 76.67; 77.38 (2×C); 83.79; 101.19; 102.54; 103.03; 104.49; 107.06 (2×C); 140.42; 159.55 (2×C); 175.51; 176.20; no resolution of the remaining signals.

(c) 9 mg (64%) of compound No. (68) are obtained according to Example B2.1(c) from 12 mg (12 µmol) of compound No. (70) and 11 mg (17 µmol) of GDP-D-arabinose. $^1$H-NMR (CD$_3$OD, 400.13 MHz) δ=1.19 (m, 8 H); 1.46 (m, 4 H); 1.65 (broad t, 11.0 Hz, 1 H); 1.92 (s, 3 H); 2.20 (t, 7.6 Hz, 2 H); 2.78 (dd, 2.8 Hz, 11.6 Hz, 1 H); 3.22–3.94 (m, 28 H); 4.09 (broad t, 8.8 Hz, 1 H); 4.39 (broad d, 8.6 Hz, 1 H); 4.56 (broad d, 8.6 Hz, 1 H); 4.98 (m, 3 H); 6.09 (t, about 3.0 Hz, 1 H); 6.28 (d, about 3 Hz, 2 H). $^{13}$C-NMR (CD$_3$OD, 100.61 MHz) δ=22.61; 26.01; 26.96; 30.12; 30.25; 30.29; 30.56; 34.82; 42.09; 51.98; 53.95; 61.54; 63.25; 64.30; 65.70; 67.62; 68.12; 69.18; 69.48; 69.90; 70.38; 70.84; 71.03 (2×C); 72.66; 74.52; 74.97; 76.17; 77.00; 77.15; 77.66; 100.21; 101.31; 102.18; 103.34; 103.68; 107.72 (2×C); 140.58; 159.60 (2×C); 175.15; 175.47; 176.21; no resolution of the remaining signals.

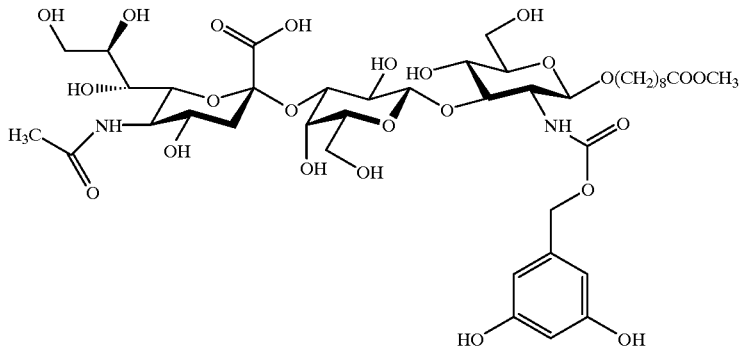

(70)

EXAMPLE B8.4

Preparation of Compound No. (71)

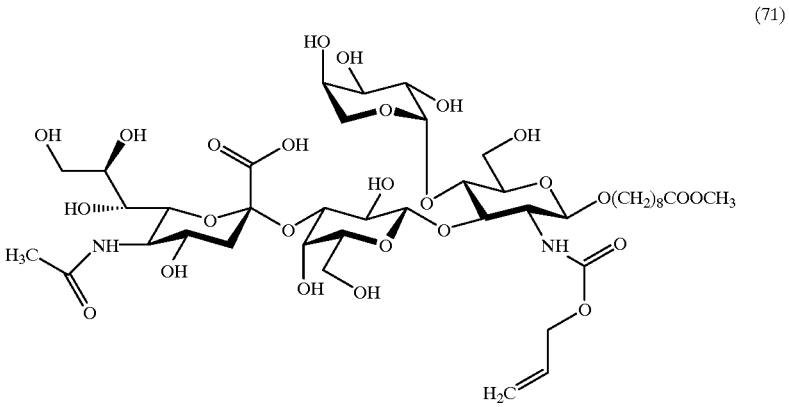

(a) 550 mg of peracetylated compound No. (56) are dissolved in 25 ml of dry methanol and the solution is treated with 0.5 ml of a 0.1% sodium methanolate solution. After about 1 h at RT, the mixture is neutralized with DOWEX 50×8 (H$^+$ form) and filtered and the solvent is evaporated. Chromatography of the residue over silica gel (eluent: methylene chloride/methanol—9/1) gives 350 mg (82%) of disaccharide No. (72).

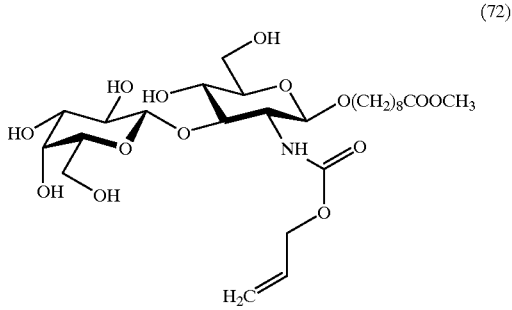

$^1$H-NMR (CD$_3$OD, 250.13 MHz) δ=1.18 (m, 8 H); 1.45 (m, 4 H); 2.19 (t, 7.6 Hz, 2 H); 3.14–3.84 (m, 17 H); 4.32 (d, 8.6 Hz, 1 H); 4.42 (m, 2 H); 5.05 (m, 1 H); 5.80 (m, 1 H). $^{13}$C-NMR (CD$_3$OD, 62.90 MHz) δ=25.97; 26.94; 30.05; 30.22; 30.27; 30.51; 34.80; 52.17; 58.48; 62.58 (2×C); 66.70; 70.14 H; 70.49; 70.88; 72.66; 74.41; 76.99; 77.27; 84.64; 102.98; 105.10; 117.62; 134.34; 159.73; 176.41.

(b) 36 mg (71%) of compound No. (73) are obtained according to Example B1.1(b) from 34 mg (56 μmol) of compound No. (72) and 49 mg (74 μmol) of CMP-sia.

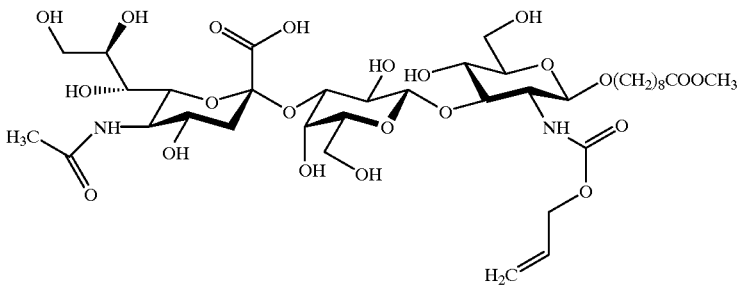

$^1$H-NMR (CD$_3$OD, 250.13 MHz) δ=1.23 (m, 8 H); 1.49 (m, 4 H); 1.67 (broad t, 11.6 Hz, 1 H); 1.93 (s, 3 H); 2.22 (t, 7.6 Hz, 2 H); 2.75 (dd, 11.6 Hz, 2.8 Hz, 1 H); 3.16–3.90 (m, 23 H); 3.94 (dd, 10.3 Hz, 3.4 Hz, 1 H); 4.30–4.62 (m, 4 H); 5.10 (m, 1 H); 5.23 (m, 1 H); 5.86 (m, 1 H). $^{13}$C-NMR (CD$_3$OD, 62.98 MHz) δ=22.68; 26.02; 27.01; 30.12; 30.30; 30.35; 30.60; 34.78; 41.77; 51.98; 53.95; 57.74; 62.71 (2×C); 64.25; 66.59; 69.09; 69.32; 69.83; 70.46; 70.76; 72.84; 74.89; 76.86; 77.40 (3×C); 83.91; 101.23; 102.91; 104.54; 117.43; 134.65; 158.92; 175.47; 176.02; 176.53.

(c) 18 mg (82%) of compound No. (71) are obtained according to Example B2.1(c) from 19 mg (22 μmol) of compound No. (73) and 18 mg (29 μmol) of GDP-D-arabinose. $^1$H-NMR (CD$_3$OD, 250.13 MHz) δ=1.21 (m, 8 H); 1.49 (m, 4 H); 1.67 (broad t, 12.4 Hz, 1 H); 1.93 (s, 3 H); 2.24 (t, 8.4 Hz, 2 H); 2.76 (dd, 12.4 Hz, 3.4 Hz, 1 H); 3.24–3.96 (m, 22 H); 4.08 (broad t, 6.4 Hz, 1 H); 4.33–4.70 (m, 5 H); 5.00 (d, 4.8 Hz, 1 H); 5.13 (m, 1 H); 5.25 (m, 1 H); 5.89 (m, 1 H). $^{13}$C-NMR (CD$_3$OD, 62.90 MHz) δ=22.68; 25.98; 26.95; 30.06; 30.26; 30.57; 30.89; 34.82; 42.22; 52.15; 53.87; 59.71; 61.45; 63.03; 64.49; 65.32;

66.91; 68.08; 68.64; 69.78; 70.17; 70.27; 70.92 (2×C); 73.15; 74.79; 74.80; 76.42; 77.12; 77.51; 100.60; 101.56; 102.85; 104.15; 118.21; 134.61; 175.04; 175.63; 176.21; no resolution of the remaining signals.

EXAMPLE B8.5

Preparation of Compound No. (82)

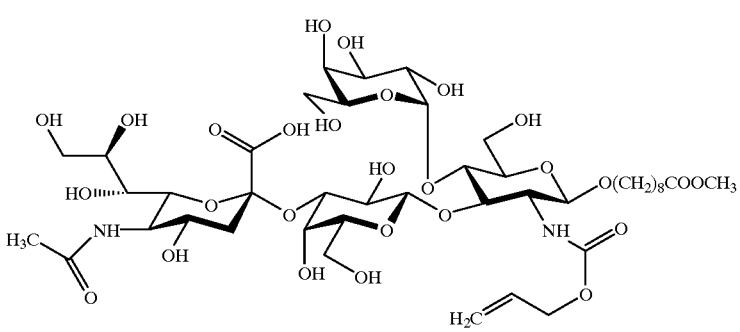

(82)

27 mg (77%) of compound No. (82) are obtained according to Example B8.4(c) from 30 mG (34 μmol) of compound No. (73) and 31 mg (47 μmol) of GDP-L-galactose. $^1$H-NMR (CD$_3$OD, 400.13 MHz) δ=1.15–1.33 (m, 8 H); 1.40–1.56 (m, 4 H); 1.68 (t, 12.4 Hz, 1 H); 1.94 (s, 3 H); 2.23 (t, 8.4 Hz, 2 H); 2.72 (dd, 12.4 Hz, 3.4 Hz, 1 H); 3.28–3.96 (m, 29 H); 4.03 (broad t, 8.8 Hz, 1 H); 4.35–4.71 (m, 4 H); 4.99 (d, 4.8 Hz, 1 H); 5.12 (m, 1 H); 5.25 (m, 1 H); 5.88 (m, 1 H). $^{13}$C-NMR (CD$_3$OD, 100.6 MHz) δ=22.67; 26.01; 27.02; 30.12; 30.32 (2×C); 30.64; 34.79; 41.95; 51.99; 53.97; 59.37; 61.33; 62.45; 62.70; 64.13; 66.60; 68.80; 69.29; 69.71; 70.28; 70.78 (2×C); 70.86; 71.10 (2×C); 72.65; 74.22; 74.90; 76.44; 77.17; 77.37; 78.37; 99.81; 101.31; 102.37; 104.28; 117.71; 134.77; 158.80; 175.10; 175.53; 176.04.

EXAMPLE B8.6

Preparation of Compound No. (98)

nol (60 ml) at RT, and 0.50 g (1.2 mmol) of DPPB, 1.5 g (11.3 mmol) of sodium thiophenolate and 0.30 g (0.3 mmol) of Pd(dba)$_2$ (Aldrich) are added in succession under an argon atmosphere. After the mixture has been stirred overnight, the solvents are evaporated off and the residue is chromatographed over silica gel (eluent: methylene chloride/methanol—5/1). 2.23 g (64%) of amine No. (99) are obtained.

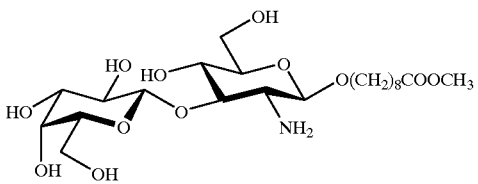

(99)

$^1$H-NMR (CD$_3$OD-CDCl$_3$, 400.13 MHz) δ=1.29–1.44 (m, 8 H); 1.56–1.69 (m, 4 H); 2.33 (t, 7.5 Hz, 2 H); 2.80 (broad t, 7.4 Hz, 1 H); 3.35 (m, 1 H); 3.44–3.96 (m, 15 H); 4.31 (d, 8.6 Hz, 1 H); 4.43 (d, 8.6 Hz, 1 H).

(b) 62 mg (49%) of disaccharide No. (100) are obtained according to Example B8.3(a) from 100 mg (195 μmol) of amine No. (99) and 37 mg (235 μmol) of 5-fluorosalicylic acid in the presence of 33 μl (235 mmol) of triethylamine and 89 mg (235 μmol) of HBTU instead of HBPyU in 3 ml

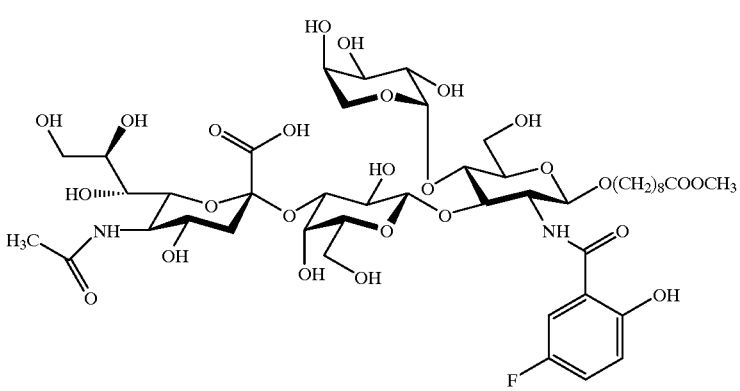

(98)

(a) 4.08 g (6.8 mmol) of disaccharide No. (72) are dissolved in a solvent mixture of THF (160 ml) and methaof dry DMF. Compound No. (100) can also be obtained analogously to Example B8.3(a) from amine No. (57) and 5-fluorosalicylic acid and subsequent deacetylation with sodium methanolate, in an overall yield of 82%.

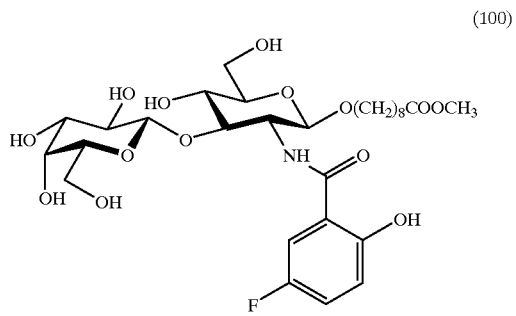

(100)

$^1$H-NMR (CD$_3$OD-CDCl$_3$-D$_2$O, 400.13 MHz) δ=1.36–1.62 (m, 8 H); 1.79–1.93 (m, 4 H); 2.60 (t, 7.5 Hz, 2 H); 3.76–4.39 (m, 17 H); 4.69 (d, 8.6 Hz, 1 H); 5.09 (d, 8.6 Hz, 1 H); 7.26 (dd, 4.9 Hz, 8.0 Hz, 8.3 Hz, 1 H); 7.47 (dt, 3.2 Hz, 8.0 Hz, 1 H); 7.88 (dd, 3.1 Hz, 9.8 Hz, 1 H). $^{13}$C-NMR (CD$_3$OD-CDCl$_3$-D$_2$O, 100.6 MHz) δ=25.29; 26.28; 29.40; 29.50; 29.56; 29.82; 34.50; 52.00; 55.88; 61.71; 61.76; 69.21; 69.56; 70.72; 71.38; 73.34; 75.95; 76.13; 82.52; 101.44; 104.02; 114.06 (d, 25.7 Hz); 116.74 (d, 6.6 Hz); 119.55 (d, 7.7 Hz); 121.26 (d, 23.5 Hz); 155.67 (d, 234.6 Hz); 157.17; 170.00; 175.69.

(c) 20 mg (46%) of compound No. (101) are obtained according to Example B1.1(b) (in this case the buffer solution comprises 9% of DMSO) from 30 mg (46 μmol) of compound No. (100) and 40 mg (64 μmol) of CMP-sia.

10.3 Hz, 1 H). $^{13}$C-NMR (CD$_3$OD, 100.6 MHz) δ=22.44; 25.87; 26.99; 29.93; 30.14 (2×C); 30.42; 34.65; 41.63; 51.82; 53.74; 56.14; 62.39; 62.67; 63.99; 68.66; 69.29; 69.53; 70.60 (2×C); 70.77; 72.58; 74.72; 76.70; 77.33; 77.42; 81.87; 101.03; 102.54; 104.22; 114.53 (d, 24.5 Hz); 117.50; 119.78 (d, 7.6 Hz); 121.51 (d, 23.7 Hz); 156.49 (d, 235.8 Hz); 170.42; 174.96; 175.29; 175.93; no resolution of the remaining signals.

(d) 17 mg (75%) of compound No. (98) are obtained according to Example B2.1(c) from 20 mg (21 μmol) of compound No. (101) and 17 mg (28 μmol) of GDP-D-arabinose. $^1$H-NMR (CD$_3$OD, 400.13 MHz) δ=0.93–1.29 (m, 8 H); 1.35–1.48 (m, 4 H); 1.69 (broad t, 12.4 Hz, 1 H); 1.96 (s, 3 H); 2.19 (t, 8.4 Hz, 2 H); 2.74 (dd, 12.4 Hz, 3.4 Hz, 1 H); 3.31–3.98 (m, 27 H); 4.40 (broad t, 5.5 Hz, 1 H); 4.57 (m, 2 H); 4.68 (broad d, 8.6 Hz, 1 H); 5.05 (d, 4.3 Hz, 1 H); 6.91 (dd, 5.5 Hz, 10.3 Hz, 1 H); 7.10 (broad dt, 3.4 Hz, 8.1 Hz, 1 H); 7.48 (dd, 5.5 Hz, 10.3 Hz, 1 H). $^{13}$C-NMR (CD$_3$OD, 100.6 MHz) δ=22.54; 25.98; 27.12; 30.06; 30.25; 30.26; 30.57; 34.77; 41.89; 51.96; 53.91; 58.18; 61.57; 63.02; 64.01; 65.41; 70.40; 70.71 (3×C); 70.98; 71.20; 74.84; 76.38 (2×C); 77.23 (2×C); 100.34; 102.24 (2×C); 103.33; 115.00 (d, 24.3 Hz); 118.41; 119.93 (d, 7.6 Hz); 121.69 (d, 23.2 Hz); 156.72; 156.88 (d, 234.9 Hz); 176.05; no resolution of the remaining signals. $^{19}$F-NMR (CD$_3$OD, 376.5 MHz) δ=–126.6.

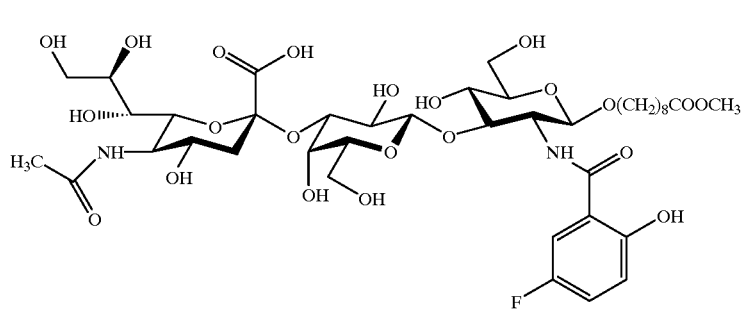

(101)

$^1$H-NMR (CD$_3$OD, 400.13 MHz) δ=0.90–1.21 (m, 8 H); 1.34–1.45 (m, 4 H); 1.62 (t, 11.6 Hz, 1 H); 1.92 (s, 3 H); 2.19 (t, 7.6 Hz, 2 H); 2.71 (dd, 11.6 Hz, 2.8 Hz, 1 H); 3.31 (m, 1 H); 3.37–3.71 (m, 17 H); 3.81–3.99 (m, 6 H); 4.40 (d, 8.6 Hz, 1 H); 4.58 (d, 8.6 Hz, 1 H); 6.83 (dd, 5.5 Hz, 10.3 Hz, 1 H); 7.08 (broad dt, 3.4 Hz, 8.1 Hz, 1 H); 7.48 (dd, 5.5 Hz,

EXAMPLE B8.7

Preparation of Compound No. (102)

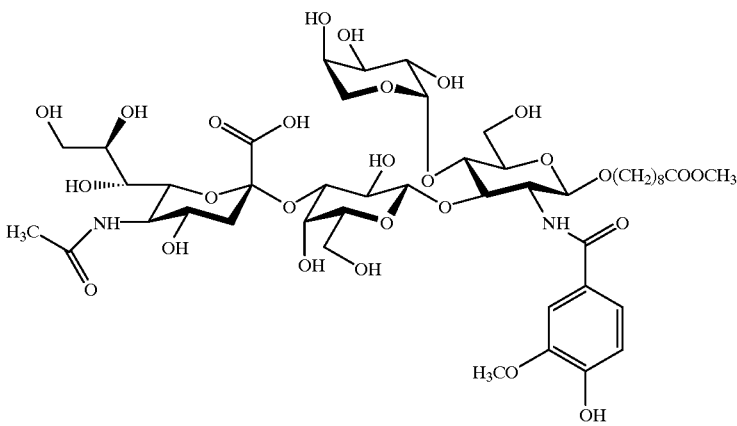

(a) 42 mg (28%) of amide No. (103) are obtained according to Example B8.6(b) from 44 mg (258 μmol) of vanillic acid and 100 mg (234 μmol) of compound No. (99) in the presence of 107 mg (282 μmol) of TBTU, instead of HBTU, and 40 μl (282 μmol) of triethylamine in 2 ml of dry DMF. Compound No. (103) can also be obtained from vanillic acid and amine No. (57) according to Example B8.1(d), in an overall yield of 27%.

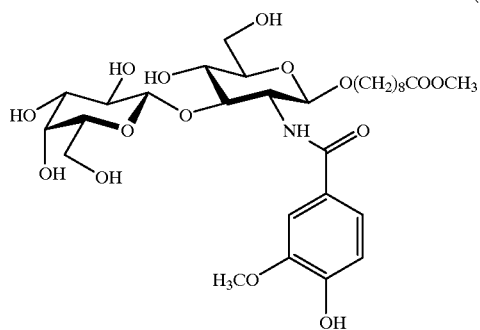

$^1$H-NMR (CD$_3$OD-CDCl$_3$, 400.13 MHz) δ=0.99–1.60 (m, 12 H); 2.20 (t, 7.5 Hz, 2 H); 3.33–3.92 (m, 19 H); 3.98 (broad t, 9.6 Hz, 1 H); 4.32 (d, 8.3 Hz, 1H); 4.66 (d, 8.2 Hz, 1 H); 6.81 (d, 8.3 Hz, 1 H); 7.36 (dd, 1.2 Hz, 7.2 Hz, 1H); 7.44 (d, 1.2 Hz, 1 H); $^{13}$C-NMR (CD$_3$OD-CDCl$_3$, 100.6 MHz) δ=25.65; 26.19; 29.53; 29.65 (2×C); 29.82; 35.38; 52.29; 56.56; 56.91; 61.21 (2×C); 69.67; 69.80; 71.09; 72.13; 74.01; 74.27; 76.95; 83.35; 102.12; 104.73; 112.12; 115.70; 122.06; 126.71; 148.51; 150.81; 170.63; 176.30.

(b) 22 mg (70%) of compound No. (104) are obtained according to Example B2.1(b) (in this case the buffer solution comprises 8% of DMSO (vol/vol)) from 22 mg (34 μmol) of compound No. (103) and 58 mg (88 μmol) of CMP-sia.

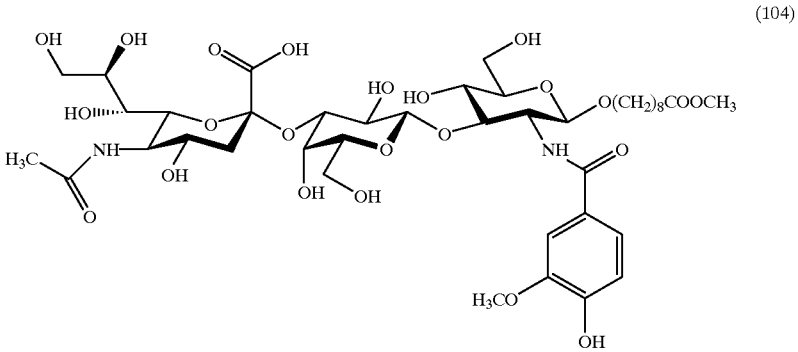

(104)

¹H-NMR (CD₃OD, 400.13 MHz) δ=0.93–1.29 (m, 8 H); 1.35–1.47 (m, 4 H); 1.65 (broad t, 11.6 Hz, 1 H); 1.95 (s, 3 H); 2.18 (t, 7.6 Hz, 2 H); 2.73 (dd, 11.6 Hz, 2.8 Hz, 1 H); 3.32 (m, 1 H); 3.37–3.71 (m, 18 H); 3.80–3.98 (m, 9 H); 4.37 (d, 8.6 Hz, 1 H); 4.60 (d, 8.6 Hz, 1 H); 6.81 (dd, 5.5 Hz, 10.3 Hz, 1 H); 7.33 (broad dt, 3.4 Hz, 8.1 Hz, 1 H); 7.41 (dd, 5.5 Hz, 10.3 Hz, 1 H). ¹³C-NMR (CD₃OD, 100.6 MHz) δ=21.33; 24.67; 25.85; 28.77; 29.03 (2×C); 29.33; 33.46; 40.43; 50.66; 52.59; 55.32 (2×C); 61.38; 61.51; 62.74; 67.60; 68.11; 68.32; 69.45; 69.54 (2×C); 71.45; 73.55; 75.58; 76.02; 76.22; 82.03; 99.91; 101.51; 102.98; 110.94; 114.62; 120.99; 125.90; 147.44; 149.96; 169.31; 173.79; 174.13; 174.80.

(c) 10 mg (60%) of compound No. (102) are obtained according to Example B2.1(c) from 14 mg (15 μmol) of compound No. (104) and 14 mg (22 μmol) of GDP-D-arabinose. ¹H-NMR (CD₃OD, 400.13 MHz) δ=0.89–1.23 (m, 8 H); 1.32–1.49 (m, 4 H); 1.59 (broad t, 11.0 Hz, 1 H); 1.92 (s, 3 H); 2.04 (t, 7.6 Hz, 2 H); 2.70 (dd, 11.6 Hz, 2.8 Hz, 1 H); 3.30–3.93 (m, 27 H); 4.30 (broad t, 9.0 Hz, 1 H); 4.48 (d, 8.6 Hz, 1 H); 4.56 (m, 2 H); 5.02 (d, 4.3 Hz, 1 H); 6.81 (d, 8.3 Hz, 1 H); 7.29 (dd, 2.1 Hz, 8.3 Hz, 1 H); 7.36 (d, 2.1 Hz, 1 H); ¹³C-NMR (CD₃OD, 100.6 MHz) δ=22.62; 27.19; 27.43; 30.47; 30.53; 30.65; 30.70; 34.49; 42.04; 51.83; 53.88; 56.65; 58.34; 61.54; 63.07; 63.86; 65.43; 68.57; 69.45 (2×C); 70.36; 70.42; 70.86; 70.94; 71.14; 72.55; 74.85; 74.90; 76.53; 76.75; 77.26; 77.51; 100.40; 101.13; 102.49; 103.39; 112.14; 116.25; 122.27; 126.91; 148.92; 151.48; 170.63; 174.98; 175.38; no resolution of the remaining signals.

EXAMPLE B8.8

Preparation of Compound No. (105)

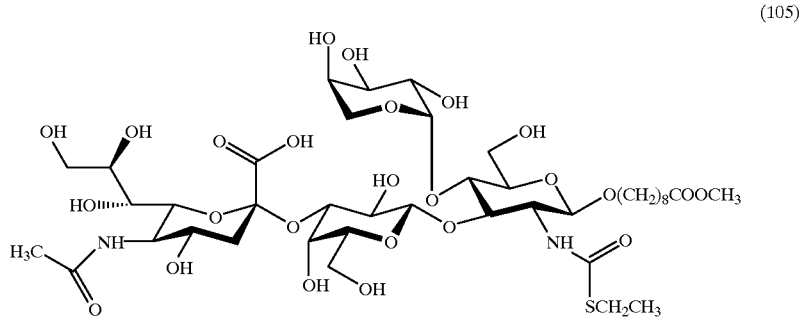

(105)

(a) 150 mg (293 μmol) of amine No. (99) are dissolved in 5 ml of dry DMF at RT, and 37 μl (352 μmol) of ethyl chlorothiolformate and 49 μl of triethylamine are added in succession. After the mixture has been stirred overnight, the solvent is evaporated off and the residue is chromatographed over silica gel (eluent: methylene chloride/methanol—4/1). 82 mg (46%) of amide No. (106) are obtained.

(106)

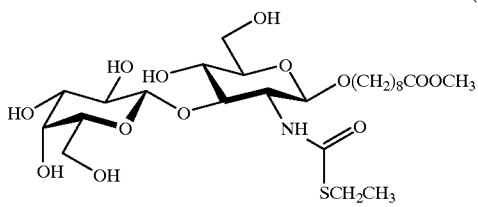

¹H-NMR (CD₃OD, 400.13 MHz) δ=1.15 (t, 6.7 Hz, 3 H); 1.21 (m, 8 H); 1.34 (m, 4 H); 2.20 (t, 7.5 Hz, 2 H); 2.73 (broad q, 6,7 Hz, 2 H); 3.20 (m, 1 H); 3.28–3.48 (m, 5 H); 3.52–3.81 (m, 11 H); 4.23 (d, 8.3 Hz, 1 H); 4.38 (d, 8.2 Hz, 1 H). ¹³C-NMR (CD₃OD-CDCl₃, 100.6 MHz) δ 16.6; 24.92; 25.94; 26.91; 30.00; 30.22 (2×C); 30.47; 34.81; 52.27; 57.76; 62.43; 62.48; 70.08; 70.46; 70.97 72.33; 74.29; 76.95; 77.18; 83.64; 102.34; 104.77.

(b) 24 mg (69%) of compound No. (107) are obtained according to Example B1.1(b) (in this case the buffer solution comprises 12% of DMSO (vol/vol)) from 23 mg (39 μmol) of compound No. (106) and 35 mg (53 μmol) of CMP-sia.

(107)

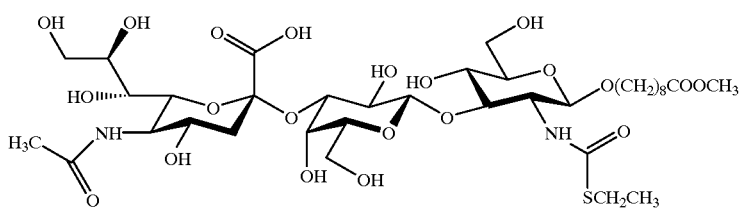

¹H-NMR (CD₃OD, 400.13 MHz) δ=1.20–1.36 (m, 11 H); 1.44–1.59 (m, 4 H); 1.72 (broad t, 11.6 Hz, 1 H); 1.97 (s, 3 H); 2.25 (t, 7.6 Hz, 2 H); 2.73–2.90 (m, 3 H); 3.23 (m, 1 H); 3.32–3.91 (m, 22 H); 3.99 (dd, 3.5 Hz, 10.6 Hz, 1 H); 4.36 (d, 8.6 Hz, 1 H); 4.45 (d, 8.6 Hz, 1 H). ¹³C-NMR (CD₃OD, 100.6 MHz) δ=16.35; 22.67; 24.94; 26.04; 27.04; 30.15; 30.15; 30.35; 30.37; 30.62; 34.80; 41.72; 51.98; 53.94; 57.80; 62.72 (2×C); 64.21; 69.12; 69.37; 69.71; 70.50; 70.78 (2×C); 72.71; 74.91; 76.91; 77.31; 77.46; 83.10; 101.24; 102.58; 104.25; 175.47 (2×C); 176.03.

(c) 14 mg (56%) of compound No. (105) are obtained according to Example B2.1(c) from 22 mg (25 μmol) of compound No. (107) and 20 mg (33 μmol) of GDP-D-arabinose. ¹H-NMR (CD₃OD, 400.13 MHz) δ=1.21–1.36 (m, 11 H); 1.44–1.59 (m, 4 H); 1.68 (broad t, 11.0 Hz, 1 H); 1.97 (s, 3 H); 2.26 (t, 7.6 Hz, 2 H); 2.71–2.94 (m, 3 H); 3.28–3.95 (m, 27 H); 4.17 (broad t, 10.0 Hz, 1 H); 4.48 (d, 7.3 Hz, 1 H); 4.57 (broad d, 7.6 Hz, 1 H); 5.01 (d, 4.3 Hz, 1 H). ¹³C-NMR (CD₃OD, 100.6 MHz) δ=16.67; 22.63; 24.96; 26.05; 27.05; 30.16; 30.36 (2×C); 30.65; 30.81; 42.14; 51.98; 53.95; 59.66; 61.48; 63.03; 64.23; 65.34; 68.59; 69.44; 69.66; 70.35 (2×C); 70.77; 70.96; 71.01; 72.50; 74.50; 74.89; 76.56; 76.70; 77.24; 77.53; 100.27; 100.96; 102.01; 103.58; 170.40; 175.12; 175.44; 176.03.

EXAMPLE B8.9

Preparation of Compound No. (83)

(83)

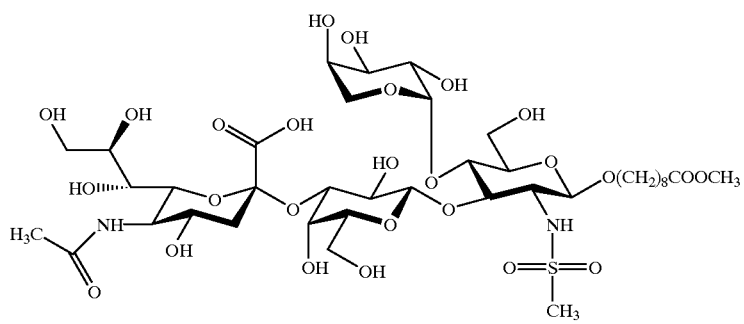

(a) 169 mg (98%) of peracetylated disaccharide are obtained according to Example B8.12(a) from 150 mg (196 μmol) of amine No. (57) and 18 ml (236 μmol) of mesyl chloride in 10 ml of methylene chloride in the presence of 40 μl (236 μmol) of N-ethyldiisopropylamine and 2.5 mg (20

μmol) of N,N-dimethylaminopyridine, instead of triethylamine; 52 mg (62 μmol) of this product are deacetylated according to Example B 8.5 with sodium methanolte to give disaccharide No. (84). 23 mg (64%) of sulfonamide are obtained.

(84)

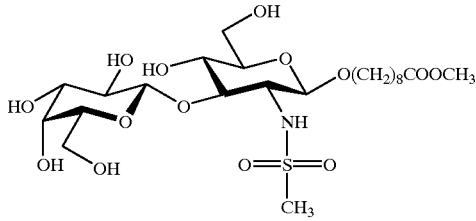

$^1$H-NMR (CD$_3$OD, 400.13 MHz) δ=1.14–1.29 (m, 8 H); 1.30–1.56 (m, 4 H); 2.19 (t, 7.6 Hz, 2 H); 2.90 (s, 3 H); 3.02–3.85 (m, 17 H); 4.21 (d, 8.6 Hz, 1 H); 4.31 (d, 8.6 Hz, 1 H). $^{13}$C-NMR (CD$_3$OD, 100.6 MHz) δ=25.97; 27.13; 30.08; 30.27; 30.30; 30.70; 34.77; 42.16; 51.97; 59.86; 62.49; 62.60; 70.17; 70.77; 71.00; 72.68; 74.42; 77.31; 77.36; 85.77; 102.72; 105.53; 176.41.

(b) 28 mg (94%) of compound No. (85) are obtained according to Example B1.1(b) from 20 mg (34 μmol) of compound No. (84) and 49 mg (55 μmol) of CMP-sia.

34.78; 41.84; 42.47; 51.97; 53.90; 59.77; 62.61; 62.74; 64.30; 69.03; 69.39; 69.95; 70.79; 71.00; 71.25; 71.30; 72.94; 74.81; 77.15; 77.36; 84.37; 100.18; 103.01; 104.89; 175.41; 176.03 (2×C).

(c) 12 mg (67%) of compound No. (83) are obtained according to Example B2.1(c) from 15 mg (17 μmol) of compound No. (85) and 17 mg (28 μmol) of GDP-D-arabinose. $^1$H-NMR (CD$_3$OD, 400.13 MHz) δ=1.18–1.32 (m, 8 H); 1.40–1.58 (m, 4 H); 1.65 (t, 12.4 Hz, 1 H); 1.95 (s, 3 H); 2.24 (t, 8.4 Hz, 2 H); 2.82 (dd, 12.4 Hz, 3.4 Hz, 1 H); 3.01 (s, 3 H); 3.28–3.95 (m, 27 H); 3.99 (dd, 3.4 Hz, 8.3 Hz, 1 H); 4.29 (d, 8.6 Hz, 1 H); 4.63 (broad d, 8.6 Hz, 1 H); 5.02 (d, 4.8 Hz, 1 H); the remaining signals are masked by the solvent. $^{13}$C-NMR (CD$_3$OD, 100.6 MHz) δ=22.63; 25.98; 27.10; 30.08; 30.27; 30.31; 30.68; 34.78; 42.46; 43.06; 51.99; 53.92; 61.24; 62.15; 63.10; 64.41; 65.49; 68.55; 69.39; 69.91; 70.24; 70.36; 70.97; 71.05; 71.41; 72.42; 73.64; 74.45; 74.83; 76.91; 77.27; 77.59; 100.42; 100.79; 102.90; 103.94; 174.80; 175.45; 176.04.

(85)

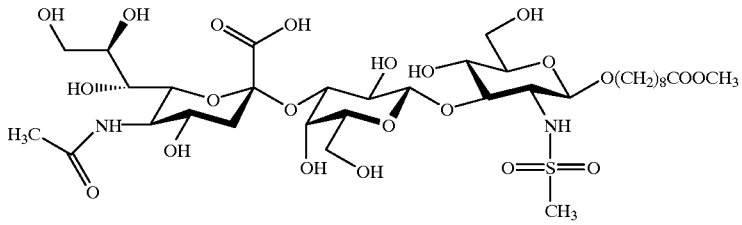

$^1$H-NMR (CD$_3$OD, 400.13 MHz) δ=1.21–1.38 (m, 8 H); 1.49–1.61 (m, 4 H); 1.72 (broad t, 12.4 Hz, 1 H); 1.96 (s, 3 H); 2.26 (t, 7.6 Hz, 2 H); 2.79 (broad dd, 12.4 Hz, 3.4 Hz, 1H)3.01 (s, 3 H); 3.13–3.95 (m, 24 H ); 4.28 (d, 8.6 Hz, 1 H); 4.40 (broad d, 8.6 Hz, 1 H). $^{13}$C-NMR (CD$_3$OD, 100.6 MHz) δ=22.72; 25.98; 27.05; 30.08; 30.26; 30.30; 30.66;

EXAMPLE B8.10

Preparation of Compound No. (89)

(89)

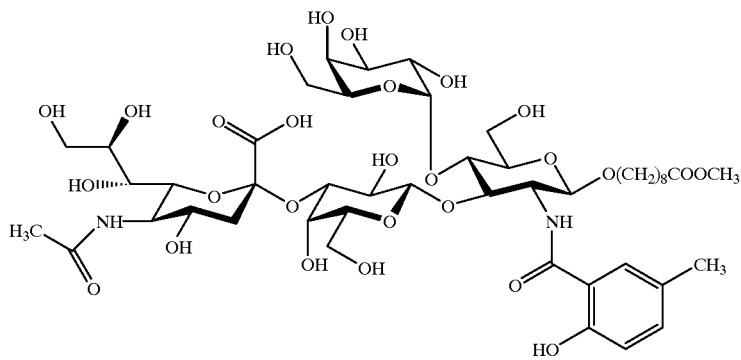

14 mg (84%) of compound No. (89) are obtained according to Example B2.1(c) from 14 mg (15 μmol) of compound No. (85) and 17 mg (28 μmol) of GDP-L-galactose. ¹H-NMR (CD₃OD, 400.13 MHz) δ=0.85–1.18 (m, 8 H); 1.34–1.47 (m, 4 H); 1.6 (t, 12.4 Hz, 1 H); 1.96 (s, 3 H); 2.20 (t, 8.4 Hz, 2 H); 2.26 (s, 3 H); 2.68 (dd, 12.4 Hz, 3.4 Hz, 1 H); 3.38 (m, 1 H); 3.41–4.00 (m, 27 H); 4.39 (broad t, 7.0 Hz, 1 H); 5.09 (d, 4.3 Hz, 1 H); 6.84 (d, 7.6 Hz, 1 H); 7.20 (dd, 1.4 Hz, 7.6 Hz, 1 H); 7.58 (d, 1.4 Hz, 1 H); the remaining signals are masked by the solvent. ¹³C-NMR (CD₃OD, 100.6 MHz) δ=20.73; 22.81; 25.75; 26.82; 29.75; 29.86; 29.96; 30.21; 34.76; 41.08; 52.49; 53.44; 61.31; 61.90; 62.63; 63.95; 68.81; 69.20; 69.31; 69.85; 70.51; 70.60; 70.66; 71.00; 71.10; 72.51; 74.25; 74.42; 75.81; 76.15; 76.88 (2×C); 77.24; 99.51; 101.16; 102.18; 103.65; 117.31; 118.38; 129.38; 129.92; 135.89; 157.72; 171.36; 175.10; 175.88; 177.13.

EXAMPLE B8.11

Preparation of Compound No. (61)

¹H-NMR (D₆-DMSO, 250.13 MHz) δ=1.18 (m, 8 H); 1.43 (m, 4 H); 2.26 (t, 7.5 Hz, 2 H); 3.17–3.79 (m, 17 H); 4.14 (m, 3 H); 4.48 (d, 8.6 Hz, 1 H); 4.55 (d, 8.6 Hz, 1 H); 4.67 (m, 2 H); 4.83 (s, 1 H); 4.88 (m, 1 H); 6.00 (s, 1 H); 8.75 (broad, 1 H). ¹³C-NMR (D₆-DMSO, 62.89 MHz) δ=24.51; 25.57; 28.52; 28.78; 28.86; 29.09; 33.34; 48.67; 54.48; 60.50 (2×C); 68.71; 68.76; 69.32; 70.40; 73.20; 75.70; 76.53; 84.49; 99.47; 100.39; 104.40; 146.61; 151.84; 160.96; 164.46; 173.50.

(b) 55 mg (73%) of compound No. (63) are obtained according to Example B1.1(b) (in this case the reaction mixture comprises 8% of DMSO (vol/vol)) from 50 mg (77 μmol) of compound No. (62) and 69 mg (104 μmol) of CMP-sia.

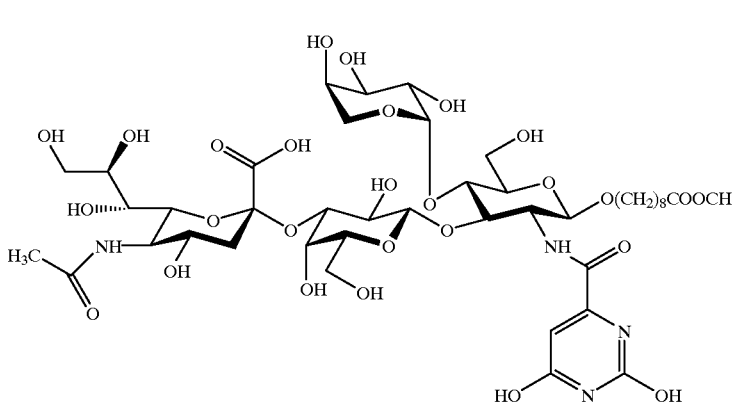

(61)

(a) 104 mg (63%) of amide No. (62) are obtained according to Example B8.1(d) from 45 mg (288 μmol) of orotic acid and 200 mg (262 μmol) of compound No. (57).

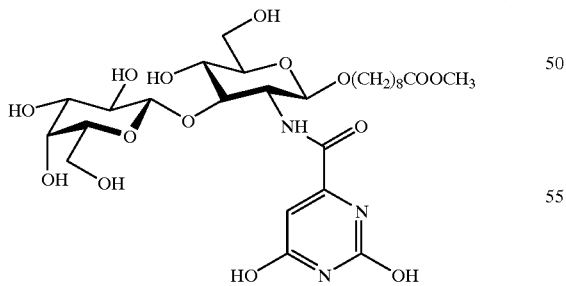

(62)

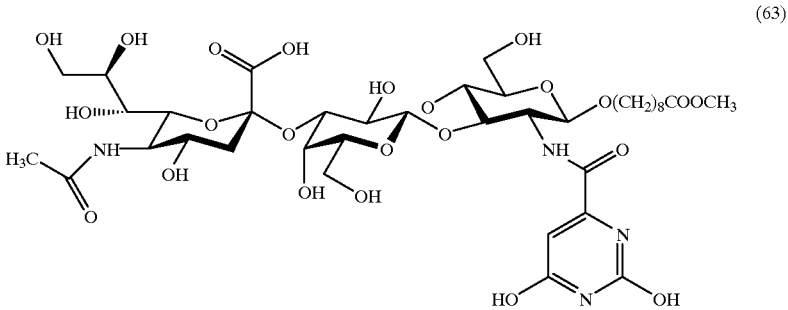

(63)

¹H-NMR (CD₃OD, 250.13 MHz) δ=1.18 (m, 8 H); 1.46 (m, 4 H); 1.66 (broad t, 11.0 Hz, 1 H); 1.93 (s, 3 H); 2.22 (t, 7.6 Hz, 2 H); 2.73 (broad d, 11.0 Hz, 1 H); 3.26–4.00 (m, 24 H); 4.31 (d, 8.6 Hz, 1 H); 4.52 (d, 8.6 Hz, 1 H); 6.10 (s, 1 H). ¹³C-NMR (CD₃OD, 62.89 MHz) δ=22.78; 26.00; 27.91; 30.10; 30.32; 30.44; 30.59; 34.77; 41.62; 52.02; 53.89; 56.57; 62.64 (2×C); 64.29; 69.01; 69.28; 69.84; 70.77 (3×C); 73.10; 74.86; 76.79; 77.36; 77.51; 84.17; 101.13 (2×C); 102.14; 105.35; 148.07; 153.97; 162.74; 167.10; 175.15; 175.46; 176.11.

(c) 11 mg (84%) of compound No. (61) are obtained according to Example B2.1(c) from 12 mg (12.0 μmol) of compound No. (63) and 10 mg (14 μmol) of GDP-D-arabinose. ¹H-NMR (CD₃OD, 400.13 MHz) δ=1.22 (m, 8 H); 1.48 (m, 4 H); 1.73 (t, 11.0 Hz, 1 H); 1.96 (s, 3 H); 2.25 (t, 7.6 Hz, 2 H); 2.75 (dd, 11.0 Hz, 3.4 Hz, 1 H); 3.33–3.94 (m, 27 H); 4.21 (t, 9.9 Hz, 1 H); 4.44 (d, 8.6 Hz, 2 H); 4.57 (m, 2 H); 5.06 (d, 4.8 Hz, 1 H); 6.10 (s, 1 H). ¹³C-NMR (CD₃OD, 100.60 MHz) δ=22.60; 26.00; 27.25; 30.13; 30.34; 30.44; 30.64; 34.79; 41.61; 51.97; 53.97; 58.29; 61.55; 63.15; 64.48; 65.40; 69.06; 69.66; 70.03; 70.35 (2×C); 70.76; 70.97; 71.06; 72.97; 74.44; 74.95; 76.57; 77.03; 77.38; 77.50; 100.23; 100.63; 102.09; 103.85; 104.06; no resolution of the remaining signals.

EXAMPLE B8.12

Preparation of Compound No. (74)

(a) 250 mg (327 μmol) of amine No. (57) are dissolved in 5 ml of methylene chloride at RT to give a clear solution, and 57 μl (490 μmol) of benzoyl chloride and 78 μl of triethylamine are added. After the mixture has been stirred overnight, the solvent is evaporated off and the residue is chromatographed over silica gel (eluent: ethyl acetate/hexane—6/4). 197 mg (70%) of peracetylated disaccharide are obtained and are dissolved in 2 ml of absolute methanol and deacetylated with 0.5 ml of a 0.5% sodium methanolate solution. After 1.5 h, the reaction mixture is evaporated and the residue is chromatographed over silica gel (eluent: methylene chloride/methanol/water—10/4/0.8). 76 mg (57%) of disaccharide No. (75) are obtained.

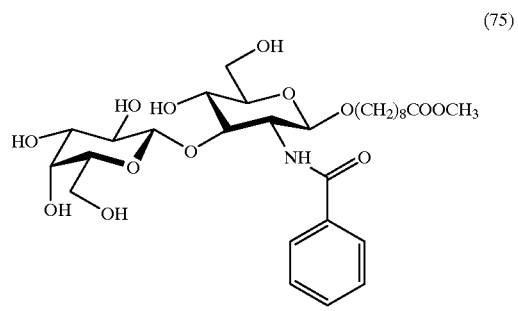

(75)

¹H-NMR (CD₃D-CDCl₃-D₂O, 400.13 MHz) δ=1.05 (very broad m, 8 H); 1.40 (m, 4 H); 2.18 (t, 7.6 Hz, 2 H); 3.31–3.40 (m, 2 H); 3.40–3.51 (m, 4 H); 3.59 (s, 3 H); 3.60 (dd, 4.4 Hz, 12.1 Hz, 1 H); 3.62–3.73 (m, 4 H); 4.26 (d, 8.6 Hz, 1 H); 4.66 (broad d, 8.6 Hz, 1 H); 7.39 (t, 8.8 Hz, 2 H); 7.46 (broad t, 8.8 Hz, 1 H); 7.76 (broad d, 8.8 Hz, 2 H).

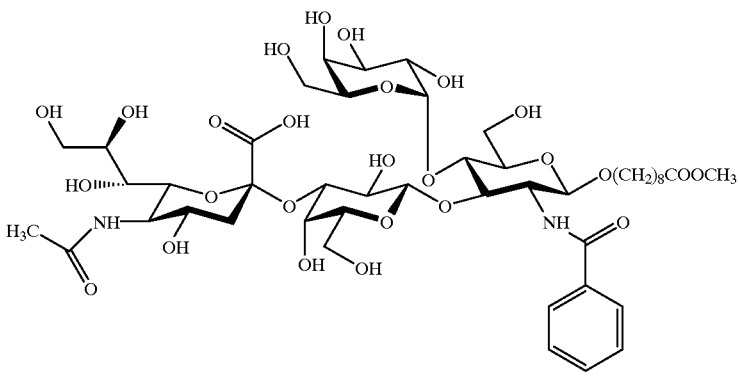

(74)

$^{13}$C-NMR (CD$_3$OD-CDCl$_3$-D$_2$O, 100.61 MHz) δ=25.65; 26.73; 29.70; 29.86; 29.92; 30.24; 34.72; 52.25; 56.66; 62.12; 62.27; 66.69; 70.23; 70.88; 71.90; 73.89; 76.53; 76.82; 83.40; 101.93; 104.71; 128.25 (2×C); 129.35 (2×C); 132.60; 135.26; 170.95; 176.31.

(b) 33 mg (72%) of compound No. (76) are obtained according to Example B1.1(b) from 31 mg (51 μmol) of compound No. (75) and 46 mg (69 μmol) of CMP-sia.

4.8 Hz, 1 H); 7.46 (m, 3 H); 7.77 (m, 2 H). $^{13}$C-NMR (CD$_3$OD, 100.61 MHz) δ=22.78; 25.80; 26.92; 29.80; 29.89; 30.05; 30.38; 34.76; 41.40; 52.39; 53.56; 62.00 (2×C); 62.69; 63.82; 68.96; 69.40; 69.99; 70.63; 70.73; 70.94; 71.03 (3×C); 72.50; 74.35; 74.56; 76.22; 76.98; 77.17; 99.63; 101.43; 104.01; 128.41 (2×C); 129.92 (2×C); 133.06; 135.32; 175.05; 175.89; 176.91; no resolution of the remaining signals.

(76)

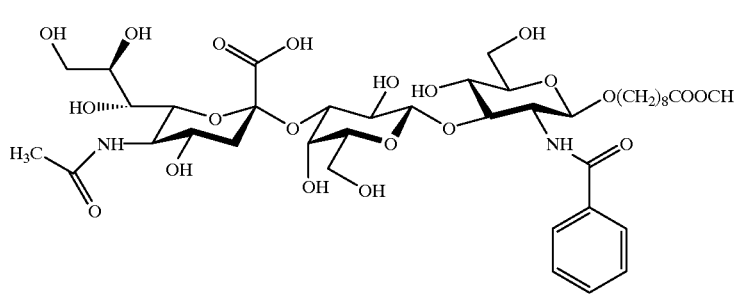

$^1$H-NMR (CD$_3$OD, 400.13 MHz) δ=1.10 (broad m, 8 H); 1.41 (m, 4 H); 1.64 (broad t, 11.6 Hz, 1 H); 1.93 (s, 3 H); 2.17 (t, 7.6 Hz, 2 H); 2.71 (dd, 11.6 Hz, 2.8 Hz, 1 H); 3.30–3.73 (m, 18 H); 3.80–3.94 (m, 6 H); 4.35 (d, 8.6 Hz, 1 H); 4.60 (broad d, 8.6 Hz, 1 H); 7.42 (m, 3 H); 7.77 (m, 1 H). $^{13}$C-NMR (CD$_3$OD, 100.61 MHz) δ=22.72; 25.87; 27.12; 30.05; 30.26; 30.28; 30.62; 34.76; 41.39; 51.97;

EXAMPLE B8.13

Preparation of Compound No. (86)

(86)

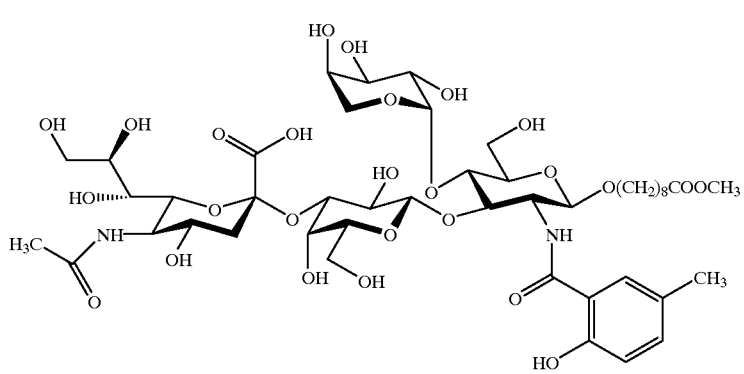

53.92; 56.65; 62.59; 62.79; 64.04; 69.27 (2×C); 69.66; 70.74 (3×C); 72.74; 74.84; 76.68; 77.29; 77.50; 83.83; 101.36; 102.67; 104.59; 128.58 (2×C); 129.61 (2×C); 132.58; 136.23; 166.15; 175.29; 175.48; 175.99.

(c) 18 mg (87%) of compound No. (74) are obtained according to Example B2.1(c) from 18 mg (19 μmol) of compound No. (76) and 18 mg (27 μmol) of GDP-L-galactose. $^1$H-NMR (CD$_3$OD, 400.13 MHz) δ=1.05 (broad m, 8 H); 1.40 (m, 4 H); 1.62 (broad t, 12.4 Hz, 1 H); 1.94 (s, 3 H); 2.16 (t, 8.4 Hz, 2 H); 2.68 (dd, 12.4 Hz, 3.4 Hz, 1 H); 3.29 (broad t, 11.0 Hz, 1 H); 3.37–3.96 (m, 27 H); 4.31(broad t, 15.4 Hz, 1 H); 4.47 (d, 8.6 Hz, 1 H); 4.63 (broad t, 11.0 Hz, 1 H); 4.72 (broad d, 8.6 Hz, 1 H); 5.05 (d, (a) 119 mg (57%) of peracetylated amide are obtained according to Example A8 from 180 mg (236 μmol) of amine No. (57) and 39 mg (256 μmol) of 5-methylsalicylic acid in 3 ml of dry acetonitrile, and the product is deacetylated immediately according to Example B8.1(d): 77 mg (90%) of disaccharide No. (87) are obtained.

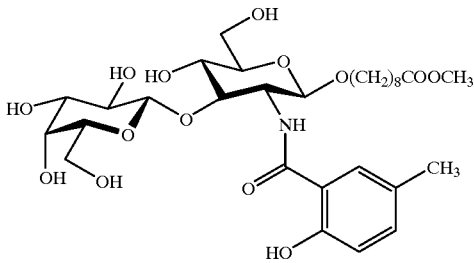

(87)

$^1$H-NMR (CD$_3$OD-CDCl$_3$, 400.13 MHz) δ=0.90–1.21 (m, 8 H); 1.33–1.54 (m, 4 H); 2.19 (t, 7.5 Hz, 2 H); 2.21 (s, 3 H); 3.32–3.99 (m, 17 H); 4.32 (d, 8.6 Hz, 1 H); 4.64 (d, 8.6 Hz, 1 H); 7.78 (d, 7.6 Hz, 1 H); 8.15 (dd, 1.4 Hz, 7.6 Hz, 1 H); 8.60 (d, 1.4 Hz, 1 H). $^{13}$C-NMR (CD$_3$OD-CDCl$_3$, 100.6 MHz) δ=20.68; 25.57; 26.59; 29.65; 29.73; 29.86; 30.12; 34.69; 52.14; 56.01; 62.03; 62.18; 69.59; 70.06; 70.92; 71.80; 73.71; 76.32; 76.62; 83.19; 102.07; 104.37; 116.77; 119.15; 127.54; 128.89; 135.26; 160.61; 171.70; 176.11.

(b) 31 mg (84%) of compound No. (88) are obtained according to Example B1.1(b) (in this case the buffer solution contains 9% of DMSO (vol/vol)) from 25 mg (39 μmol) of compound No. (87) and 35 mg (53 μmol) of CMP-sia.

(t, 7.6 Hz, 2 H); 2.28 (s, 3 H); 2.72 (dd, 11.6 Hz, 2.8 Hz, 1 H); 3.33 (m, 1 H); 3.39–3.74 (m, 17 H); 3.81–4.02 (m, 6 H); 4.41 (d, 8.6 Hz, 1 H); 4.61 (broad d, 8.6 Hz, 1 H); 6.75 (d, 7.6 Hz, 1 H); 7.16 (dd, 1.4 Hz, 7.6 Hz, 1 H); 7.54 (d, 1.4 Hz, 1 H). $^{13}$C-NMR (CD$_3$OD, 100.6 MHz) δ=20.57; 22.46; 25.80; 26.92; 29.87; 30.02; 30.09 (2×C); 30.35; 34.58; 41.37; 51.76; 53.70; 55.95; 62.26; 62.57; 63.73; 68.68; 69.10; 69.37; 70.49; 70.57; 70.65; 72.51; 74.64; 76.52; 77.11; 77.28; 82.48; 101.03; 101.52; 103.92; 116.46; 118.25; 128.64; 129.05; 135.46; 159.08; 171.69; 174.96; 175.26; 175.83.

(c) 14 mg (84%) of compound No. (86) are obtained according to Example B2.1(c) from 14 mg (15 μmol) of compound No. (88) and 16 mg (26 μmol) of GDP-D-arabinose. $^1$H-NMR (CD$_3$OD, 400.13 MHz) δ=0.91–1.20 (m, 8 H); 1.34–1.46 (m, 4 H); 1.62 (broad t, 12.4 Hz, 1 H); 1.96 (s, 3 H); 2.19 (t, 8.4 Hz, 2 H); 2.26 (s, 3 H); 2.75 (broad dd, 12.4 Hz, 3.4 Hz, 1 H); 3.29 (m, 1 H); 3.36–4.00 (m, 27 H); 4.42 (broad t, 7.0 Hz, 1 H); 4.58 (broad d, 8.6 Hz, 1 H); 4.68 (broad d, 8.6 Hz, 1 H); 5.08 (d, 4.3 Hz, 1 H); 6.81 (d, 7.6 Hz, 1 H); 7.17 (dd, 1.4 Hz, 7.6 Hz, 1 H); 7.53 (d, 1.4 Hz, 1 H). $^{13}$C-NMR (CD$_3$OD, 100.6 MHz) δ=20.77; 22.63; 26.00; 27.13; 30.08; 30.20; 30.28; 30.59; 34.79; 41.94; 51.96; 53.93; 57.94; 61.59; 63.03; 63.93; 65.41; 68.67; 69.36; 69.50; 70.37; 70.44; 70.74; 70.92; 71.14; 72.53; 74.87; 74.96; 76.47 (2×C); 77.22; 77.51; 100.39; 101.15; 102.38; 103.21; 117.13; 118.58; 129.03; 129.40; 135.71; 158.84; 171.67; 175.05; 175.45; 176.04.

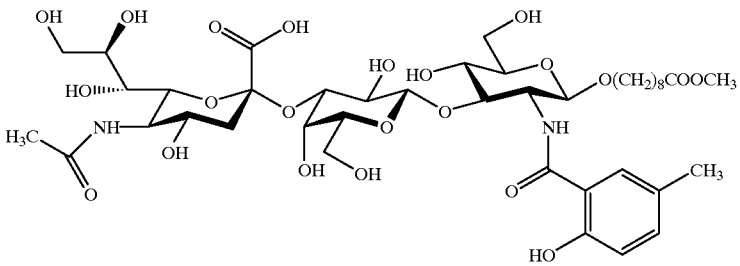

(88)

$^1$H-NMR (CD$_3$OD, 400.13 MHz) δ=0.89–1.21 (m, 8 H); 1.34–1.46 (m, 4 H); 1.65 (t, 11.6 Hz, 1 H); 1.96 (s, 3 H); 2.18

EXAMPLE B8.14

Preparation of Compound No. (90)

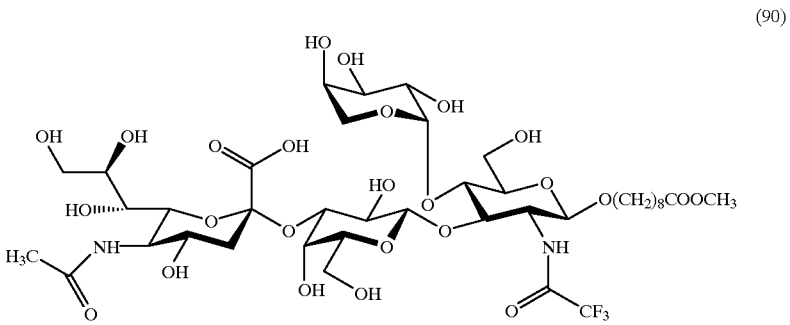
(90)

(a) 150 mg (196 μmol) of amine No. (57) are dissolved in 2 ml of dry methylene chloride at RT, and 70 μl (503 μmol) of trifluoroacetic anhydride and 70 μl of triethylamine are added in succession. After 3 h, the solvent is evaporated off and the residue is chromatographed over silica gel (eluent: hexane/ethyl acetate—1/1). 156 mg (93%) of peracetylated amide are obtained and are deacetylated by means of sodium methanolate—as described in Example 30(a). 110 mg (100%) of disaccharide No. (91) are obtained.

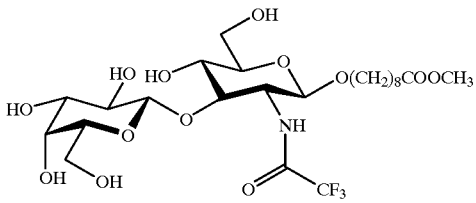
(91)

$^1$H-NMR (CD$_3$OD-CDCl$_3$, 400.13 MHz) δ=1.21–1.38 (m, 8 H); 1.46–1.62 (m, 4 H); 2.30 (t, 7.5 Hz, 2 H); 3.33 (m, 1 H); 3.42–3.92 (m, 16 H); 4.38 (d, 8.6 Hz, 1 H); 4.53 (broad d, 8.6 Hz, 1 H). $^{13}$C-NMR (CD$_3$OD-CDCl$_3$, 100.6 MHz) δ=25.84; 26.78; 29.90; 30.06; 30.09; 30.37; 34.74; 52.09; 56.49; 62.28; 62.38; 69.92; 70.31; 70.77; 72.00; 74.45; 76.89; 77.27; 83.40; 101.62; 105.09; 176.24; no resolution of the remaining signals.

(b) 39 mg (89%) of compound No. (92) are obtained according to Example B1.1(b) (in this case the buffer solution comprises 9% of DMSO (vol/vol)) from 30 mg (49 μmol) of compound No. (91) and 42 mg (64 μmol) of CMP-sia.

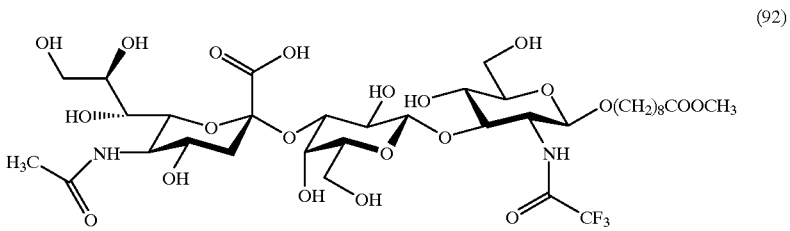
(92)

$^1$H-NMR (CD$_3$OD, 400.13 MHz) δ=1.19–1.32 (m, 8 H); 1.41–1.56 (m, 4 H); 1.71 (t, 11.6 Hz, 1 H); 1.97 (s, 3 H); 2.25 (t, 7.6 Hz, 2 H); 2.74 (dd, 11.6 Hz, 2.8 Hz, 1 H); 3.28 (m, 1 H); 3.35–3.97 (m, 23 H); 4.31 (d, 8.6 Hz, 1 H); 4.45 (broad d, 8.6 Hz, 1 H). $^{13}$C-NMR (CD$_3$OD, 100.6 MHz) δ=22.73; 25.99; 26.96; 30.06; 30.24 (2×C); 30.56; 34.77; 41.43; 51.97; 53.97; 56.37; 63.51; 62.61; 63.81; 69.26; 69.53; 70.48 (2×C); 70.54; 70.72; 72.69; 74.87; 76.71; 77.58 (2×C); 83.45; 101.33; 101.95; 104.82; 117.51 (q); 159.40 (q); 175.32; 175.50; 176.05.

(c) 16 mg (84%) of compound No. (90) are obtained according to Example B2.1(c) from 17 mg (19 μmol) of compound No. (92) and 18 mg (29 μmol) of GDP-D-arabinose. $^1$H-NMR (CD$_3$OD, 400.13 MHz) δ=1.14–1.28 (m, 8 H); 1.40–1.55 (m, 4 H); 1.65 (t, 12.4 Hz, 1 H); 1.95 (s, 3 H); 2.25 (t, 8.4 Hz, 2 H); 2.74 (dd, 12.4 Hz, 3.4 Hz, 1 H); 3.30–3.90 (m, 28 H); 4.10 (t, 7.0 Hz, 1 H); 4.37 (d, 8.6 Hz, 1 H); 4.48 (d, 8.6 Hz, 1 H); 5.01 (d, 4.3 Hz, 1 H). $^{13}$C-NMR (CD$_3$OD, 100.6 MHz) δ=22.77; 25.87; 26.79; 29.87; 30.03; 30.06; 30.37; 32.51; 41.90; 52.35; 53.70; 57.84; 61.18; 62.95; 63.47; 65.27; 68.19; 69.14; 69.40; 69.94; 70.06; 70.59; 70.79; 70.99; 72.34; 73.97; 74.60; 76.37; 76.54; 77.14; 77.45; 100.12; 100.72; 101.70; 103.97; 117.39 (q); 159.41 (q); 175.02; 175.77; 176.85.

EXAMPLE B9.1

Preparation of Compound No. (27)

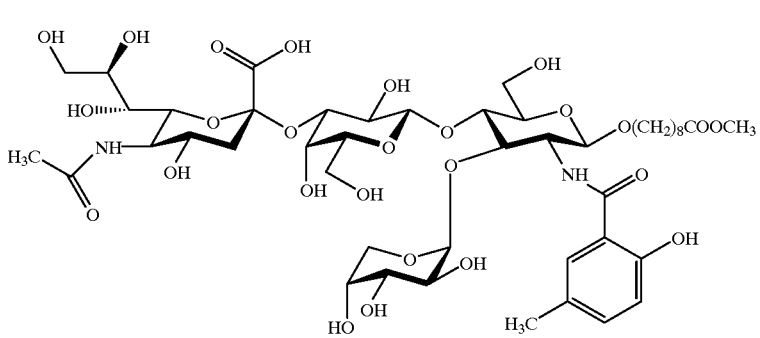
(27)

(a) 19 mg (95%) of compound No. (29) are obtained according to Example B1.1 (a1) (in this case the buffer solution comprises about 11% of DMSO (vol/vol)) from 15 mg (31 μmol) of compound No. (28) and 25 mg (40 μmol) of UDP-gal.

(b) 26 mg (99%) of compound No. (30) are obtained according to Example B1.1(b) (in this case the buffer solution comprises 8% of DMSO (vol/vol)) from 18 mg (28 μmol) of compound No. (29 and 28 mg (43 μmol) of CMP-sia.

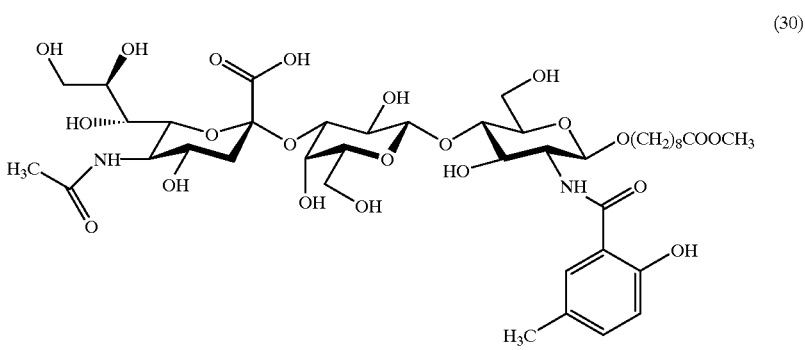
(30)

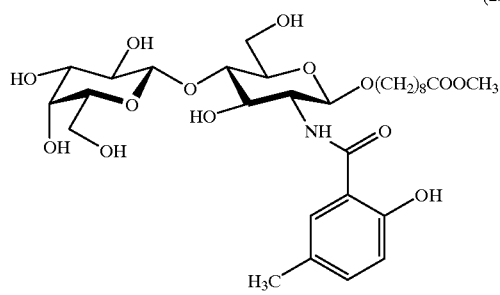
(29)

$^1$H-NMR (CD$_3$OD, 250.13 MHz) δ=1.01 (m, 8 H); 1.39 (m, 4 H); 2.13 (t, 7.5 Hz, 2 H); 2.21 (s, 3 H); 3.32–3.95 (m, 17 H); 4.32 (d, 8.6 Hz, 1 H); 4.50 (d, 8.6 Hz, 1 H); 6.71 (d, 7.6 Hz, 1 H); 7.11 (dd, 1.4 Hz, 7.6 Hz, 1 H); 7.52 (d, 1.4 Hz, 1 H). $^{13}$C-NMR (CD$_3$OD, 62.90 MHz) δ=20.60; 26.00; 27.12; 30.07; 30.28 (2×C); 30.56; 34.77; 51.95; 56.64; 62.00; 62.57; 70.36; 70.75; 72.63; 73.92; 74.83; 76.59; 77.18; 81.15; 102.83; 105.11; 116.37; 118.44; 128.36; 129.05; 135.59; 171.77; 176.03.

$^1$H-NMR (CD$_3$OD, 250.13 MHz) δ=1.02 (m, 8 H); 1.38 (m, 4 H); 1.66 (broad t, 11.6 Hz, 1 H); 1.94 (s, 3 H); 2.14 (t, 7.6 Hz, 2 H); 2.19 (s, 3 H); 2.78 (dd, 11.6 Hz, 2.8 Hz, 1 H); 3.32–4.01 (m, 24 H); 4.41 (d, 8.6 Hz, 1 H); 4.49 (d, 8.6 Hz, 1 H); 6.66 (d, 7.6 Hz, 1 H); 7.06 (dd, 1.4 Hz, 7.6 Hz, 1 H); 7.53 (d, 1.4 Hz, 1 H). $^{13}$C-NMR (CD$_3$OD, 62.90 MHz) δ=20.61; 22.58; 26.01; 27.11; 30.08; 30.26; 30.31; 30.59; 34.79; 42.10; 51.95; 53.93; 56.61; 62.01; 62.79; 64.54; 69.05; 69.34; 70.07; 70.84; 72.97; 74.23; 74.93 (2×C); 76.52; 77.12; 77.63; 81.11; 101.06; 103.09; 104.96; 117.07; 119.46; 127.56; 128.84; 135.34; 162.28; 171.99; 174.91; 175.49; 176.05.

(c) 6 mg (54%) of compound No. (27) are obtained according to Example B3.1(c) from 11 mg (12 μmol) of compound No. (30) and 11 mg (19 μmol) of GDP-D-arabinose. $^1$H-NMR (CD$_3$OD, 250.13 MHz) δ=1.02 (m, 8 H); 1.48 (m, 4 H); 1.62 (broad t, 11.0 Hz, 1 H); 1.93 (s, 3 H); 2.14 (t, 7.6 Hz, 2 H); 2.20 (s, 3 H); 2.79 (dd, 11.6 Hz, 2.8 Hz, 1 H); 3.62–4.17 (m, 28 H); 4.46 (d, 8.6 Hz, 1 H); 4.53 (m, 2 H); 5.06 (d, 4.3 Hz, 1 H); 6.70 (d, 7.6 Hz, 1 H); 7.12 (dd, 1.4 Hz, 7.6 Hz, 1 H); 7.49 (d, 1.4 Hz, 1 H). $^{13}$C-NMR (CD$_3$OD, 62.90 MHz) δ=20.61; 22.57; 26.00;

27.14; 30.07; 30.22; 30.29; 30.58; 34.79; 42.35; 51.95; 53.96; 57.67; 61.38; 62.97; 64.64; 65.12; 68.86; 69.29; 70.14 (3×C); 70.76; 70.97 (2×C); 73.03; 75.02; 75.32; 75.67; 76.84; 77.29; 77.90; 99.89; 100.86; 102.62; 103.77; 116.59; 118.97; 128.48; 129.19; 135.68; 159.56; 171.67; 174.84; 175.51; 176.04.

EXAMPLE B9.2

Preparation of Compound No. (31)

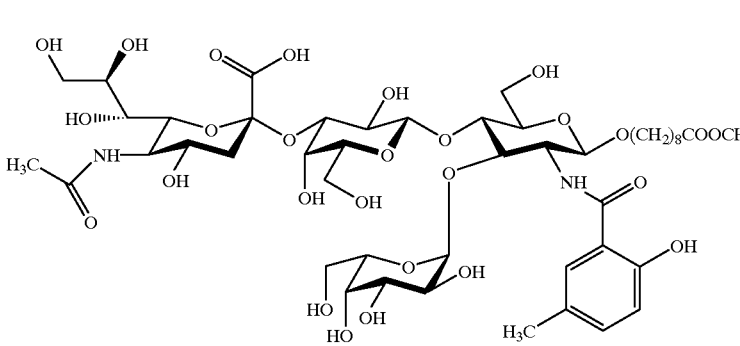

(31)

14 mg (82%) of compound No. (31) are obtained according to Example B3.1(c) from 15 mg (16 μmol) of compound No. (30) and 17 mg (26 μmol) of GDP-L-galactose. $^1$H-NMR (CD$_3$OD, 400.13 MHz) δ=0.50 (m, 2 H); 1.06 (m, 4 H); 1.16 (m, 2 H); 1.42 (m, 4 H); 1.77 (broad t, 11.0 Hz, 1 H); 2.07 (s, 3 H); 2.18 (t, 7.6 Hz, 2 H); 2.24 (s, 3 H); 2.84 (dd, 11.6 Hz, 2.8 Hz, 1 H); 3.37–3.73 (m, 17 H); 3.80–3.85 (m, 8 H); 4.06 (m, 4 H); 4.53 (d, 8.6 Hz, 1 H); 4.57 (broad d, 8.4 Hz, 1 H); 4.70 (t, 6.4 Hz, 1 H); 5.08 (d, 4.3 Hz, 1 H); 6.74 (d, 7.6 Hz, 1 H); 7.16 (dd, 1.4 Hz, 7.6 Hz, 1 H); 7.54 (d, 1.4 Hz, 1 H). $^{13}$C-NMR (CD$_3$OD, 100.60 MHz) δ=20.62; 22.60; 26.00; 27.13; 30.07; 30.20; 30.27; 30.57; 34.79; 42.28; 51.95; 53.98; 57.43; 61.24; 62.41; 62.68; 64.63; 68.14; 69.06; 69.27; 70.12 (2×C); 70.76; 70.92; 70.97; 71.09; 73.05; 75.02; 75.84; 76.39; 76.75; 77.35; 77.68; 100.00; 100.93; 102.53; 104.07; 116.63; 118.51; 128.51; 129.22; 135.69; 159.63; 171.81; 174.84; 175.52 (2×C).

EXAMPLE B10.1

Preparation of Compound No. (32)

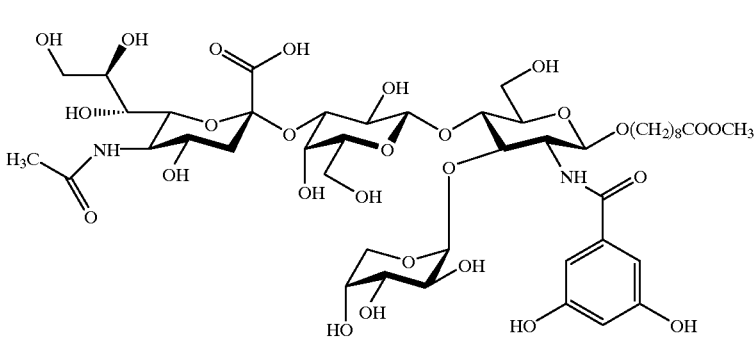

(32)

(a) 27 mg (83%) of compound No. (34) are obtained according to Example B1.1 (a1) (in this case the buffer solution comprises about 8% of DMSO (vol/vol)) from 29 mg (54 μmol) of compound No. (33) and 39 mg (63 μmol) of UDP-gal.

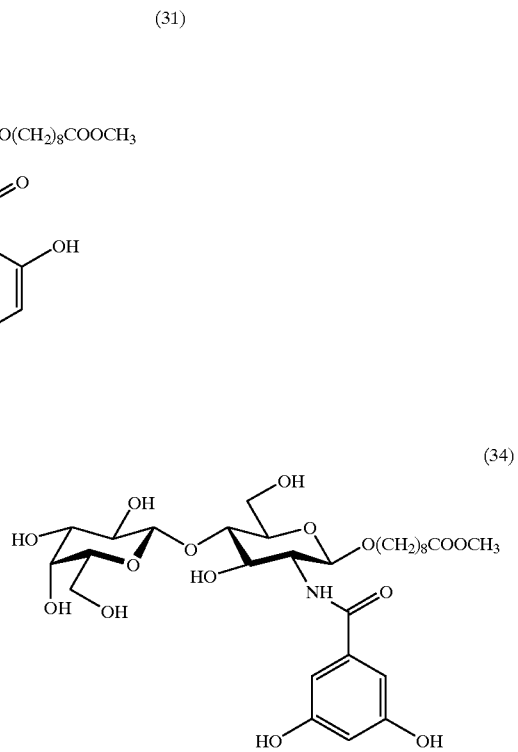

(34)

$^1$H-NMR (CD$_3$OD, 400.13 MHz) δ=1.19 (m, 6 H); 1.22 (m, 2 H); 1.42 (m, 4 H); 2.17 (t, 7.5 Hz, 2 H); 3.33–3.89 (m, 17 H); 4.33 (d, 8.6 Hz, 1 H); 4.49 (d, 9.0 Hz, 1 H); 6.35 (t, about 2.0 Hz, 1 H); 6.66 (d, about 2.0 Hz, 2 H). $^{13}$C-NMR (CD$_3$OD, 100.61 MHz) δ=26.00; 27.16; 30.10; 30.30; 30.35; 30.67; 34.79; 51.96; 57.20; 60.06; 62.54; 70.34; 70.76; 72.63; 73.92; 74.84; 76.56; 77.15; 81.29; 102.83;

105.12; 106.43; 106.90 (2×C); 138.31; 159.73 (2×C); 170.84; 176.21.

(b) 27 mg (68%) of compound No. (35) are obtained according to Example B1.1(b) from 27 mg (42 µmol) of compound No. (34) and 39 mg (59 µmol) of CMP-sia.

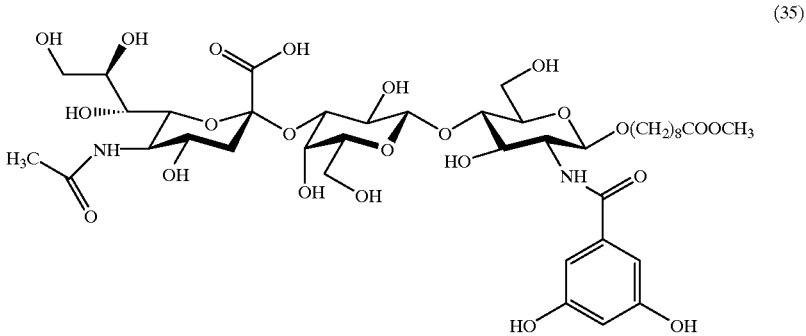

(35)

$^1$H-NMR (CD$_3$OD, 250.13 MHz) δ=1.08 (m, 8 H); 1.48 (m, 4 H); 1.63 (broad t, 11.0 Hz, 1 H); 1.90 (s, 3 H); 2.12 (t, 7.6 Hz, 2 H); 2.73 (dd, 11.0 Hz, 2.8 Hz, 1 H); 3.38–3.88 (m, 23 H); 3.95 (dd, 10.0 Hz, 3.4 Hz, 1 H); 4.35 (d, 8.6 Hz, 1 H); 4.41 (d, 8.6 Hz, 1 H); 6.29 (t, about 2.0 Hz, 1 H); 6.65 (d, about 2.0 Hz, 2 H). $^{13}$C-NMR (CD$_3$OD, 100.61 MHz) δ=22.65; 26.00; 27.15; 30.10; 30.30; 30.36; 30.66; 34.79; 41.58; 51.96; 53.94; 57.00; 62.05; 62.75; 64.42; 69.12; 69.29; 70.01; 70.79; 70.87; 72.96; 73.97; 74.90; 76.51; 77.12; 77.61; 81.37; 101.11; 102.91; 105.00; 106.46; 106.92 (2×C); 138.26; 159.74 (2×C); 170.87; 175.03; 175.50; 176.22.

(c) 11 mg (87%) of compound No. (32) are obtained according to Example B3.1(c) from 11 mg (12 µmol) of compound No. (35) and 12 mg (20 µmol) of GDP-D-arabinose. $^1$H-NMR (CD$_3$OD, 250.13 MHz) δ=1.09 (m, 8 H); 1.41 (m, 4 H); 1.62 (broad t, 11.0 Hz, 1 H); 1.92 (s, 3 H); 2.18 (t, 7.6 Hz, 2 H); 2.79 (dd, 2.8 Hz, 11.0 Hz, 1 H); 3.27–4.06 (m, 28 H); 4.43–4.60 (m, 3 H); 5.08 (d, 5.0 Hz, 1 H); 6.32 (t, about 3.0 Hz, 1 H); 6.65 (d, about 3 Hz, 2 H). $^{13}$C-NMR (CD$_3$OD, 62.90 MHz) δ=22.58; 26.01; 27.20; 30.12; 30.28; 30.38; 30.69; 34.81; 42.81; 51.96; 53.96; 58.23; 61.35; 62.97; 64.64; 65.48; 68.84; 69.29; 70.18 (2×C); 70.78; 70.96 (2×C); 73.03; 75.07; 75.39; 76.27; 76.80; 77.25; 77.80; 99.89; 100.85; 102.52; 103.81; 106.61; 106.94 (2×C); 138.05; 159.85 (2×C); 170.92; 175.51; no resolution of the remaining signals.

EXAMPLE B10.2

Preparation of Compound No. (36)

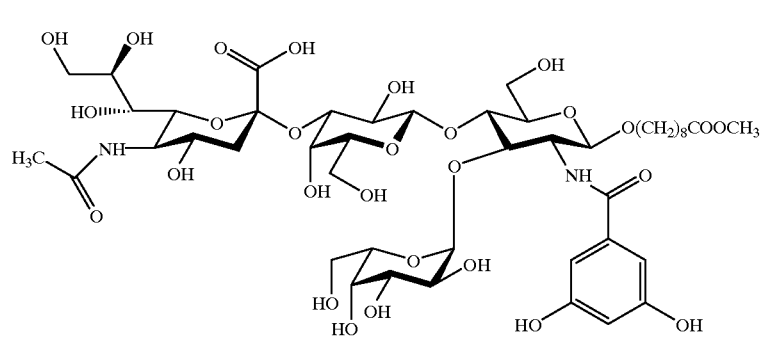

(36)

9 mg (70%) of compound No. (36) are obtained according to Example B3.1(c) from 11 mg (12 µmol) of compound No. (35) and 12 mg (18 µmol) of GDP-L-galactose. $^1$H-NMR (CD$_3$OD, 250.13 MHz) δ=1.09 (m, 8 H); 1.46 (m, 4 H); 1.62 (broad t, 11.0 Hz, 1 H); 1.92 (s, 3 H); 2.18 (t, 7.6 Hz, 2 H); 2.80 (dd, 2.8 Hz, 11.0 Hz, 1 H); 3.30–4.08 (m, 29 H); 4.48 (d, 8.6 Hz, 1 H); 4.50 (broad d, 8.6 Hz, 1 H); 4.65 (t, 6.4 Hz, 1 H); 5.04 (d, 5.0 Hz, 1 H); 6.32 (t, about 3.0 Hz, 1 H); 6.65 (d, about 3 Hz, 2 H). $^{13}$C-NMR (CD$_3$OD, 62.90 MHz) δ=22.58; 26.01; 27.20; 30.12; 30.29; 30.38; 30.69; 34.81; 42.23; 52.15; 53.96; 58.44; 61.21; 62.43; 62.70; 64.66; 69.00; 69.27; 70.15 (2×C); 70.79; 70.92 (2×C); 71.05 (2×C); 73.05; 75.02; 75.87; 76.31; 76.78; 77.31; 77.66; 99.90; 100.90; 102.44; 104.09; 106.62; 106.95 (2×C); 138.04; 159.85 (2×C); 171.03; 174.81; 175.52; 176.23.

EXAMPLE B11

Preparation of Compound No. (37)

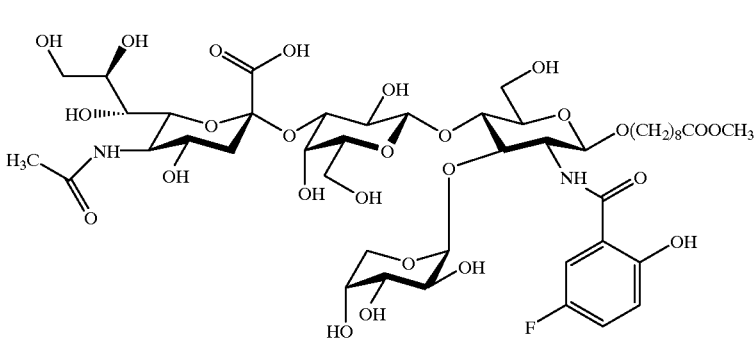

(37)

(a) 13 mg (41%) of compound No. (38) are obtained according to Example B1.1(a1) (in this case the buffer solution comprises about 9% of DMSO (vol/vol)) from 22 mg (46 μmol) of compound No. (37a) and 36 mg (59 μmol) of UDP-gal.

(b) 11 mg (65%) of compound No. (39) are obtained according to Example B1.1(b) (in this case the buffer solution comprises 8% of DMSO (vol/vol)) from 12 mg (18 μmol) of compound No. (38) and 22 mg (33 μmol) of CMP-sia.

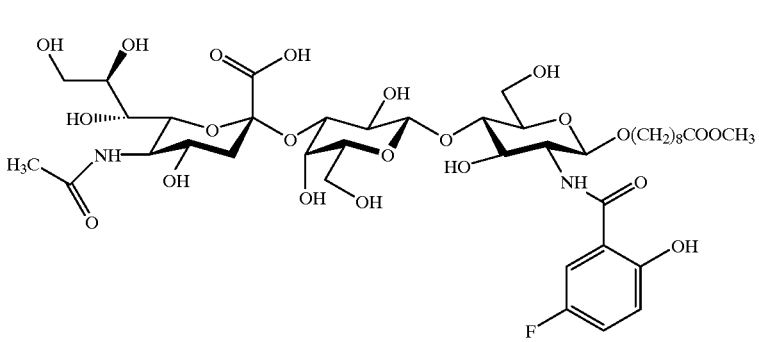

(39)

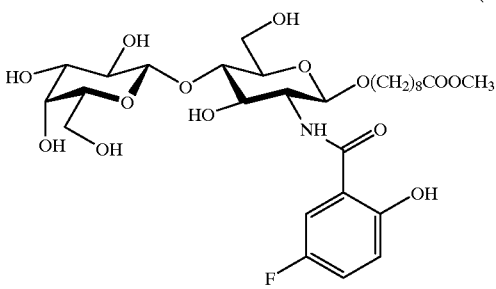

(38)

$^1$H-NMR (CD$_3$OD, 250.13 MHz) δ=1.15 (m, 8 H); 1.51 (m, 4 H); 2.27 (t, 7.5 Hz, 2 H); 3.41–4.02 (m, 17 H); 4.43 (d, 8.6 Hz, 1 H); 4.62 (d, 8.6 Hz, 1 H); 6.92 (dd, 5.5 Hz, 10.3 Hz, 1 H); 7.16 (ddd, 3.4 Hz, 7.6 Hz, 8.3 Hz, 1 H); 7.59 (dd, 5.5 Hz, 10.3 Hz, 1 H). $^{13}$C-NMR (CD$_3$OD, 62.90 MHz) δ=25.45; 26.46; 29.54; 29.67;29.71; 29.98; 34.59; 52.06; 56.19; 61.42; 61.96; 69.59; 70.72; 71.98; 73.05; 74.00; 75.69; 76.35; 80.47; 102.00; 104.23; 113.94 (d, 24.7 Hz); 117.11 (d, 6.5 Hz); 119.38 (d, 7.4 Hz); 121.38 (d, 23.3 Hz); 156.97 (d, 174.2 Hz); 158.63; 170.20; 175.96.

$^1$H-NMR (CD$_3$OD, 400.13 MHz) δ=1.00 (m, 8 H); 1.32 (m, 4 H); 1.62 (broad t, 11.6 Hz, 1H); 1.89 (s, 3 H); 2.09 (t, 7.6 Hz, 2 H); 2.71 (dd, 11.6 Hz, 2.8 Hz, 1 H); 3.29–3.95 (m, 24 H); 4.35 (d, 8.6 Hz, 1 H); 4.42 (d, 8.6 Hz, 1 H); 6.76 (dd, 5.5 Hz, 10.3 Hz, 1 H); 7.03 (ddd, 3.4 Hz, 7.6 Hz, 8.3 Hz, 1 H); 7.45 (dd, 5.5 Hz, 10.3 hz, 1 H). $^{13}$C-NMR (CD$_3$OD, 62.90 MHz) δ=22.63; 26.00, 27.13; 30.07; 30.31 (2×C); 30.55; 34.77; 42.15; 51.96; 53.98; 56.68; 62.35; 62.77;, 64.36; 69.28 (2×C); 70.01; 70.76; 70.88; 72.98; 73.93; 74.93; 76.57; 76.98; 77.64; 81.23; 101.21; 102.81; 104.99; 113.96 (d, 24.7 Hz); 119.87 (d, 7.4 Hz); 121.56 (d, 23.3 Hz); 156.55 (d, 174.2 Hz); 175.18; 175.51; no resolution of the remaining signals.

(c) 8 mg (46%) of compound No. (37) are obtained according to Example B3.1(c) from 15 mg (16 μmol) of compound No. (39) and 16 mg (26 μmol) of GDP-D-arabinose. $^1$H-NMR (CD$_3$OD, 400.13 MHz) δ=1.07 (m, 8 H); 1.43 (m, 4 H); 1.67 (broad t, 11.0 Hz, 1 H); 1.96 (s, 3 H); 2.18 (t,7.6Hz, 2 H); 2.83 (dd, 11.6 Hz, 2.8 Hz, 1 H); 3.32–4.16 (m, 28 H); 4.51 (d, 8.6 Hz, 1 H); 4.55 (t, 6.4 Hz, 1 H); 4.59 (d, 8.6 Hz, 1 H); 5.08 (d, 4.3 Hz, 1 H); 6.85 (dd, 5.5 Hz, 10.3 Hz, 1 H); 7.13 (ddd, 3.4 Hz, 7.6 Hz, 8.3 Hz, 1 H); 7.49 (dd, 5.5 Hz, 10.3 Hz, 1 H). $^{13}$C-NMR (CD$_3$OD, 100.60 MHz) δ=22.57; 26.99; 27.13; 30.05; 30.25 (2×C); 30.57; 34.78; 42.37; 51.95; 53.97; 57.45; 61.37; 62.99; 64.67; 65.15; 68.87; 69.30; 70.15 (3×C); 70.76; 70.92; 70.97; 73.03; 75.01; 75.33; 75.75; 76.84; 77.33; 77.89; 99.96; 100.79; 100.86; 102.55; 103.80; 114.45 (d, 24.4 Hz); 117.62 (d, 7.4 Hz); 119.92 (d, 7.5 Hz); 121.75 (d, 23.7 Hz); 157.82 (d, 174.2 Hz); 170.33; 174.81; 175.52; 177.06; no resolution of the remaining signals.

EXAMPLE B12

Preparation of Compound No. (40)

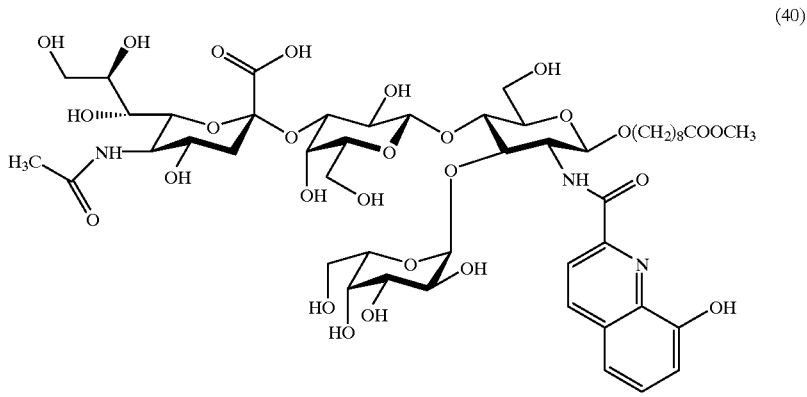

(40)

(a) 31 mg (90%) of compound No. (42) are obtained according to Example B1.1(a1) (in this case the buffer solution comprises about 18% of DMSO (vol/vol)) from 26 mg (50 μmol) of compound No. (41) and 35 mg (57 μmol) of UDP-gal.

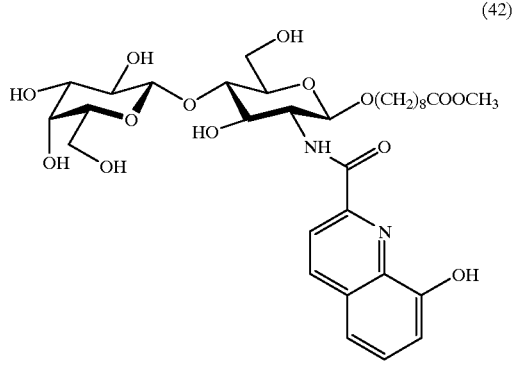

(42)

$^1$H-NMR (CD$_3$OD, 250.13 MHz) δ=0.40–1.41 (m, 12 H); 1.92 (t, 7.5 Hz, 2 H); 3.32–4.01 (m, 17 H); 4.35 (d, 8.6 Hz, 1 H); 4.49 (d, 8.6 Hz, 1 H); 7.08 (dd, 0.9 Hz, 7.6 Hz, 1 H); 7.33 (dd, 0.9 Hz, 7.6 Hz, 1 H); 7.45 (t, 7.6 Hz, 1 H); 8.11 (d, 8.3 Hz, 1 H); 8.33 (d, 8.3 Hz, 1 H). $^{13}$C-NMR (CD$_3$OD, 62.90 MHz) δ=25.78; 27.09; 29.92; 30.18; 30.25; 30.50; 34.65; 51.92; 57.15; 62.04; 62.53; 70.32; 70.65; 72.63; 74.06; 74.83; 76.69; 77.15; 81.24; 102.92; 105.15; 112.77; 118.98; 120.13; 130.58; 131.47; 138.45; 138.83; 148.87; 155.06; 167.87; 175.89.

(b) 23 mg (80%) of compound No. (43) are obtained according to Example B2.1(c) (in this case the buffer solution comprises about 12% of DMSO (vol/vol)) from 20 mg (29 μmol) of compound No. (42) and 29 mg (44 μmol) of CMP-sia.

(43)

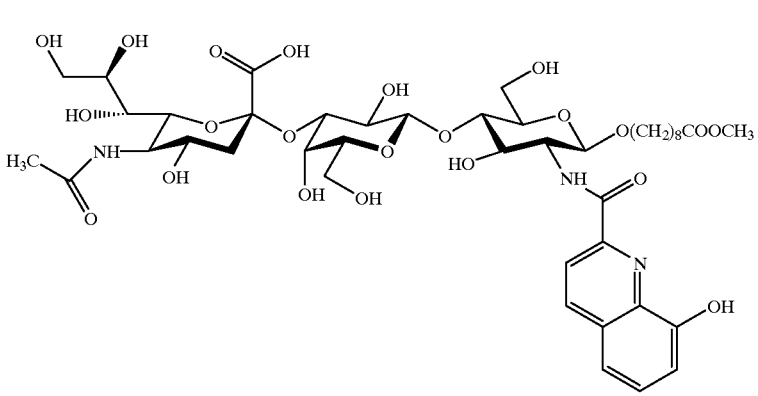

¹H-NMR (CD₃OD, 250.13 MHz) δ=0.41–1.41 (m, 12 H); 1.66 (broad t, 11.6 Hz, 1 H); 1.95 (m, 5 H); 2.78 (dd, 11.6 Hz, 2.8 Hz, 1 H); 3.35–4.05 (m, 24 H); 4.42 (d, 8.6 Hz, 1 H); 4.56 (d, 8.6 Hz, 1 H); 7.08 (dd, 0.9 Hz, 7.6 Hz, 1 H); 7.32 (dd, 0.9 Hz, 7.6 Hz, 1 H); 7.45 (t, 7.6 Hz, 1 H); 8.12 (d, 8.3 Hz, 1 H); 8.33 (d, 8.3 Hz, 1 H). ¹³C-NMR (CD₃OD, 62.90 MHz) δ=22.62; 25.78; 27.10; 29.74; 30.19; 30.25; 30.50; 34.66; 42.19; 51.92; 53.95; 57.07; 62.11; 62.74; 64.49; 69.07; 69.32; 70.04; 70.67; 70.91; 72.96; 74.10; 74.93; 76.68; 77.08; 77.66; 81.44; 101.12; 102.97; 105.08; 112.89; 118.98; 120.05; 131.23; 131.54; 138.45; 138.88; 148.87; 155.06; 167.57; 175.01; 175.51; 175.90.

(c) 5.0 mg (24%) of compound No. (40) are obtained according to Example B1.1(c) from 18.0 mg (18 μmol) of compound No. (43) and 17.2 mg (26 μmol) of GDP-L-galactose. ¹H-NMR (CD₃OD, 400.13 MHz) δ=0.48–1.55 (m, 12 H); 1.64 (broad t, 11.0 Hz, 1 H); 1.95 (s, 3 H); 1.97 (t, 7.6 Hz, 2 H); 2.79 (dd, 11.6 Hz, 2.8 Hz, 1 H); 3.32–4.14 (m, 27 H); 4.50 (d, 8.6 Hz, 1 H); 4.60 (m, 1 H); 4.68 (broad d, 8.6 Hz, 1 H); 5.13 (d, 4.3 Hz, 1 H); 6.96 (dd, 0.9 Hz, 7.6 Hz, 1 H); 7.11 (dd, 0.9 Hz, 7.6 Hz, 1 H); 7.36 (t, 7.6 Hz, 1 H); 8.00 (d, 8.3 Hz, 1 H); 8.20 (d, 8.3 Hz, 1 H). ¹³C-NMR (CD₃OD, 100.6 MHz) δ=22.56; 25.81; 27.10; 29.94; 30.19; 30.23; 30.54; 34.70; 42.34; 53.96; 61.23; 62.44; 62.73; 64.70; 69.00; 69.33; 70.05; 70.16; 70.73; 70.95 (3×C); 71.05 (2×C); 73.06; 75.02; 75.79; 76.82; 77.45; 77.68; 99.96; 100.93; 102.86; 104.10; 113.81; 119.73; 132.08; 138.49; no resolution of the remaining signals.

EXAMPLE B13

Preparation of Compound No. (44)

(44)

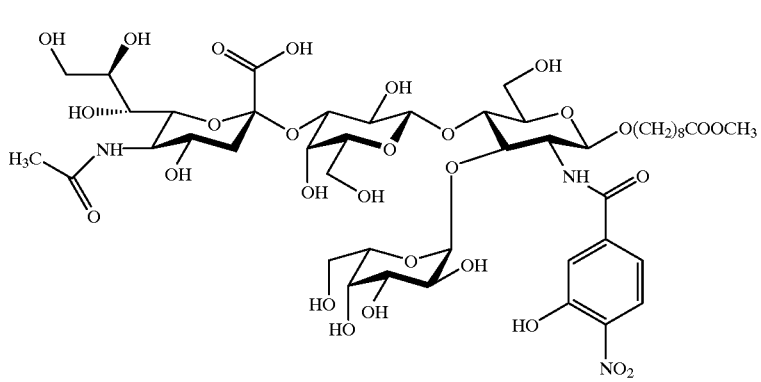

(a) 66 mg (89%) of compound No. (46) are obtained according to Example B1.1(a1) (in this case the buffer solution comprises about 7% of DMSO (vol/vol)) from 57 mg (111 μmol) of compound No. (45) and 92 mg (144 μmol) of UDP-gal.

(46)

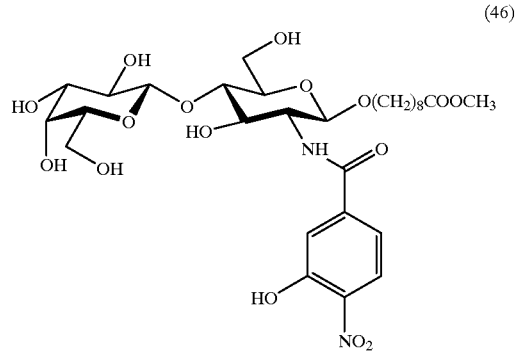

¹H-NMR (CD₃OD, 250.13 MHz) δ=1.02 (m, 8 H); 1.37 (m, 4 H); 2.11 (t, 7.5 Hz, 2 H); 3.31–3.92 (m, 17 H); 4.36

(d, 8.6 Hz, 1 H); 4.50 (d, 8.6 Hz, 1 H); 7.30 (dd, 2.1 Hz, 8.3 Hz, 1 H); 7.47 (d, 2.1 Hz, 1 H); 8.02 (d, 8.3 Hz, 1 H). $^{13}$C-NMR (CD$_3$OD, 62.90 MHz) δ=25.71; 26.84; 29.78; 30.00 (2×C); 30.28; 34.68; 52.29; 57.37; 61.14; 62.38; 70.20; 71.09; 72.45; 73.38; 74.58; 76.44; 77.12; 80.55; 102.60; 104.79; 119.30; 120.77; 137.92; 143.49; 153.28; 168.75; 176.72.

(b) 11 mg (27%) of compound No. (47) are obtained according to Example B1.1(b) (in this case the buffer solution comprises 9% of DMSO (vol/vol)) from 28 mg (42 μmol) of compound No. (46) and 40 mg (60 μmol) of CMP-sia.

(47)

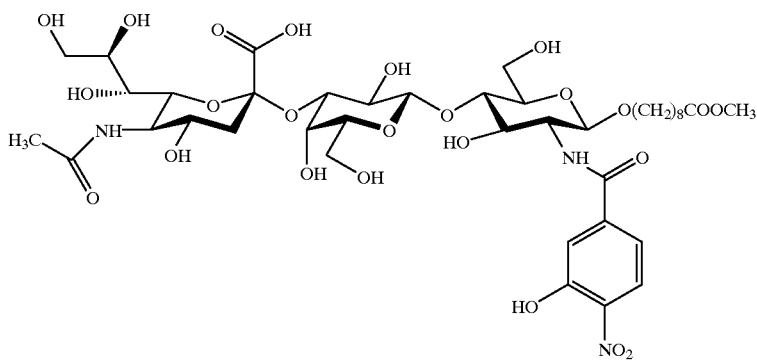

$^1$H-NMR (CD$_3$OD, 250.13 MHz) δ=1.08 (m, 8 H); 1.39 (m, 4 H); 1.65 (broad t, 11.6 Hz, 1 H); 1.93 (s, 3 H); 2.13 (t, 7.6 Hz, 2 H); 2.78 (dd, 11.6 Hz, 2.8 Hz, 1 H); 3.32–4.02 (m, 24 H); 4.40 (d, 8.6 Hz, 1 H); 4.46 (d, 8.6 Hz, 1 H); 7.21 (dd, 2.1 Hz, 8.3 Hz, 1 H); 7.42 (d, 2.1 Hz, 1 H); 8.00 (d, 8.3 Hz, 1 H). $^{13}$C-NMR (CD$_3$OD, 62.90 MHz) δ=22.60; 25.99; 27.17; 30.07; 30.30; 30.38; 30.62; 34.71; 42.33; 51.97; 53.94; 57.23; 62.02; 62.77; 64.49; 69.05; 69.33; 70.04; 70.70; 70.89; 72.95; 73.93; 74.94; 76.59; 77.11; 77.65; 81.29; 101.51; 102.79; 105.00; 118.27; 121.53; 126.66; 143.20; 168.55; 174.73; 175.63; 175.99; no resolution of the remaining signals.

(c) 6 mg (77%) of compound No. (44) are obtained according to Example A3(b2) from 7 mg (7 μmol) of compound No. (47) and 8 mg (12 μmol) of GDP-L-gal. $^1$H-NMR (CD$_3$OD, 400.13 MHz) δ=1.15 (m, 8 H); 1.43 (m, 4 H); 1.65 (broad t, 11.0 Hz, 1 H); 1.96 (s, 3 H); 2.17 (t, 7.6 Hz, 2 H); 2.84 (dd, 11.6 Hz, 2.8 Hz, 1 H); 3.25–4.11 (m, 27 H); 4.51 (d, 8.6 Hz, 1 H); 4.54 (broad d, 8.6 Hz, 1 H); 4.66 (t, 6.4 Hz, 1 H); 5.04 (d, 4.3 Hz, 1 H); 6.99 (dd, 2.1 Hz, 8.3 Hz, 1 H); 7.31 (d, 2.1 Hz, 1 H); 7.91 (d, 8.3 Hz, 1 H). $^{13}$C-NMR (CD$_3$OD, 100.60 MHz) δ=22.57; 25.99; 27.17; 30.07; 30.31 (2×C); 30.66; 34.76; 42.36; 51.95; 53.97; 58.18; 61.20; 62.37; 62.72; 64.70; 67.70; 69.01; 69.31; 70.10; 70.77; 70.91; 71.00; 71.13; 73.06; 75.02; 75.89; 76.64; 76.80; 77.37; 77.67; 100.22; 100.91; 102.39; 104.11; 115.07; 123.11; 126.95; 139.41; 142.31; 169.62; 170.32; 174.74; 175.51; 176.06.

C LIGAND BINDING ASSAY FOR DETERMINATION OF IC$_{50}$ VALUES— CONSERVED USE OF POSITIVE CONTROLS

E-selectin/human IgG chimera [cloned and expressed according to Kolbinger, F., Patton, J. T., Geisenhoff, G., Aenis, A., Li, X., Katopodis, A., Biochemistry 35:6385–6392 (1996)] are incubated in Falcon probind™ microtiter plate (Plate 1) at a concentration of 200 ng/well in 0.01 M Tris, 0.15 M NaCl, 1 mM CaCl$_2$, pH 7.4 (Tris-Ca$^{++}$ buffer). Thus the plating solution is dispensed as 100 μl/well of 2 μg/ml E-chimera. Row 12 is left blank with only buffer. Plate 1 is incubated covered at 37° C. for 2 hours. After incubation 100 μl/well of 2% BSA in Tris-Ca$^{++}$ buffer is added and incubated at RT for 1 hour. During incubation the compounds (2×serial dilution) are titrated in 1% BSA in Tris-Ca$^{++}$ using U-shaped low bind microtiter plates (Plate 2). The rows are serially diluted up to row 9. Rows 10, 11, and 12 are just buffer. Final volume is 60 μl/well and the first well contains 10 mM of compound with the exception of the positive controls, A (SLe$^x$-Lemieux) and B are used as positive controls for each plate and the first well contains 5 mM of these compounds. PolySLe$^a$SA-HRP conjugate is prepared in advance by incubating Sialyl Le$^a$-PAA-biotin (cat #01-044, GlycoTech Corp., Rockville, Md.) with Streptavidin-HRP in a molar ratio of 1:2. 60 μl/well of 1 ng/μl of polySLe$^a$SA-HRP conjugate in 1% BSA in Tris-Ca$^{++}$ are added to all wells except row 11 in Plate 2. Plate 1 is washed four times with Tris-Ca$^{++}$ in the automatic plate washer. 100 μl/well are transferred from Plate 2 to Plate 1 starting from lowest concentration of compound. Plate 2 is discarded. The plate is incubated while rocking at RT for 2 hours. The plate is washed 4 times with Tris-Ca$^{++}$ using automatic plate washer. 100 μl/well of Substrate [Mix 3,3', 5,5'-tetramethylbenzidine reagent and H$_2$O$_2$, at 1:1 ratio] are added with an 8 channel pipettor from right to left. The plate is incubated at RT for 2 minutes. The reaction is stopped by adding 100 μl/well of 1M H$_3$PO$_4$ using the 8 channel pipettor from right to left. Absorbance of light at 450 nm is measured in a microtiter plate reader.

Control compound A:

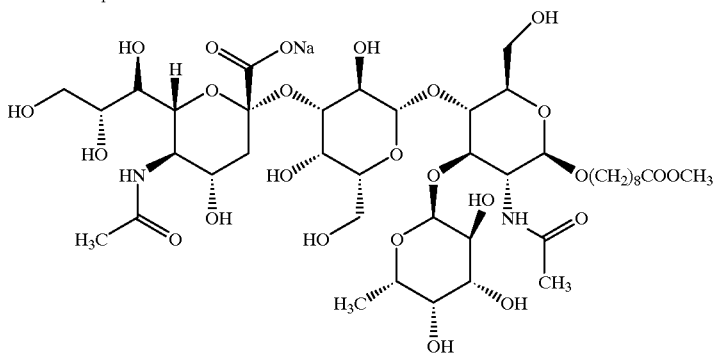

Control compound B:

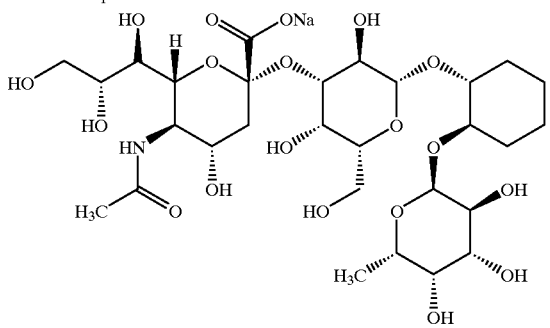

$IC_{50}$ is calculated by determining the concentration of compound required to inhibit maximal binding of the poly-SialylLe$^a$HRP conjugate to immobilized E-selectin/human IgG chimera by 50%. The relative $IC_{50}$ is calculated by determining the ratio of the $IC_{50}$ of an internal control compound to the $IC_{50}$ of the test compound.

In the following table $RIC_{50}$ means $$\frac{IC_{50}(\text{Test compound})}{IC_{50}(\text{Control compound } A)}$$

TABLE 1

| Compound No. | RIC$_{50}$ | Compound No. | RIC$_{50}$ |
|---|---|---|---|
| (1) | 2.780 | (32) | 5.602 |
| (8) | 0.770 | (36) | 1.749 |
| (10) | 0.570 | (37) | 1.264 |
| (14) | 0.720 | (40) | 0.58 |
| (21) | 0.085 | (44) | 0.246 |
| (22) | 1.137 | (48) | 0.376 |
| (26) | 0.366 | (64) | 1.066 |
| (27) | 0.711 | (77) | 0.581 |
| (31) | 0.116 | | |

What is claimed is:

1. A compound of the formula I or II

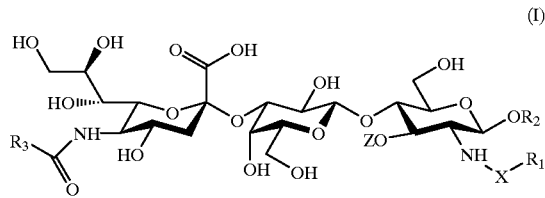

(I)

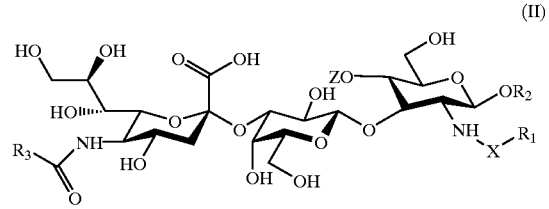

(II)

in which Z is an α-bonded pyranose of the formula III

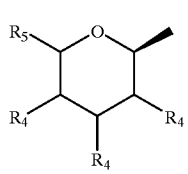

(III)

with the proviso that Z is not L-fucose, $R_1$ is hydrogen, $C_1$–$C_{20}$alkyl, $C_1$–$C_{20}$alkenyl, $C_3$–$C_{15}$cycloalkyl or a mono- or bicyclic $C_6$–$C_{10}$aryl or $C_2$–$C_9$heteroaryl, where alkyl, alkenyl, cycloalkyl, aryl and heteroaryl are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide;

$R_2$ is $C_1$–$C_{18}$alkyl, mono- or polysubstituted $C_1$–$C_{18}$alkyl, $C_3$–$C_8$cycloalkyl or mono- or polysustituted $C_3$–$C_8$cycloalkyl, where one or more $CH_2$ groups in the alkyl and in the cycloalkyl, independently of one another may be replaced by oxygen, sulfur or an imino group and the substituents are chosen from the group consisting of OH, SH, $NH_2$, carboxamide, C(O)O and $C_1$–$C_{18}$alkoxycarbonyl;

$R_3$ is a methyl or hydroxymethyl group.

2. A compound according to claim 1, in which $R_1$ is hydrogen, $C_1$–$C_{20}$alkyl or $C_1$–$C_{20}$alkenyl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide.

3. A compound according to claim 2, in which $R_1$ is $C_1$–$C_{10}$alkyl or $C_1$–$C_{10}$alkenyl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide.

4. A compound according to claim 3, in which $R_1$ is $C_1$–$C_5$alkyl or $C_1$–$C_5$alkenyl, which are unsubstituted or substituted by OH or halogen.

5. A compound according to claim 4, in which $R_1$ is —$CH_3$, —$CF_3$, —$CH_2$—$CH$=$CH_2$, —$CH_2OH$ or —$CH_2SH$.

6. A compound according to claim 1, in which $R_1$ is a mono- or bicyclic $C_6$–$C_{10}$aryl or $C_2$–$C_9$heteroaryl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide.

7. A compound according to claim 6, in which $R_1$ is a mono- or bicyclic $C_6$–$C_{10}$aryl or $C_2$–$C_9$heteroaryl, which are substituted by at least one OH and are not further substituted or are further mono- or polysubstituted by a substituent chosen from the group consisting of halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide.

8. A compound according to claim 7, in which $R_1$ is phenyl or a mono- or bicyclic $C_4$–$C_9$heteroaryl, which are substituted by at least one OH and are not further substituted or are further substituted by a substituent chosen from the group consisting of halogen, nitro, $C_1$–$C_{18}$alkyl and $C_1$–$C_{18}$alkoxy.

9. A compound according to claim 8, in which $R_1$ is phenyl, which is substituted by one OH and F, $NO_2$, $CH_3$ or $OCH_3$ or by two OH; or in which $R_1$ is a $C_4$heteroaryl which is substituted by two OH, or a $C_9$heteroaryl which is substituted by one OH.

10. A compound according to claim 1, in which $R_2$ is $C_1$–$C_{18}$alkyl, mono- or polysubstituted $C_1$–$C_{18}$alkyl, $C_3$–$C_8$cycloalkyl or mono- or polysubstituted $C_3$–$C_8$cycloalkyl, where the substituents are chosen from the group consisting of OH, SH, $NH_2$, carboxamide, C(O)O and $C_1$–$C_{18}$alkoxycarbonyl.

11. A compound according to claim 10, in which $R_2$ is $C_1$–$C_{18}$alkyl or $C_1$–$C_{18}$alkyl which is mono- or polysubstituted independently of one another by OH, SH, $NH_2$, carboxamide, C(O)O or $C_1$–$C_{18}$alkoxycarbonyl.

12. A compound according to claim 11, in which $R_2$ is $C_1$–$C_{18}$alkyl or $C_1$–$C_{18}$alkyl which is monosubstituted by C(O)O.

13. A compound according to claim 12, in which $R_2$ is —$(CH_2)_8COOCH_3$.

14. A compound according to claim 1, in which $R_3$ is methyl.

15. A compound according to claim 1, in which the individual $R_4$ independently of one another are hydrogen, OH, $C_1$–$C_4$alkyl, O-$C_1$–$C_4$alkyl, halogen, $NH_2$ or NHC(O)-$C_1$–$C_8$alkyl.

16. A compound according to claim 15, in which the individual $R_4$ independently of one another are OH, halogen or $NH_2$.

17. A compound according to claim 16, in which all the $R_4$ are OH or two $R_4$ are OH and one $R_4$ is halogen or $NH_2$.

18. A compound according to claim 1, in which $R_5$ is hydrogen, $C_1$–$C_8$alkyl or $(CH_2)_mOH$, in which m is a number from 1 to 5.

19. A compound according to claim 18, in which $R_5$ is H, $C_1$–$C_4$alkyl or $(CH_2)_mOH$, in which m is 1 or 2.

20. A compound according to claim 19, in which $R_5$ is hydrogen, $CH_3$ or $CH_2OH$.

21. A compound according to claim 1, in which X is —C(O)—, —S(O)$_2$— or —C(O)Y—, in which Y is —NH—, —S-$C_1$–$C_6$alkylene or —O-$C_1$–$C_6$alkylene.

22. A compound according to claim 21, in which X is —C(O)—, —S(O)$_2$—, —C(O)SCH$_2$ or —C(O)OCH$_2$.

23. A compound according to claim 1, in which $R_1$ is hydrogen, $C_1$–$C_{20}$alkyl or $C_1$–$C_{20}$alkenyl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide; $R_2$ is $C_1$–$C_{18}$alkyl, mono- or polysubstituted $C_1$–$C_{18}$alkyl, $C_3$–$C_8$cycloalkyl or mono- or polysubstituted $C_3$–$C_8$cycloalkyl, where the substituents are chosen from the group consisting of OH, SH, $NH_2$, carboxamide, C(O)O and $C_1$–$C_{18}$alkoxycarbonyl; $R_3$ is methyl; the individual $R_4$ independently of one another are hydrogen, OH, $C_1$–$C_4$alkyl, O-$C_1$–$C_4$alkyl, halogen, $NH_2$ or NHC(O)-$C_1$–$C_8$alkyl; $R_5$ is hydrogen, $C_1$–$C_8$alkyl or $(CH_2)_m$ OH, in which m is a number from 1 to 5; and X is —C(O)—, —S(O)$_2$— or —C(O)Y—, in which Y is —NH—, —S-$C_1$–$C_6$alkylene or —O-$C_1$–$C_6$alkylene.

24. A compound according to claim 23, in which $R_1$ is $C_1$–$C_{10}$alkyl or $C_1$–$C_{10}$alkenyl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono- $C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide; $R_2$ is $C_1$–$C_{18}$alkyl or $C_1$–$C_{18}$alkyl which is mono- or polysubstituted independently of one another by OH, SH, $NH_2$, carboxamide, C(O)O or $C_1$–$C_{18}$alkoxycarbonyl; $R_3$ is methyl; the individual $R_4$ independently of one another are OH, halogen or $NH_2$; $R_5$ is H, $C_1$–$C_4$alkyl or $(CH_2)_m$OH, in which m is 1 or 2; and X is —C(O)—, —S(O)$_2$—, —C(O)SCH$_2$ or —C(O)OCH$_2$.

25. A compound according to claim 24, in which $R_1$ is $C_1$–$C_5$alkyl or $C_1$–$C_5$alkenyl, which are unsubstituted or substituted by OH or halogen; $R_2$ is $C_1$–$C_{18}$alkyl or $C_1$–$C_{18}$alkyl which is monosubstituted by C(O)O; all the $R_4$ are OH or two $R_4$ are OH and one $R_4$ is halogen or $NH_2$; and $R_5$ is hydrogen, $CH_3$ or $CH_2$OH.

26. A compound according to claim 25, in which $R_1$ is —$CH_3$, —$CF_3$, —$CH_2$—CH═$CH_2$, or —$CH_2$OH; $R_2$ is —$(CH_2)_8$COOCH$_3$; all the $R_4$ are OH or two $R_4$ are OH and one $R_4$ is F or $NH_2$; and $R_5$ is hydrogen, $CH_3$ or $CH_2$OH.

27. A compound according to claim 1, in which $R_1$ is a mono- or bicyclic $C_6$–$C_{10}$aryl or $C_2$–$C_9$heteroaryl, which are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide; $R_2$ is $C_1$–$C_{18}$alkyl, mono- or polysubstituted $C_1$–$C_{18}$alkyl, $C_3$–$C_8$cycloalkyl or mono- or polysubstituted $C_3$–$C_8$cycloalkyl, where the substituents are chosen from the group consisting of OH, SH, $NH_2$, carboxamide, C(O)O and $C_1$–$C_{18}$alkoxycarbonyl; $R_3$ is methyl; the individual $R_4$ independently of one another are hydrogen, OH, $C_1$–$C_4$alkyl, O-$C_1$–$C_4$alkyl, halogen, $NH_2$ or NHC(O)-$C_1$–$C_8$alkyl; $R_5$ is hydrogen, $C_1$–$C_8$alkyl or $(CH_2)_m$ OH, in which m is a number from 1 to 5; and X is —C(O)—, —S(O)$_2$— or —C(O)Y—, in which Y is —NH—, —S-$C_1$–$C_6$alkylene or —O-$C_1$–$C_6$alkylene.

28. A compound according to claim 27, in which $R_1$ is a mono- or bicyclic $C_6$–$C_{18}$aryl or $C_2$–$C_9$heteroaryl, which are substituted by at least one OH and are not further substituted or are further mono- or polysubstituted by a substituent chosen from the group consisting of halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, sulfhydryl, thio-$C_1$–$C_{18}$alkyl and $C_1$–$C_{18}$alkylcarboxamide; $R_2$ is $C_1$–$C_{18}$alkyl or $C_1$–$C_{18}$alkyl which is mono- or polysubstituted independently of one another by OH, SH, $NH_2$, carboxamide, C(O)O or $C_1$–$C_{18}$alkoxycarbonyl; $R_3$ is methyl; the individual $R_4$ independently of one another are OH, halogen or $NH_2$; $R_5$ is H, $C_1$–$C_4$alkyl or $(CH_2)_m$OH, in which m is 1 or 2; and X is —C(O)—, —S(O)$_2$—, —C(O)SCH$_2$ or —C(O)OCH$_2$.

29. A compound according to claim 28, in which $R_1$ is phenyl or a mono- or bicyclic $C_4$–$C_9$heteroaryl, which are substituted by at least one OH and are not further substituted or are further substituted by a substituent chosen from the group consisting of halogen, nitro, $C_1$–$C_{18}$alkyl and $C_1$–$C_{18}$alkoxy; $R_2$ is $C_1$–$C_{18}$alkyl or $C_1$–$C_{18}$alkyl which is monosubstituted by C(O)O; all the $R_4$ are OH or two $R_4$ are OH and one $R_4$ is halogen or $NH_2$; and $R_5$ is hydrogen, $CH_3$ or $CH_2$OH.

30. A compound according to claim 29, in which $R_1$ is phenyl, which is substituted by one OH and F, $NO_2$, $CH_3$ or $OCH_3$ or by two OH; or in which $R_1$ is a $C_4$heteroaryl which is substituted by two OH, or a $C_9$heteroaryl which is substituted by one OH; $R_2$ is —$(CH_2)_8$COOCH$_3$; all the $R_4$ are OH or two $R_4$ are OH and one $R_4$ is F or $NH_2$; and $R_5$ is hydrogen, $CH_3$ or $CH_2$OH.

31. A compound of the formula I according to claim 1, in which $R_2$ is —$(CH_2)_8$COOCH$_3$; $R_3$ is methyl; and (a) $R_1$ is hydrogen; Z is an α-bonded L-galactose; and X is —C(O)—; (b) $R_1$ is —$CH_2$—CH═$CH_2$; Z is an α-bonded L-galactose; and X is —C(O)OCH$_2$—; (c) $R_1$ is —$CH_2$—CH═$CH_2$; Z is an α-bonded D-arabinose; and X is —C(O)OCH$_2$—; (d) $R_1$ is 4-hydroxy-3-methoxy-phenyl; Z is an α-bonded D-arabinose; and X is —C(O)—; (e) $R_1$ is 4-hydroxy-3-methoxy-phenyl; Z is an α-bonded L-galactose, and X is —C(O)—; (f) $R_1$ is 2-hydroxy-5-methyl-phenyl; Z is an α-bonded D-arabinose; and X is —C(O)—; (g) $R_1$ is 2-hydroxy-5-methyl-phenyl; Z is an α-bonded L-galactose; and X is —C(O)—; (h) $R_1$ is 2-hydroxy-3-nitro-phenyl; Z is an α-bonded L-galactose; and X is —C(O)—; (i) $R_1$ is 2-hydroxy-5-fluoro-phenyl; Z is an α-bonded D-arabinose; and X is —C(O)—; (j) $R_1$ is 3,5-dihydroxy-phenyl; Z is an α-bonded D-arabinose; and X is —C(O)—; (k) $R_1$ is 3,5-dihydroxy-phenyl; Z is an α-bonded L-galactose; and X is —C(O)—; (l) $R_1$ is 3,5-dihydroxy-pyrimidinyl; Z is an α-bonded D-arabinose; and X is —C(O)—; (m) $R_1$ is 3,5-dihydroxy-pyrimidinyl; Z is an α-bonded L-galactose; and X is —C(O)—; or (n) $R_1$ is 2-(8-hydroxy)quinolinyl; Z is an α-bonded L-galactose; and X is —C(O)—.

32. A compound according to claim 31, in which $R_2$ is —$(CH_2)_8$COOCH$_3$; $R_3$ is methyl; Z is an α-bonded L-galactose; X is —C(O)— and $R_1$ is hydrogen; 4-hydroxy-3-methoxy-phenyl; 2-hydroxy-5-methyl-phenyl; 2-hydroxy-3-nitro-phenyl; 3,5-dihydroxy-phenyl; 3,5-dihydroxy-pyrimidinyl or 2-(8-hydroxy)quinolinyl.

33. A compound according to claim 32, in which $R_2$ is —$(CH_2)_8$COOCH$_3$; $R_3$ is methyl; Z is an α-bonded L-galactose; X is —C(O)— and $R_1$ is 4-hydroxy-3-methoxy-phenyl.

34. A compound of the formula II according to claim 1, in which $R_2$ is —$(CH_2)_8$COOCH$_3$; $R_3$ is methyl; and (a) $R_1$ is hydrogen; Z is an α-bonded D-arabinose; and X is —C(O)—; (b) $R_1$ is hydrogen; Z is an α-bonded L-2-fluoro-fucose; and X is —C(O)—; (c) $R_1$ is $CH_3$; Z is an α-bonded D-arabinose; and X is —C(O)—; (d) $R_1$ is $CH_3$; Z is an α-bonded L-2-fluoro-fucose; and X is —C(O)—; (e) $R_1$ is $CH_3$; Z is an α-bonded L-2-amino-fucose; and X is —C(O)—; (f) $R_1$ is $CH_3$; Z is an α-bonded L-galactose; and X is —C(O)—; (g) $R_1$ is $CH_3$; Z is an α-bonded L-glucose; and X is —C(O)—; (h) $R_1$ is $CH_3$; Z is an α-bonded L-galactose; and X is —C(O)OCH$_2$—; (i) $R_1$ is $CH_3$; Z is an α-bonded L-glucose; and X is —C(O)OCH$_2$—; (j) $R_1$ is $CH_3$; Z is an α-bonded D-arabinose; and X is S(O)$_2$; (k) $R_1$ is $CH_3$; Z is an α-bonded D-arabinose; and X is —C(O)SCH$_2$—; (l) $R_1$ is $CF_3$; Z is an α-bonded D-arabinose; and X is —C(O)—; (m) $R_1$ is $CH_2$OH; Z is an α-bonded D-arabinose; and X is —C(O)—; (n) $R_1$ is —$CH_2$—CH═$CH_2$; Z is an α-bonded D-arabinose; and X is —C(O)OCH$_2$—; (o) $R_1$ is —$CH_2$—CH═$CH_2$; Z is an α-bonded L-galactose; and X is —C(O)OCH$_2$—; (p) R$_1$ is phenyl; Z is an α-bonded L-galactose; and X is —C(O)OCH$_2$—; (q) R$_1$ is 2-hydroxy-5-methyl-phenyl; Z is an α-bonded D-arabinose; and X is —C(O)—; (r) R$_1$ is 2-hydroxy-5-methyl-phenyl; Z is an α-bonded L-galactose; and X is —C(O)—; (s) R$_1$ is 2-hydroxy-5-fluoro-phenyl; Z is an α-bonded D-arabinose; and X is —C(O)—; (t) R$_1$ is 4-hydroxy-3-methoxy-phenyl; Z is an α-bonded D-arabinose; and X is —C(O)—; (u) R$_1$ is 3,5-dihydroxy-phenyl; Z is an α-bonded L-galactose; and X is —C(O)—; (v) R$_1$ is 3,5-dihydroxy-phenyl; Z is an α-bonded L-2-amino-fucose; and X is —C(O)—; (w) R$_1$ is 3,5-dihydroxy-phenyl; Z is an α-bonded D-arabinose; and X is —C(O)OCH$_2$— or (x) R$_1$ is 3,5-dihydroxy-pyrimidinyl; Z is an α-bonded D-arabinose; and X is —C(O)—.

35. A compound according to claim 34, in which R$_1$ is CH$_3$; R$_2$ is —(CH$_2$)$_8$COOCH$_3$; R$_3$ is methyl; Z is an α-bonded L-galactose and X is —C(O)— or —C(O)OCH$_2$—.

36. A process for the preparation of a compound of the formula I

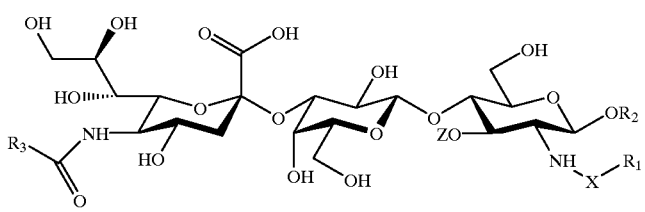
(I)

in which Z is an α-bonded pyranose of the formula III

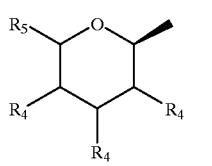
(III)

with the proviso that Z is not L-fucose, R$_1$ is hydrogen, C$_1$–C$_{20}$alkyl, C$_1$–C$_{20}$alkenyl, C$_3$–C$_{15}$cycloalkyl or a mono- or bicyclic C$_6$–C$_{10}$aryl or C$_2$–C$_9$heteroaryl, where alkyl, alkenyl, cycloalkyl, aryl and heteroaryl are unsubstituted or mono- or polysubstituted by a substituent chosen from the group consisting of OH, halogen, halo-C$_1$–C$_{18}$alkyl, nitro, C$_1$–C$_{18}$alkyl, C$_1$–C$_{18}$alkoxy, amino, mono-C$_1$–C$_{18}$alkylamino, di-C$_1$–C$_{18}$alkylamino, benzylamino, sulfhydryl, thio-C$_1$–C$_{18}$alkyl and C$_1$–C$_{18}$alkylcarboxamide; R$_2$ is C$_1$–C$_{18}$alkyl, mono- or polysubstituted C$_1$–C$_{18}$alkyl, C$_3$–C$_8$cycloalkyl or mono- or polysubstituted C$_3$–C$_8$cycloalkyl, where one or more CH$_2$ groups in the alkyl and in the cycloalkyl, independently of one another may be replaced by oxygen, sulfur or an imino group and the substituents are chosen from the group consisting of OH, SH, NH$_2$, carboxamide, C(O)O and C$_1$–C$_{18}$alkoxycarbonyl; R$_3$ is a methyl or hydroxymethyl group; the individual R$_4$ independently of one another are hydrogen, OH, C$_1$–C$_8$alkyl, O-C$_1$–C$_8$alkyl, halogen, NH$_2$, SH or NHC(O-C$_1$–C$_8$alkyl; R$_5$ is hydrogen, C$_1$–C$_8$alkyl or (CH$_2$)$_m$R$_4$, in which m is a number from 1 to 5; and X is —C(O)—, —C(S)—, —S(O)$_2$—, —C(O)Y— or —C(S)Y—, in which Y is NH, O, S, S-C$_1$–C$_6$alkylene, NHC$_1$–C$_6$alkylene or O-C$_1$–C$_6$alkylene, which comprises (a) reacting a compound of the formula V

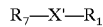
(V), in which (a') R$_7$ is halogen, X' is as defined above for X and R$_1$ is as defined above, or (a'') R$_7$ is C(O) or C(S), X' is —N= and R$_1$ is as defined above, or (a''') R$_7$ is OH, X' is as defined above for X and R$_1$ is as defined above, directly after in situ activation, with a compound of the formula IV

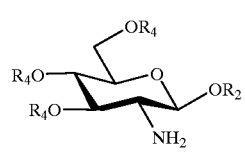
(IV)

in which R$_2$ is as defined above and the individual R$_4$ independently of one another are hydrogen, acetyl, propionyl, butyryl or benzoyl, any acetyl, propionyl, butyryl or benzoyl groups present being split off with a basic alcohol solution, to give a compound of the formula VI

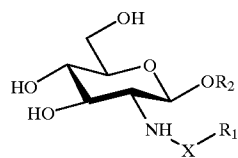
(VI)

in which R$_2$, R$_1$ and X are as defined above;

(b) reacting the compound of the formula VI with uridine di-phosphate-galactose in the presence of β(1→4) galactose transferase and then with cytidine monophosphate-sialic acid in the presence of α(2→3)sialic acid transferase to give a compound of the formula VII

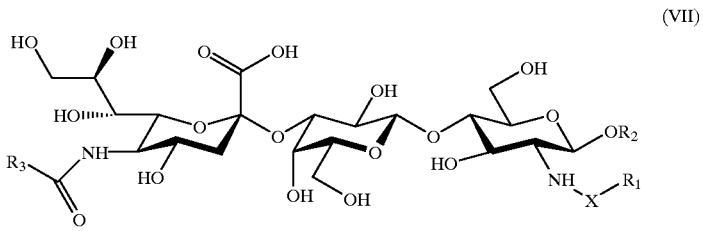

(VII)

in which $R_1$, $R_2$, $R_3$ and X are as defined above, and (c) reacting the resulting product with a guanosine di-phosphate-activated donor of the formula XI

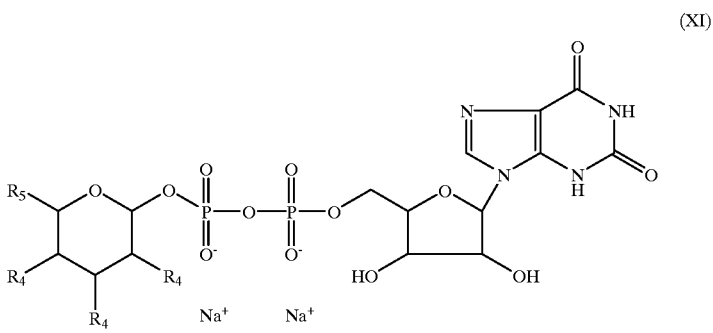

(XI)

in which $R_4$ and $R_5$ are as defined above, in the presence of fucose transferase VI to give a compound of the formula I.

37. The process for the preparation of a compound of the formula I according to claim 36, which comprises
(a) reacting a compound of the formula VI according to claim 36 with uridine di-phosphate-galactose in the presence of β(1→4)galactose transferase and then with cytidine mono-phosphate-sialic acid in the presence of α(2→3)sialic acid transferase to give a compound of the formula VII according to claim 36 and
(b) reacting the resulting product with a compound of the formula XI according to claim 36 in the presence of fucose transferase to give a compound of the formula I.

38. The process for the preparation of a compound of the formula II in which Z is an α-bonded pyranose of the formula III

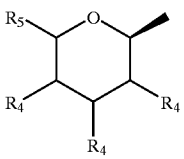

(III)

with the proviso that Z is not L-fucose, $R_1$ is hydrogen, $C_1$–$C_{20}$alkyl, $C_1$–$C_{20}$alkenyl, $C_3$–$C_{15}$cycloalkyl or a mono- or bicyclic $C_6$–$C_{10}$aryl or $C_2$–$C_9$heteroaryl, where alkyl, alkenyl, cycloalkyl, aryl and heteroaryl are unsubstituted or mono- or polysubstituted by a substituent chosen from the group consisting of OH, halogen, halo-$C_1$–$C_{18}$alkyl, nitro, $C_1$–$C_{18}$alkyl, $C_1$–$C_{18}$alkoxy, amino, mono-$C_1$–$C_{18}$alkylamino, di-$C_1$–$C_{18}$alkylamino, benzylamino, (II)

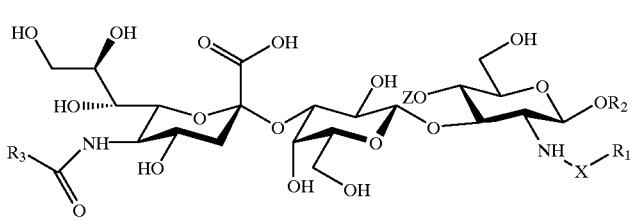

sulfhydryl, thio-$C_1$–$C_{18}$alkyl and $C_1$–$C_{18}$alkylcarboxamide; $R_2$ is $C_1$–$C_{18}$alkyl, mono- or polysubstituted $C_1$–$C_{18}$alkyl, $C_3$–$C_8$cycloalkyl or mono- or polysubstituted $C_3$–$C_8$cycloalkyl, where one or more $CH_2$ groups in the alkyl and in the cycloalkyl, independently of one another may be replaced by oxygen, sulfur or an imino group and the substituents are chosen from the group consisting of OH, SH, $NH_2$, carboxamide, C(O)O and $C_1$–$C_{18}$alkoxycarbonyl; $R_3$ is a methyl or hydroxymethyl group; the individual $R_4$ independently of one another are hydrogen, OH, $C_1$–$C_8$alkyl, O-$C_1$–$C_8$alkyl, halogen, $NH_2$, SH or NHC(O-$C_1$–$C_8$alkyl; $R_5$ is hydrogen, $C_1$–$C_8$alkyl or $(CH_2)_mR_4$, in which m is a number from 1 to 5; and X is —C(O)—, —C(S)—, —S(O)$_2$—, —C(O)Y— or —C(S)Y—, in which Y is NH, O, S, S-$C_1$–$C_6$alkylene, NH-$C_1$–$C_6$alkylene or O-$C_1$–$C_6$alkylene, which comprises (a) reacting a compound of the formula IV with a compound of the formula V according to claim 36, (b) reacting the compound of the formula VI according to claim 36 with uridine di-phosphate-galactose in the presence of β(1→3)galactose transferase and then cytidine mono-phosphate-sialic acid in the presence of α(2→3)sialic acid transferase to give a compound of the formula VIII

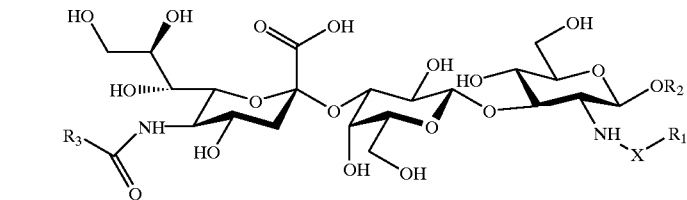

(VIII)

in which $R_1$, $R_2$, $R_3$ and X are as defined above, and (c) reacting the resulting product with a compound of the formula XI according to claim 36 in the presence of fucose transferase to give a compound of the formula II.

39. The process for the preparation of a compound of the formula II

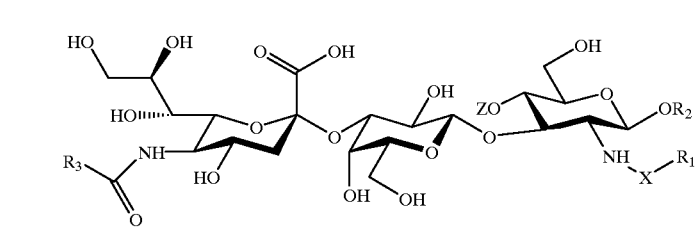

(II)

which comprises
(a) reacting a compound of the formula V $R_7$—X'—$R_1$          (V), in which
(a') $R_7$ is halogen, X' is as defined for X according to claim 36 and $R_1$ is as defined according to claim 36, or
(a") $R_7$ is C(O) or C(S), X' is —N= and $R_1$ is as defined above, or (a'") $R_7$ is OH, X' is as defined above for X and $R_1$ is as defined above, directly after in situ activation, with a compound of the formula IX

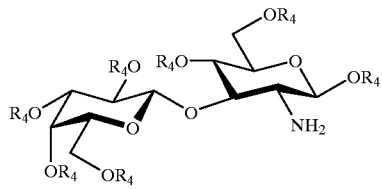

(IX)

in which $R_2$ is as defined above and the individual $R_4$ independently of one another are hydrogen, acetyl, propionyl, butyryl or benzoyl, any acetyl, propionyl, butyryl or benzoyl groups present being split off with a basic alcohol solution, to give a compound of the formula X

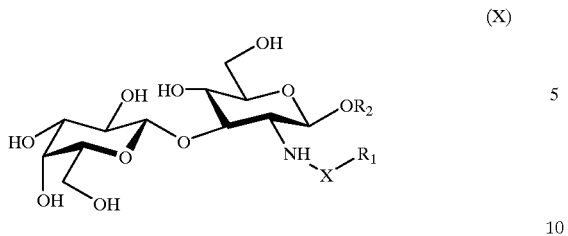

(X)

in which $R_2$, $R_1$ and X are as defined above;
(b) reacting the compound of the formula X with cytidine mono-phosphate-sialic acid in the presence of α(2→3) sialic acid transferase to give a compound of the formula VIII

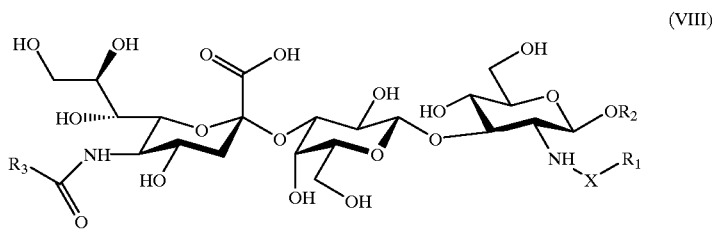

(VIII)

in which $R_1$, $R_2$, $R_3$ and X are as defined above, and
(c) reacting the resulting product with a compound of the formula XI in the presence of fucose transferase to give a compound of the formula II.

40. The process for the preparation of a compound of the formula II according to claim 36, which comprises
(a) reacting a compound of the formula X according to claim 36 with cytidine mono-phosphate-sialic acid in the presence of α(2→3)sialic acid transferase to give a compound of the formula VIII according to claim 36 and
(b) reacting the resulting product with a compound of the formula XI according to claim 36 in the presence of fucose transferase to give a compound of the formula II.

41. The process for the preparation of a compound of the formula II

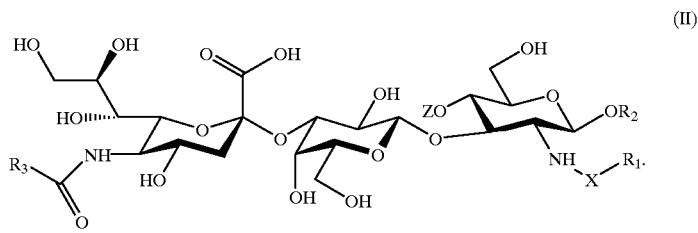

(II)

which comprises
(a) reacting a compound of the formula VI according to claim 36 with uridine di-phosphate-galactose in the presence of β(1→3) galactose transferase and then with cytidine mono-phosphate-sialic acid in the presence of α(2→3) sialic acid transferase to give a compound of the formula VII

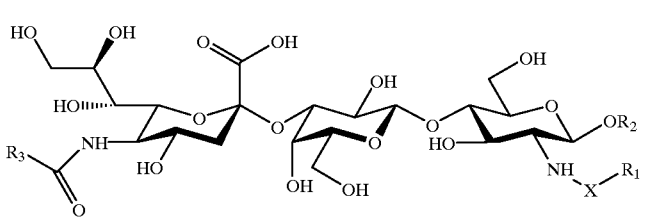
(VII)

in which $R_1$, $R_2$, $R_3$ and are as defined according to claim 36, and (b) reacting the resulting product with a compound of the formula XI according to claim 36 in the presence of fucose transferase to give a compound of the formula II.

42. The process as claimed in claim 36, wherein the galactosylation and the sialylation are carried out simultaneously.

43. The process as claimed in claim 36, wherein the galactosylation and the sialylation are carried out in succession.

44. The process as claimed in claim 37, wherein the galactosylation and the sialylation are carried out simultaneously.

45. The process as claimed in claim 37, wherein the galactosylation and the sialylation are carried out in succession.

46. The process as claimed in claim 38, wherein the galactosylation and the sialylation are carried out simultaneously.

47. The process as claimed in claim 38 wherein the galactosylation and the sialylation are carried out in succession.

48. The process as claimed in claim 39, wherein the galactosylation and the sialylation are carried out simultaneously.

49. The process as claimed in claim 39, wherein the galactosylation and the sialylation are carried out in succession.

50. The process as claimed in claim 41, wherein the galactosylation and the sialylation are carried out simultaneously.

51. The process as claimed in claim 41, wherein the galactosylation and the sialylation are carried out in succession.

52. A pharmaceutical preparation comprising an active amount of a compound according to claim 1, by itself or together with other active ingredients, and a pharmaceutical carrier.

53. The pharmaceutical preparation according to claim 52 further including an adjunct.

* * * * *

UNITED STATES PATENT AND TRADEMARK OFFICE
CERTIFICATE OF CORRECTION

PATENT NO. : 6,169,077 B1
DATED : January 2, 2001
INVENTOR(S) : Reinhold Oehrlein It is certified that error appears in the above-identified patent and that said Letters Patent is hereby corrected as shown below:

Column 105,
Lines 65 and 66, "SH or NHC(O-$C_1$-$C_8$alkyl;" should read -- SH or NHC(O)-$C_1$-$C_8$alkyl; --.

Column 106,
Line 2, "NHC$_1$-$C_6$alkylene" should read -- NH-$C_1$-$C_6$alkylene --.

Column 109,
Lines 9 and 10, "SH or NHC(O-$C_1$$C_8$alkyl;" should read -- SH or NHC(O)-$C_1$-$C_8$alkyl; --.

Signed and Sealed this

Fourteenth Day of August, 2001

*Attest:*

*Attesting Officer*

NICHOLAS P. GODICI
*Acting Director of the United States Patent and Trademark Office*